United States Patent [19]
Gobron et al.

[11] Patent Number: 6,162,209
[45] Date of Patent: Dec. 19, 2000

[54] MULTI-FUNCTION SURGICAL INSTRUMENT TOOL ACTUATOR ASSEMBLY

[75] Inventors: Stephane Gobron, Gosport; Tim Ward, Ellettsville; W. Michael Mereness, Bloomington, all of Ind.; Mark Isom Richards, Grand Prairie, Tex.; Srinivas Nishtala, Bloomington, Ind.

[73] Assignee: Scimed Life Systems, Inc., Maple Grove, Minn.

[21] Appl. No.: 09/192,568

[22] Filed: Nov. 17, 1998

[51] Int. Cl.[7] ................................................. A61B 17/00
[52] U.S. Cl. ........................... 606/1; 606/108; 606/113; 606/167
[58] Field of Search ....................... 606/1, 113, 108, 606/205, 167, 53

[56] References Cited

U.S. PATENT DOCUMENTS

| 5,312,391 | 5/1994 | Wilk | 606/180 |
|---|---|---|---|
| 5,314,424 | 5/1994 | Nicholas | 606/41 |
| 5,535,759 | 7/1996 | Wilk | 128/898 |
| 5,536,248 | 7/1996 | Weaver et al. | 604/54 |
| 5,542,948 | 8/1996 | Weaver et al. | 606/113 |
| 5,562,655 | 10/1996 | Mittelstadt et al. | 606/1 |
| 5,667,473 | 9/1997 | Finn et al. | 600/104 |
| 5,843,091 | 12/1998 | Holsinger et al. | 606/108 |
| 5,961,526 | 10/1999 | Chu et al. | 606/113 |

*Primary Examiner*—Linda M. Dvorak
*Assistant Examiner*—Jocelyn Ram
*Attorney, Agent, or Firm*—Kenyon & Kenyon

[57] ABSTRACT

A tool actuating assembly for a multi-function surgical instrument is disclosed. The tool actuating assembly of the present invention can be utilized in a variety of differently configured multi-function surgical instruments and can be embodied in various physical configurations. The tool actuating assembly of the present invention provides for more efficient use of the tools of the instrument by the surgeon who is utilizing the instrument.

23 Claims, 54 Drawing Sheets

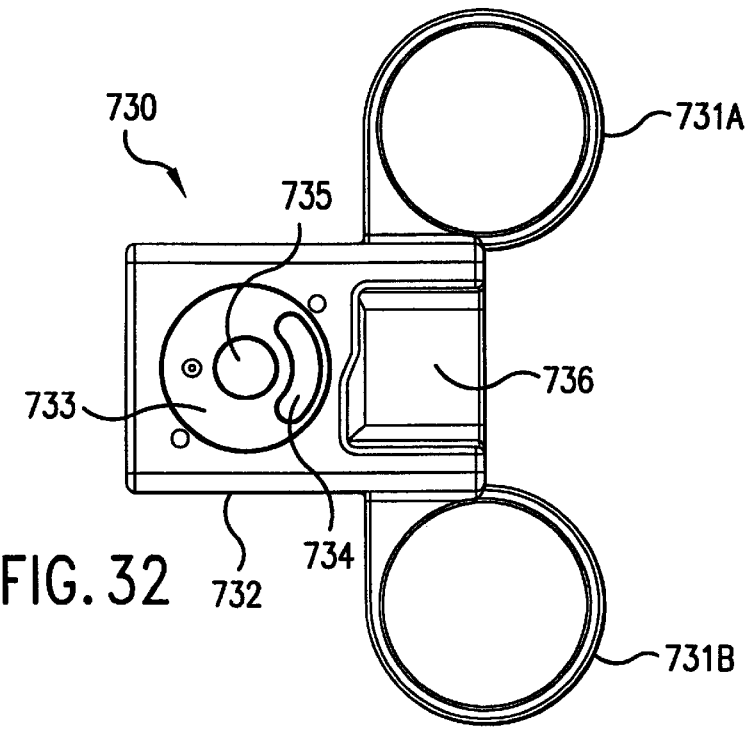
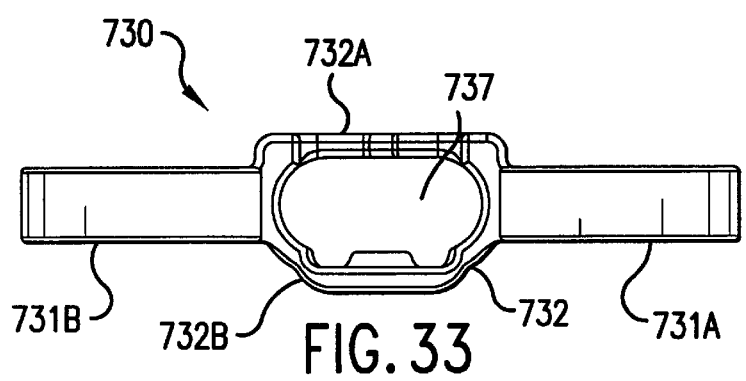
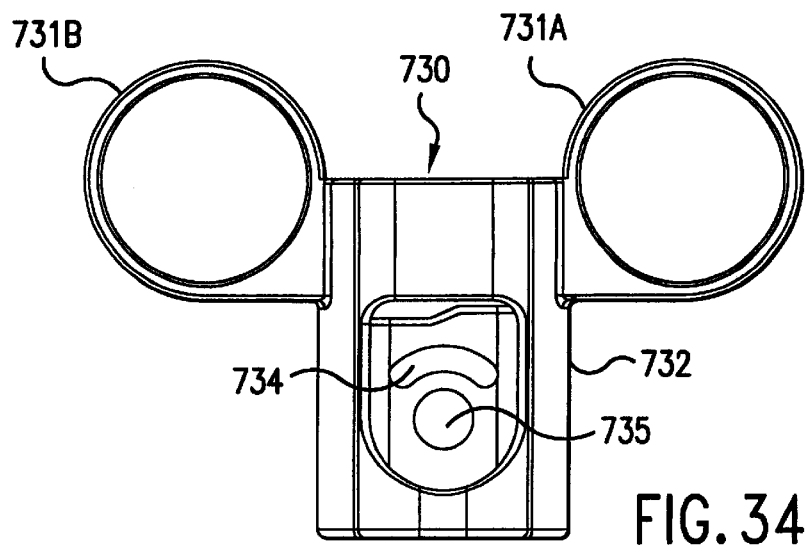

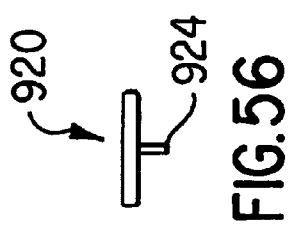
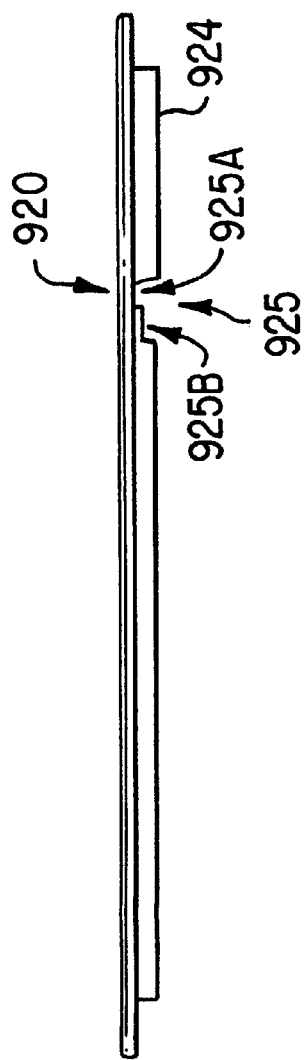
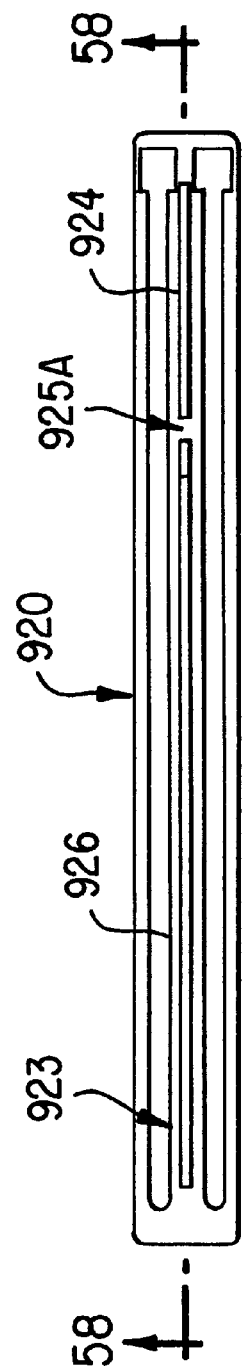
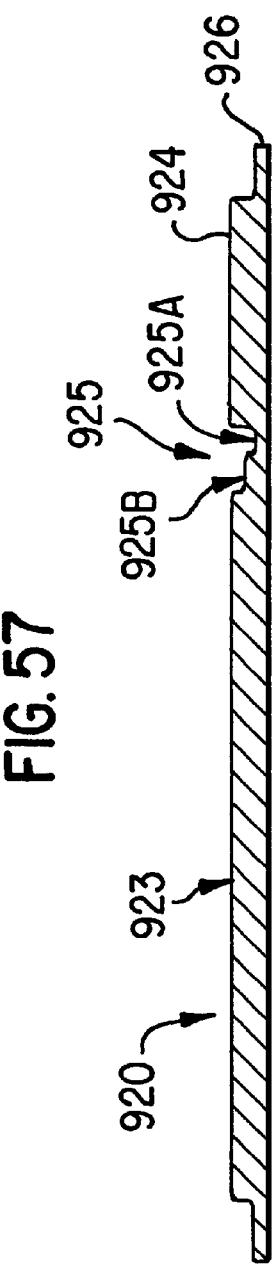
FIG. 56
FIG. 55
FIG. 57
FIG. 58

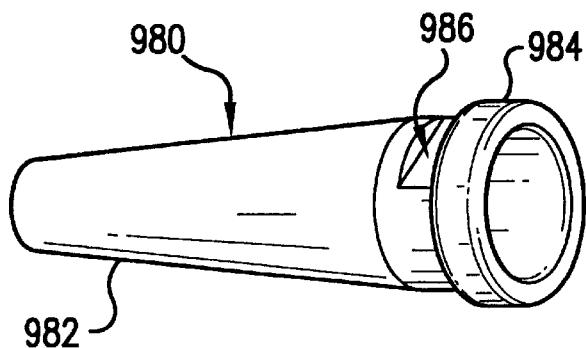
FIG. 72
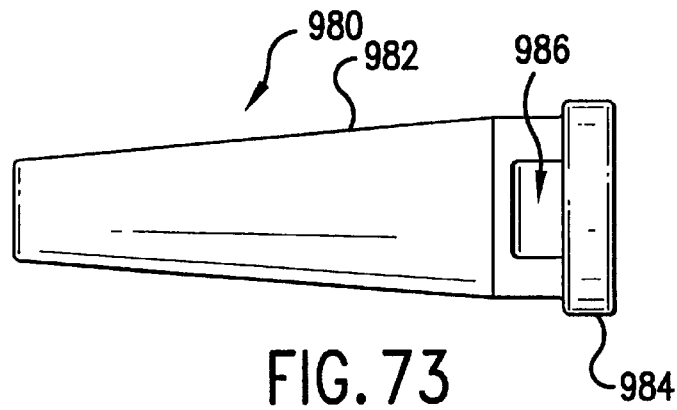
FIG. 73
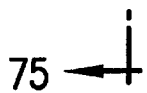
FIG. 74
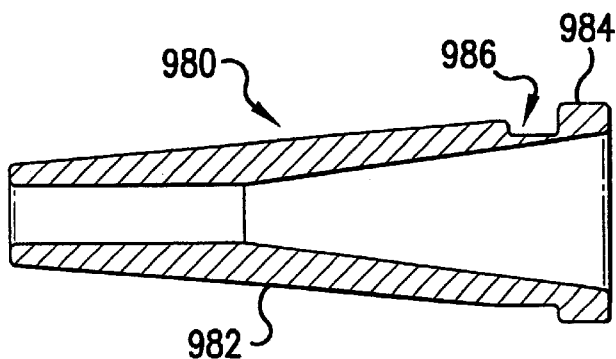
FIG. 75

MULTI-FUNCTION SURGICAL INSTRUMENT TOOL ACTUATOR ASSEMBLY

BACKGROUND OF THE INVENTION

The present invention relates to a multi-function surgical instrument. More specifically, the invention provides a surgical tool actuator assembly for a multi-function surgical instrument.

Currently, multi-function surgical instruments are being utilized by surgeons when performing surgical procedures. These multi-function surgical instruments contain multiple surgical tools within the single instrument which allows the surgeon to perform a procedure without requiring the surgeon to remove and insert multiple instruments within the patient. The incorporation of multiple tools within a single instrument provides efficiencies for the surgeon when performing the procedure.

There are drawbacks, however, with currently known multi-function surgical instruments. Because multiple tools are incorporated into the single instrument, the mechanism of the surgical instrument that is utilized to operate the tools within the instrument can be complex and/or inefficient to use. Thus, the efficiencies that are obtained for a physician by incorporating multiple tools within a single instrument can be negated by the complexities and/or inefficiencies involved with operating the tools of the instrument.

Therefore, it would be desirable to provide a multi-function surgical instrument tool actuating assembly that would provide for more efficient use of the tools of the instrument by the surgeon who is utilizing the instrument.

SUMMARY OF THE INVENTION

The present invention is directed to overcoming many of the deficiencies that exist with the tool operating mechanisms of multi-function surgical instruments. The present invention provides an improved tool actuating assembly for a multi-function surgical instrument. The tool actuating assembly of the present invention can be utilized in a variety of differently configured multi-function surgical instruments and can be embodied in various physical configurations.

BRIEF DESCRIPTION OF THE DRAWINGS

FIG. 32 is a top view of the sliding finger ring assembly of the embodiment of FIG. 25.

FIG. 33 is a rear view of the sliding finger ring assembly of FIG. 32.

FIG. 34 is a bottom view of the sliding finger ring assembly of FIG. 32.

FIG. 55 is a side view of the guide bar of FIG. 53.

FIG. 56 is a front view of the guide bar of FIG. 53.

FIG. 57 is a bottom view of the guide bar of FIG. 53.

FIG. 58 is a cross-sectional view of the guide bar of FIG. 53 as taken along line 58—58 of FIG. 57.

FIG. 72 is a perspective view of a sheath stress relief member that can be utilized with the multi-function surgical instrument of FIG. 51.

FIG. 73 is a side view of the sheath stress relief member of FIG. 72.

FIG. 74 is a front view of the sheath stress relief member of FIG. 72.

FIG. 75 is a cross-sectional view of the sheath stress relief member of FIG. 72 taken along line 75—75 of FIG. 74.

DETAILED DESCRIPTION

Figure 1:
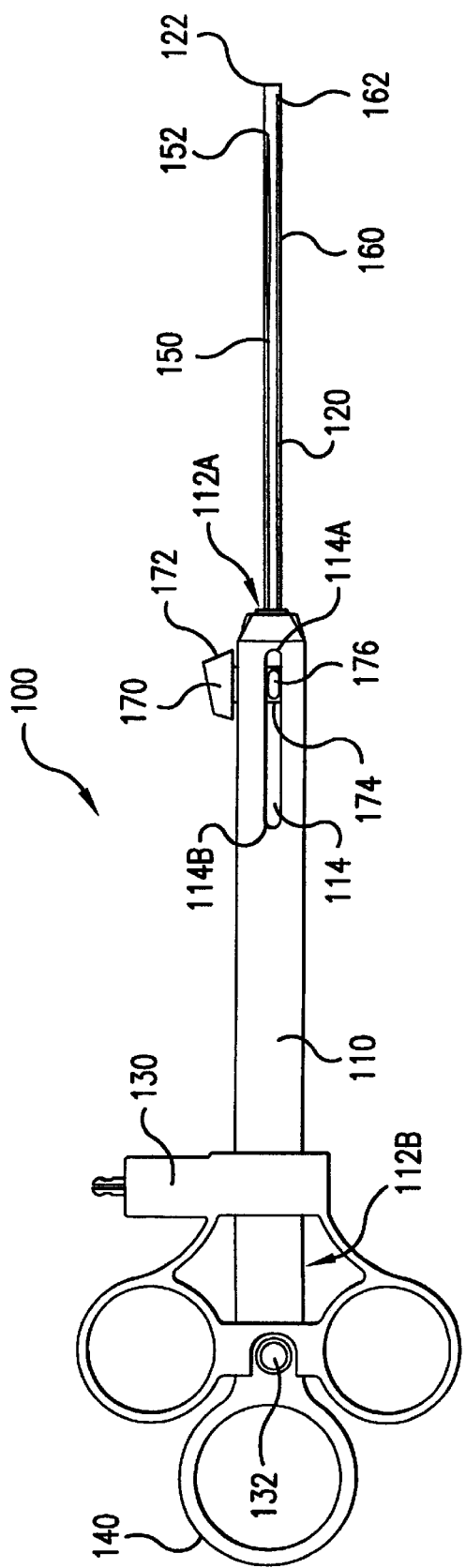
FIG. 1 is a side view of a multi-function surgical instrument that incorporates a first embodiment for a tool actuator assembly in accordance with the present invention.

FIG. 1 illustrates a first embodiment for a surgical tool actuator assembly in accordance with the principles of the present invention. It should be noted that the present invention can be practiced in any of a variety of different configurations for a surgical instrument where multiple surgical tools are contained within the surgical instrument and the present invention is not limited to being practiced in any particular embodiment for the multi-function surgical instrument itself. A first embodiment for a multi-function surgical instrument and a first embodiment for the tool actuator assembly of the present invention are illustrated in FIG. 1.

As is illustrated in FIG. 1, surgical instrument 100 is a multi-function surgical instrument that contains a first surgical tool 150, which is a snare, and a second surgical tool 160, which is disclosed in the embodiment of FIG. 1 as being an injection needle. As can be seen in FIG. 1, surgical instrument 100 includes a body 110, a shaft, or sheath, 120, a finger ring 130, and an actuator button 170. Snare 150 and needle 160 are disposed within sheath 120 when both tools are in a non-operative position. Snare 150 and needle 160 can be any of a variety of known devices and the present invention is not limited to any particular embodiment for the snare and the needle. Additionally, as mentioned previously, the present invention is not limited to an embodiment where the first surgical tool 150 is a snare and the second surgical tool 160 is a needle. The present invention can be practiced with any of a variety of tools, e.g., a brush, grasper, balloon, cautery tool, basket, etc.

Body 110 is a generally tubular member that includes a guiding slot 114 in a distal end 112A of the body 110 and includes a thumb ring 140 at a proximal end 112B of the body. Also included in body 110 is injection port 132 which is utilized to provide fluid to surgical instrument 100 for injection into the body of a patient through needle 160. Guiding slot 114 is comprised of openings on opposed sides of body 110 such that an opening extending through body 110 is formed by guiding slot 114. Actuator button 170 is disposed within body 110 for sliding motion within body 110. As such, actuator button 170 includes a head portion 172, an elongated stem portion 174, and slot guide 176. Slot guide 176 is comprised of two guide tabs that are disposed on opposed sides of elongated stem portion 174 and which are received within guiding slot 114 of body 110. As such, actuator button 170 is disposed within body 110 for sliding motion with respect to body 110 by positioning slot guide 176 within guiding slot 114. Additionally, actuator button 170 is rigidly attached to sheath 120, which is disposed within body 110 for sliding motion with respect to body 110. Actuator button 170 is utilized to retract a portion of sheath 120 within body 110. As will be further explained, the retraction of sheath 120 within body 110 exposes the distal end 162 of needle 160 beyond the distal end 122 of sheath 120.

Sheath, or shaft, 120, in the embodiment of FIG. 1–4, and for the other embodiments disclosed later in this specification or contemplated by those skilled in the art, can be comprised of either a rigid or a flexible structure. The present invention is not limited to any particular physical configuration for sheath, or shaft, 120 and its structure is determined by the particular type of surgical instrument with which the present invention is utilized.

Finger ring 130 is disposed on body 110 for sliding motion on body 110. As will be further explained below, finger ring 130 is attached to snare 150 and controls the movement of snare 150 to both retract snare 150 within sheath 120 and to extend snare 150 beyond the distal end 122 of sheath 120.

Figure 2:
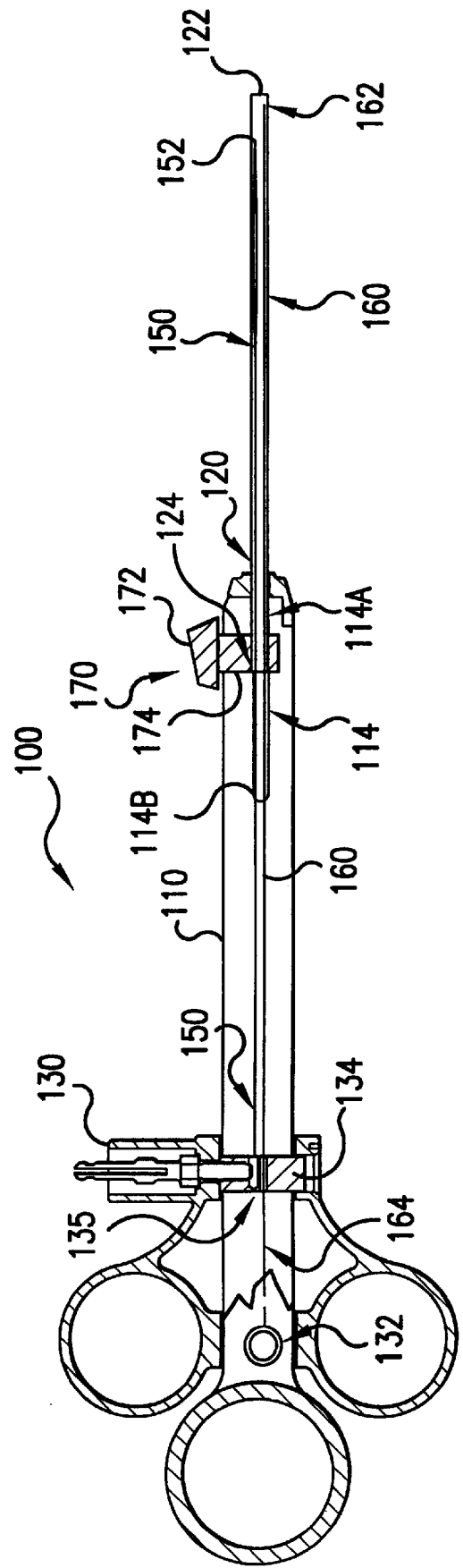
FIG. 2 is a cross-sectional view of the multi-function surgical instrument and tool actuator assembly of FIG. 1.

FIG. 2 is a cross sectional view of the surgical instrument 100 of FIG. 1 that illustrates the internal connections of the snare 150, needle 160, and sheath 120 within the surgical instrument 100. As can be seen in FIG. 2, needle 160 is a fixed length needle and is rigidly attached at its proximal end 164 to injection port 132. Snare 150 is rigidly attached to snare attachment member 134 of finger ring 130. Snare attachment member 134 includes an aperture 135 that extends therethrough such that needle 160 is able to extend through snare attachment member 134.

Also illustrated in FIG. 2 is the attachment of sheath 120 to actuator button 170. Proximal end 124 of sheath 120 is rigidly attached to actuator button 170. Thus, since sheath 120 is disposed within body 110 but is not directly attached to body 110, sheath 120 is able to be retracted into, and extended from, body 110 by the user sliding actuator button 170 within guiding slot 114 of body 110. The methods of attachment of needle 160 to body 110 (through attachment to injection port 132), snare 150 to attachment member 134, and actuator button 170 to sheath 120 may be by any of a variety of methods and the present invention is not limited to any particular attachment method. For example, each member may be glued to its respective attachment member or it may be attached by utilizing attachment hardware, such as screws or rivets.

The operation of each tool within surgical instrument 100 will now be described. FIG. 1 illustrates the surgical instrument 100 in a configuration where both the snare 150 and the needle 160 are disposed completely within sheath 120. As can be seen, in this configuration where both the snare 150 and needle 160 are disposed within sheath 120, finger ring 130 is disposed at the proximal end 112B of body 110 and actuator button 170 is disposed at the distal end 114A of guiding slot 114.

Figure 3:
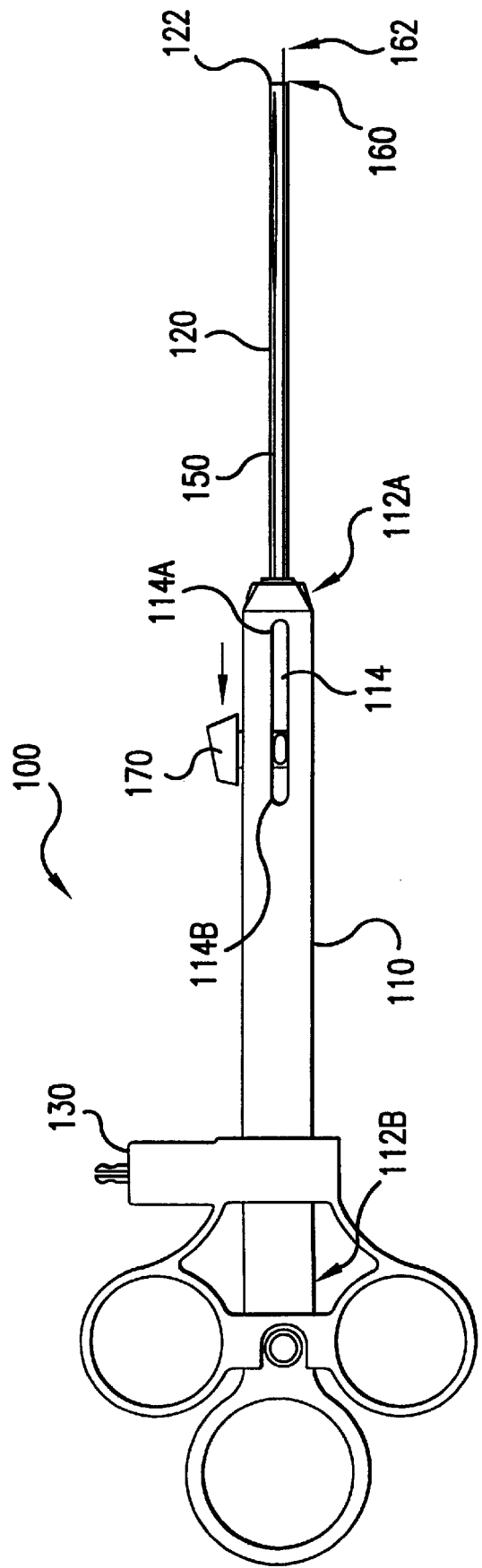
FIG. 3 is a side view of the surgical instrument of FIG. 1 with the needle exposed from the sheath.

FIG. 3 illustrates a configuration for surgical instrument 100 where needle 160 is now exposed from the distal end 122 of sheath 120. As can be seen, actuator button 170 has now been moved proximally with respect to body 110 within guiding slot 114. Since sheath 120 is rigidly attached to actuator button 170, as actuator button 170 is moved proximally along body 110, sheath 120 is retracted within body 110. In effect, this decreases the effective length of the sheath 120 that extends from the distal end 112A of body 110. Since needle 160 has a fixed length and its length is selected such that the distal end 162 of needle 160 is disposed within sheath 120 when sheath 120 is extended from body 110, any retraction of sheath 120 within body 110 through operation of actuator button 170 will expose the distal end 162 of needle 160 from the distal end 122 of sheath 120. Thus, in order to expose needle 160 from sheath 120, needle 160 is not moved relative to body 110, however, sheath 120 is moved relative to body 110, thus exposing the distal end 162 of needle 160 from the distal end 122 of sheath 120. In this manner, a surgeon is able to control the extension and retraction of needle 160 from the surgical instrument by easily operating an actuator button that controls the movement of the sheath 120 of the surgical instrument.

Figure 4:
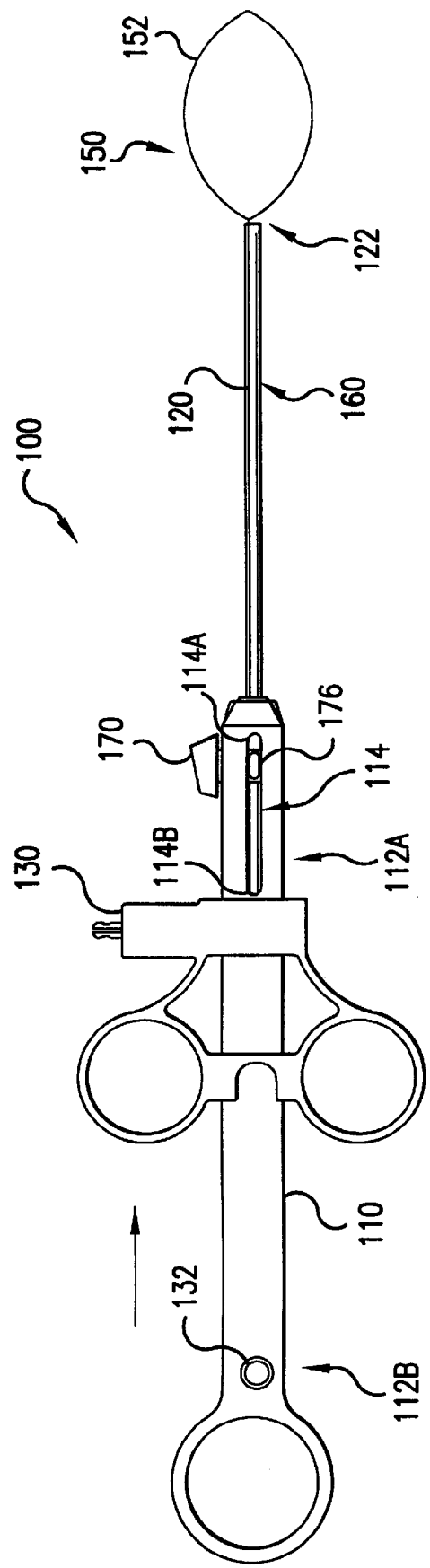
FIG. 4 is a side view of the surgical instrument of FIG. 1 with the snare loop exposed from the sheath.

FIG. 4 illustrates the operation of snare 150. As can be seen in FIG. 4, sliding finger ring 130 has now been moved distally along body 110 such that finger ring 130 is now in a second position. Since snare 150 is rigidly attached to finger ring 130, any movement of finger ring 130 along body 110 will also move the snare the same distance that the finger ring is moved. Thus, as finger ring 130 is moved to its second position distally along body 110, the distal end 152 of snare 150, which is the working part of snare 150, is disposed externally from distal end 122 of sheath 120. As was explained earlier, because snare attachment member 134, which provides for attachment of snare 150 to finger ring 130, includes aperture 135 therethrough, finger ring 130 is able to be moved on body 10 without effecting movement of needle 160. Finger ring 130 and attachment member 134 merely pass over needle 160 as needle 160 is positioned within aperture 135 in the snare attachment member 134. Thus, the movement and operation of snare 150 through operation of finger ring 130 is independent of the operation of needle 160, which is actuated through actuator button 170.

Thus, the present invention as embodied in FIGS. 1–4 provides for independent operation of a first surgical tool and a second surgical tool and easily operable mechanisms for independently actuating each tool.

Additional features that could be included with the embodiment of FIGS. 1–4 for the operating mechanism for actuating needle 160 are a biasing means to bias actuator button 170 in its first position, i.e., where the sheath 120 is fully extended from body 110, and a locking device to lock actuator button 170 in its second position where the actuator button has retracted sheath 120 within body 110 to expose needle 160 from sheath 120. These additional features are not required when practicing the present invention but may provide for further assisting an operator of the tool with its operation.

These features would not be limited to any particular embodiment and any of a variety of mechanisms could be utilized to implement these features. For example, a biasing spring could be provided within body 110 that could cooperate with actuator button 170 in order to bias actuator button 170 in its first position. If an operator desired to move actuator button 170 to its second position, the operator would merely apply sufficient pressure to actuator button 170 such that the pressure overcame the biasing force that biased the actuator button 170 into its first position. For the locking feature, should it be desired, a locking tab could be provide on actuator button 170 that could cooperate with a locking slot that could be provided on body 110. As the actuator button was moved proximally within guiding slot 114, the locking tab could ride up and over a cam surface associated with the locking slot and once the locking tab traveled over the cam surface the locking tab could be engaged within the slot that is included on body 110. When the operator desired to move actuator button 170 distally along body 110 to return actuator button 170 to its first position, the operator could manually lift the actuator button up and out of the slot on the body which would disengage the locking tab from the locking slot and then the actuator button could be moved back to its first position. Again, the present invention is not required to be practiced with these features and, if these features are incorporated, the present invention is not limited to any particular mechanism for implementing these features.

FIGS. 5–8 illustrate a second embodiment for a surgical tool actuator assembly in accordance with the present invention. As will be further explained, the present invention as embodied in FIGS. 5–8 operates in a similar manner to the embodiment of FIGS. 1–4, however, the operating mechanism for retracting sheath 220 within body 210 of multi-function surgical instrument 200 is comprised of a different structure.

Figure 5:
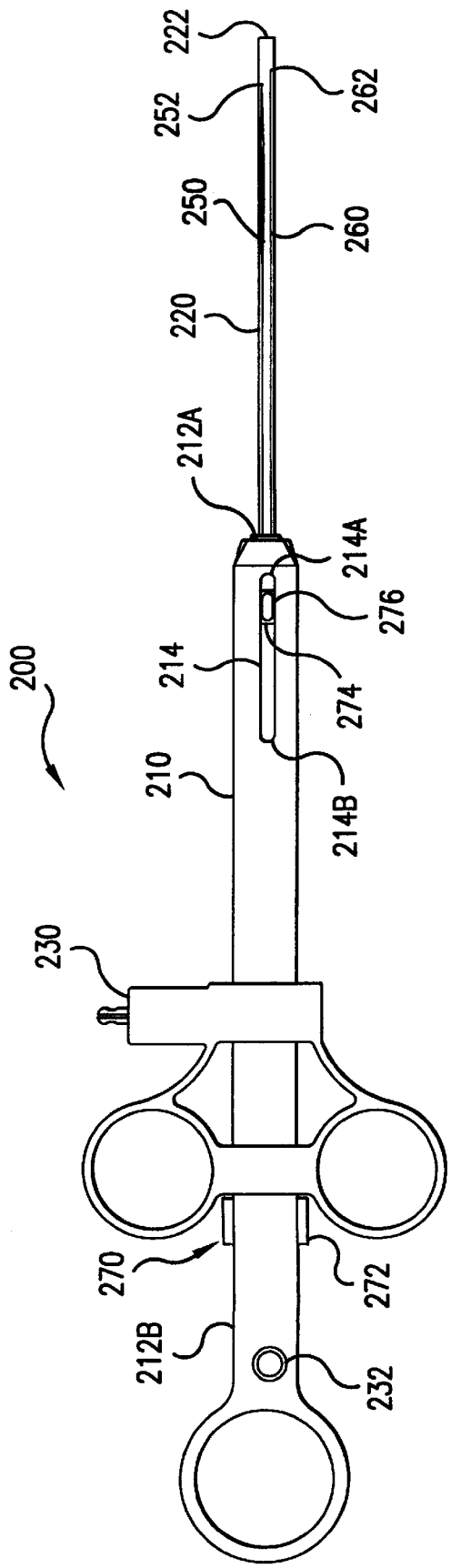
FIG. 5 is a side view of a multi-function surgical instrument that incorporates a second embodiment for the tool actuator assembly of the present invention.

Similar to the surgical instrument that was described in FIGS. 1–4, surgical instrument 200 of FIG. 5 also includes a body portion 210, a retractable sheath 220 that is partially disposed within distal end 212A of body portion 210, and a sliding finger ring 230 that is disposed on body 210 for sliding motion on the body. Surgical instrument 200 includes a first surgical tool 250 which is also disclosed as a snare as in the embodiment of FIGS. 1–4, and a second surgical tool 260 which is disclosed as a needle, also similar to the tool of FIGS. 1–4. Again, the present invention may be practiced by utilizing any of a variety of different tools with surgical instrument 200.

Surgical tool 200 also includes retracting member 270. As will be further described, retracting member 270 is rigidly attached, internal to body 210, to a proximal end 224 of sheath 220. Retracting member 270 incudes an engagement head portion 272 that is disposed at a proximal end 212B of surgical instrument 200 and a sheath attachment portion 274 that is disposed within body 210 at the distal end 212A of surgical instrument 200. Sheath attachment portion 274 includes slot guides 276 which are disposed on opposed sides of sheath attachment portion 274. As in the embodiment of FIGS. 1–4, slot guides 276 are received within guiding slot 214 that is included in body 210 at distal end 212A of surgical instrument 200.

Figure 6:
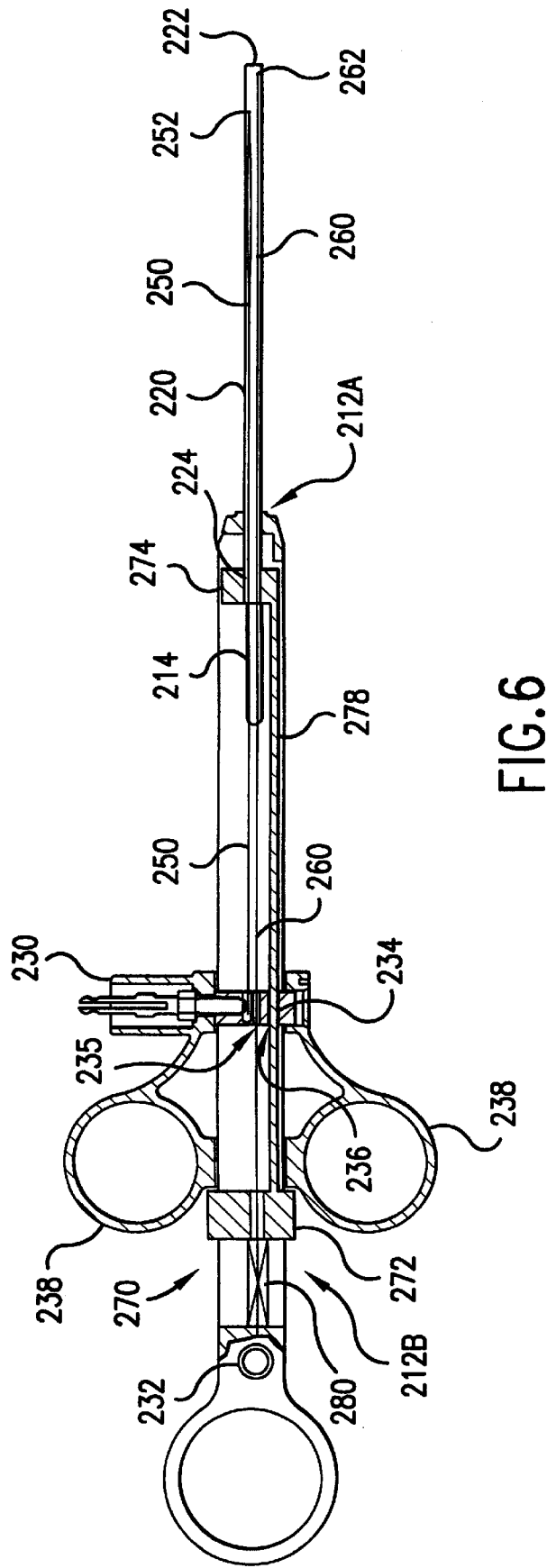
FIG. 6 is a cross-sectional view of the multi-function surgical instrument and tool actuator assembly of FIG. 5.

FIG. 6 is a cross-sectional view of the surgical instrument 200 of FIG. 5 which illustrates the attachments of snare 250, needle 260, and sheath 220 to the surgical instrument 200. As in the embodiment of FIGS. 1–4, needle 260 is comprised of a fixed length member and is rigidly attached to injection port 232 that is disposed in the proximal end 212B of surgical instrument 200. Injection port 232 is utilized to provide a fluid that is to be injected into the body of a patient to injection needle 260. Also as was described previously for the embodiment of FIGS. 1–4, snare 250 is rigidly attached to snare attachment member 234 which is included in sliding finger ring 230. Snare attachment member 234 includes a first aperture 235 which extends completely therethrough such that needle 260 can extend through snare attachment member 234 for rigid attachment to injection port 232. Sheath 220 is rigidly attached at its proximal end 224 to sheath attachment portion 274 of retracting member 270. Sheath attachment portion 274 of retracting member 270 is connected to engagement head portion 272 of retracting member 270 by retraction connecting member 278. Retraction connecting member 278 is an elongated member that rigidly connects sheath attachment portion 274 to engagement head portion 272. Retraction connecting member 278 is disposed within hollow body 210 of surgical instrument 200. Snare attachment member 234 includes a second aperture 236 through which extends retraction connecting member 278.

As can be seen in FIG. 6, engagement head portion 272 of retracting member 270 is disposed on body 210 of surgical instrument 200 to the rear of the two finger rings 238 that are included on sliding finger ring assembly 230. Biasing member 280 is disposed within body 210 of surgical instrument 200 and is utilized to bias retracting member 270 to a first position which, as will be explained, fully extends sheath 220 from body 210 of surgical instrument 200.

The operation of the tools of surgical instrument 200 will now be explained. As is illustrated in FIG. 5, both the snare 250 and needle 260 are fully retracted within sheath 220 of surgical instrument 200. As such, sliding finger ring 230 is in a first position at the proximal end 212B of body 210 and the retracting member 270, and consequently slot guides 276 of retracting member 270, are in a first position where slot guides 276 are positioned at the distal end 214A of guiding slot 214 in body 210. Thus, in this first position for retracting member 270, sheath 220 is fully extended from body 210 of the surgical instrument 200.

Figure 7:
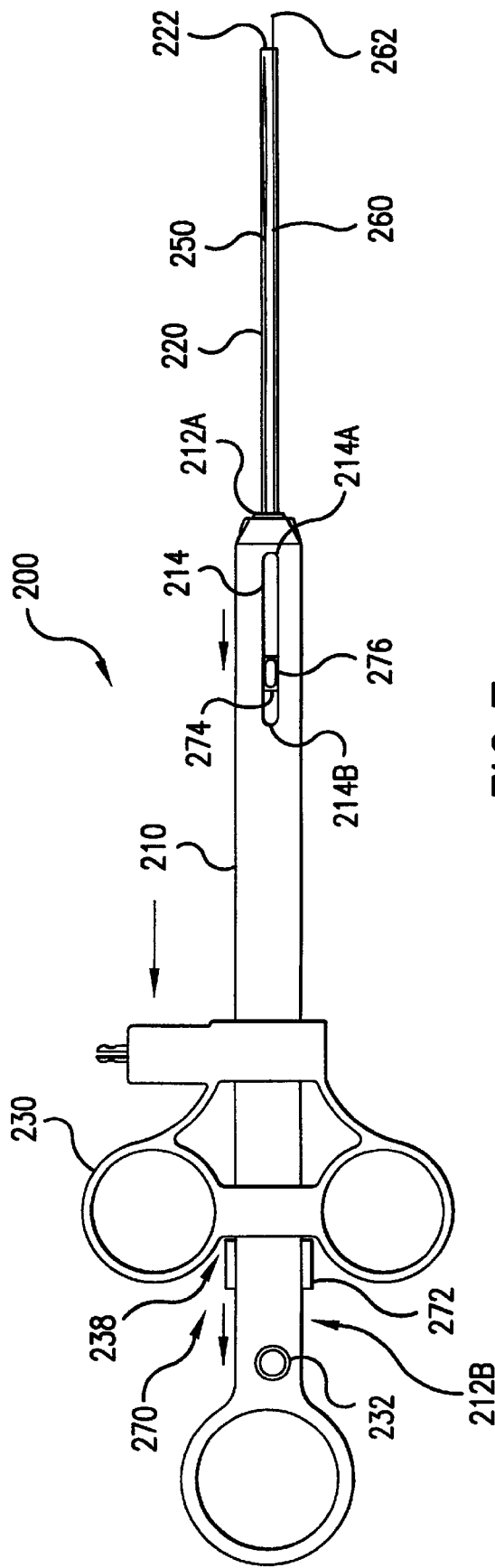
FIG. 7 is a side view of the surgical instrument of FIG. 5 with the needle exposed from the sheath.

FIG. 7 illustrates a configuration for the surgical instrument 200 where the needle 260 has been exposed from sheath 220. As can be seen, the distal end 262 of needle 260 extends beyond the distal end 222 of sheath 220. In order to extend distal end 262 of needle 260 from sheath 220, an operator moves sliding finger ring assembly 230 proximally along body 210 of the surgical instrument 200. Proximal motion of sliding finger ring assembly 230 will result in engagement of the finger ring assembly 230 with engagement head portion 272 of retraction member 270. As finger ring assembly 230 continues its movement proximally along body 210, finger ring assembly 230 will also move retraction member 270 proximally along body 210. Pressure applied by a user to move sliding finger ring assembly 230 proximally along body 210 will force retraction member 270 proximally along body 210 against the force applied by biasing member 280, which biases retraction member 270 in its first position. By moving retraction member 270 proximally along body 210, sheath attachment portion 274, which is connected to engagement head 272 of retraction member 270 through retraction connecting member 278, is also moved proximally within guide slot 214 of body 210. Since sheath 220 is rigidly attached to sheath attachment portion 274, proximal motion of sheath attachment portion 274 will retract sheath 220 a distance within body 210. Retraction of sheath 220 within body 210 will expose distal end 262 of needle 260 from the distal end 222 of sheath 220. Thus, through proximal motion of sliding finger ring assembly 230, retraction member 270 is moved proximally with respect to body 210 which in turn retracts sheath 220 into body 210. The retraction of sheath 220 within body 210 exposes the distal end 262 of needle 260 from the distal end 222 of sheath 220. Once the operator removes the force from sliding finger ring assembly 230 that moved the sliding finger ring assembly proximally along body 210, biasing member 280 biases retracting member 270 back to its first position which in-turn fully extends sheath 220 from body 210 which then positions the distal end 262 of needle 260 within sheath 220.

Figure 8:
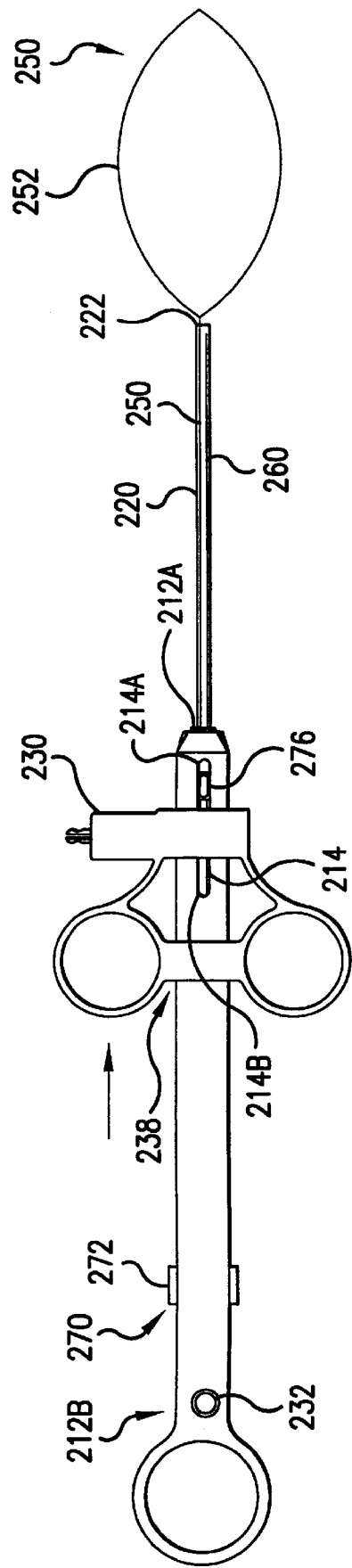
FIG. 8 is a side view of the surgical instrument of FIG. 5 with the snare loop exposed from the sheath.

As with the embodiment as described in FIGS. 1–4, the snare 250 of the embodiment of FIGS. 5–8 is operated independently of the needle 260. FIG. 5 illustrates a configuration for the surgical instrument 200 where the snare 250 is fully retracted within sheath 220. In this configuration, sliding finger ring assembly 230 is in a first position where the finger ring assembly 230 is disposed at the proximal end 212B of body 210. In order to extend a distal portion 252 of snare 250, which is the working portion of snare 250, from sheath 220, the operator would distally move sliding finger ring assembly 230 along body 210, as shown in FIG. 8. Because snare 250 is rigidly attached to sliding finger ring assembly 230, the distal movement of sliding finger ring assembly 230 will distally move snare 250 and will thus extend the distal portion 252 of snare 250 from sheath 220. Because apertures have been provided in snare attachment member 234, finger ring assembly ring 230 is able to slide along body 210 and not effect motion of needle 260.

Thus, the embodiment for the tool actuator assembly of FIGS. 5–8 provides for independent operation of the individual tools of the multi-function surgical instrument and an easily operable mechanism for the user for actuating each tool.

Figure 9:
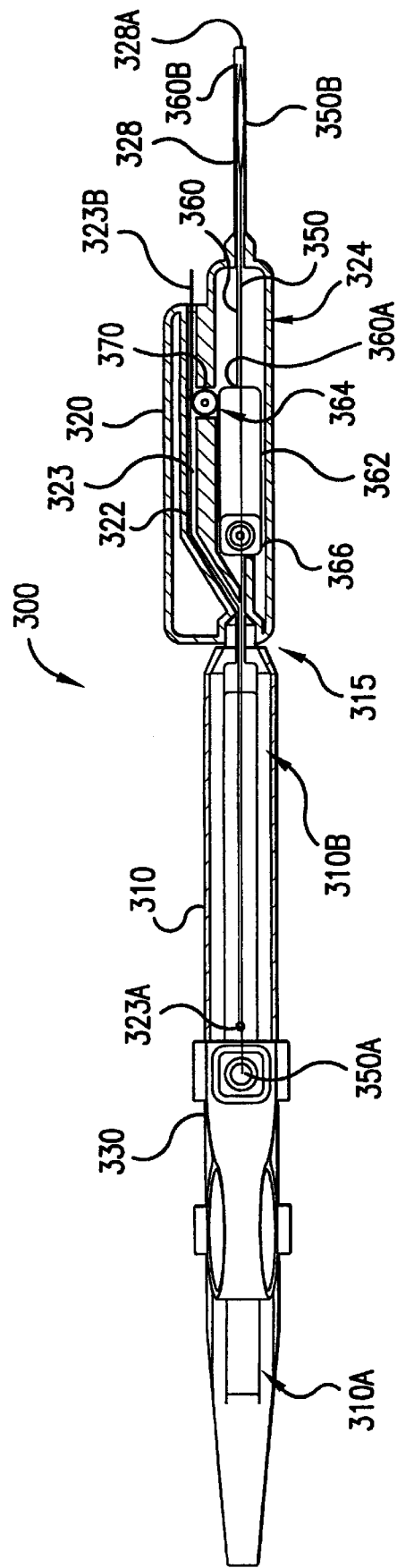
FIG. 9 is a top view of a multi-function surgical instrument that incorporates a third embodiment for the tool actuator assembly of the present invention.
Figure 10:
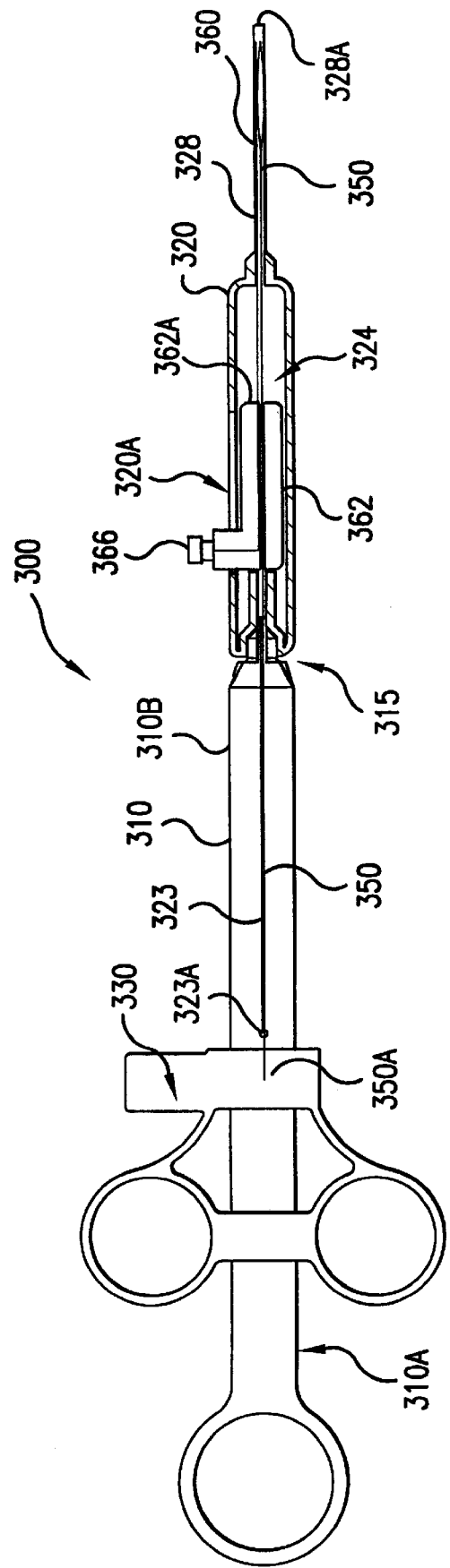
FIG. 10 is a side view of the multi-function surgical instrument of FIG. 9 with both the snare and the injection needle disposed within the sheath.

FIGS. 9–12 illustrate a third embodiment for the tool actuator assembly of the present invention. As can be seen in FIGS. 9 and 10, surgical instrument 300 includes a body portion 310, a housing 320, a first surgical tool 350, which is illustrated as a snare, and a second surgical instrument 360, which is illustrated as an injection needle. Arranged for sliding motion on body 310 is sliding finger ring assembly 330. Housing 320 can be either integrally formed with body portion 310 or can be detachably connected to body portion 310 such as by utilizing a threaded male/female connection such as illustrated with connection joint 315. Connection joint 315 is illustrated as including a threaded male portion that is disposed at a distal end 310B of body 310 which is received within an internally threaded female portion that is included in a proximal end of housing 320. However, as mentioned previously, the present invention is not limited to any particular configuration for joining housing portion 320 to body portion 310.

As is illustrated in FIG. 9, housing 320 includes a first channel 322 and a second channel 324. Disposed within first channel 322 is pulley cable 323 and disposed within second channel 324 is needle hub 362. Pulley cable 323 includes a gear tooth portion 323B and is rigidly attached to either sliding finger ring assembly 330 or snare 350 at its proximal end 323A. Proximal end 323A of pulley cable 323, as described above, can be rigidly attached to either sliding finger ring assembly 330 or to snare 350 and the present invention is not limited to any particular attachment point for proximal end 323A of pulley cable 323. The only requirement is that pulley cable 323 be attached either directly or indirectly to sliding finger ring assembly 330 such that as the sliding finger ring assembly 330 is moved distally along body portion 310 the pulley cable 323 is also moved distally. As will be further explained, gear teeth 323B of pulley cable 323 engage with gear 370. Pulley cable 323 is a rigid member such that as force is applied to pulley cable 323, the pulley cable moves as a rigid body in response to that application of force.

Disposed within second channel 324 is needle hub 362. Needle hub 362 includes gear teeth 364 which also engage with gear 370, as will be further explained. Injection needle 360 is rigidly attached to needle hub 362. Needle hub 362 is disposed for slidable motion within second channel 324. As can be seen, injection port 366 is also provided in needle hub 362. The purpose of injection port 366 is to be able to provide fluid that is to be injected into the body of a patient to needle 360. As can be seen in FIG. 10, a slot 320A is provided in housing 320 in order to permit needle hub 362 to slidably move within housing 320.

Second surgical tool 350, which is a snare device, is disposed within housing 320 and extends through body 310 where it is rigidly attached to sliding finger assembly 330. As such, snare 350 passes through slot 362A that is provided in needle hub 362. Slot 362A in needle hub 362 can be seen in FIG. 10. The distal portion 350B of snare 350 and 360B of needle 360 are disposed within sheath 328 when both tools are in a non-operative position.

Figure 11:
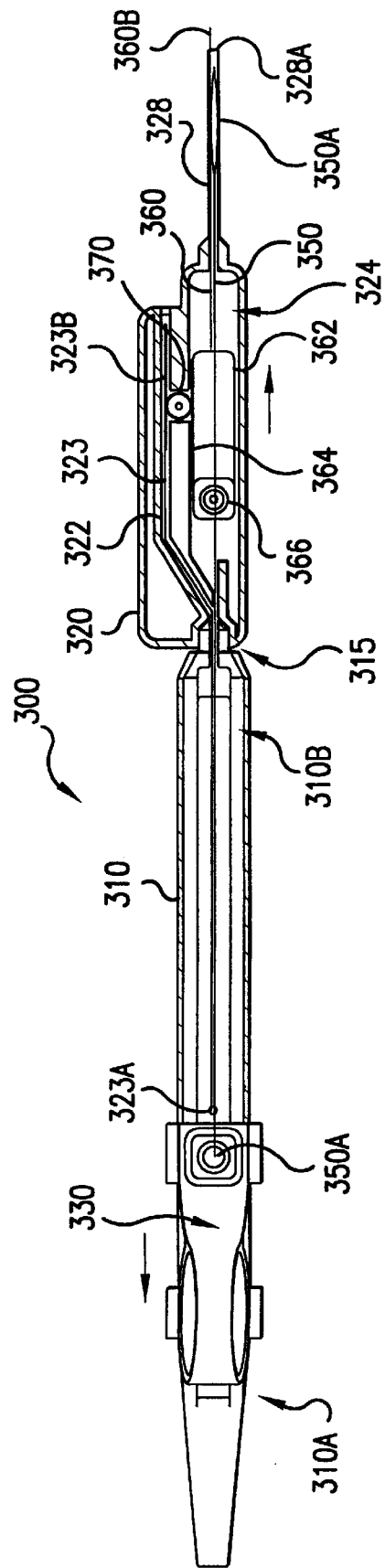
FIG. 11 is a top view of the multi-function surgical instrument of FIG. 9 with the injection needle exposed from the sheath.

The operation of the tool actuator assembly of the present invention as embodied in FIGS. 9–12 will now be described. FIGS. 9 and 10 illustrate the surgical instrument 300 in a configuration where both the snare 350 and the injection needle 360 are disposed completely within sheath 328 of the surgical instrument 300. FIG. 11 illustrates a configuration for surgical instrument 300 where needle 360 has been extended from sheath 328 of the surgical instrument 300. In order to extend needle 360 from distal end 328A of sheath 328, the operator slides finger ring assembly 330 proximally along body 310 to the proximal end 310A of body 310 as shown in FIG. 11. By sliding finger ring assembly 330 in a proximal direction, pulley cable 323 is also moved proximally since pulley cable 323 is rigidly connected, either directly or indirectly as described previously, to finger ring assembly 330. The proximal motion of pulley cable 323 causes engagement teeth 323B of pulley cable 323 to engage with gear 370. The proximal motion of gear teeth 323B causes gear 370 to rotate counter-clockwise within housing 320. As gear 370 rotates counter-clockwise, because gear 370 is also in engagement with gear teeth 364 that are included on needle hub 362, the counter-clockwise rotation of gear 370 will cause needle hub 362 to move in a distal direction within channel 324. Since needle 360 is rigidly attached to the distal end of needle hub 362, the distal motion of needle hub 362 within channel 324 will extend the distal end 360B of needle 360 from the distal end 328A of sheath 328. Thus, through proximal motion of finger ring assembly 330, the inter-action of pulley cable gear teeth 323B, gear 370, and gear teeth 364 of needle hub 362 will extend needle 360 from sheath 328.

To retract needle 360 back into sheath 328, the sliding finger ring assembly 330 is moved distally along body 310 to its original position as shown in FIGS. 9 and 10 where snare 350 is still retracted into sheath 328. When sliding finger ring assembly 330 is moved distally to this position, the pulley teeth 323B will engage with gear 370 to rotate gear 370 in a clockwise direction which in-turn will move needle hub 362 in a proximal direction which will retract needle 360 back into sheath 328.

Figure 12:
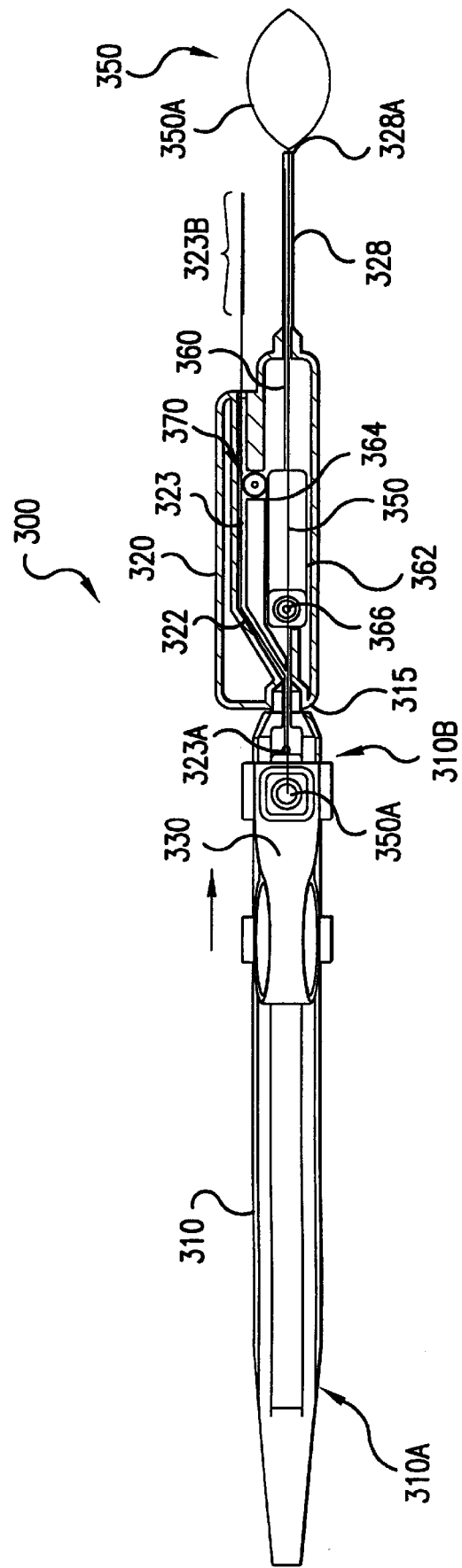
FIG. 12 is a top view of the multi-function surgical instrument of FIG. 9 with the snare exposed from the sheath.

FIG. 12 illustrates a configuration for surgical instrument 300 where snare 350 has been extended outside of sheath 328. In order to extend snare 350 from sheath 328, an operator will slide finger ring assembly 330 in a distal direction along body 310 beyond its position as illustrated in FIGS. 9 and 10. As is illustrated in FIG. 12, finger ring assembly 330 has been moved by an operator to the distal end 310B of body 310. The motion of finger ring assembly 330 distally along body 310 causes engagement teeth 323B of pulley cable 323 to extend distally beyond gear 370 and through an aperture that is provided in the distal end of housing 320. Thus, pulley cable 323 is no longer engaged with gear 370 and causes no rotation of gear 370. Since gear 370 is engaged with needle hub 362 and since gear 370 is not rotated by pulley cable 323 when finger ring assembly 330 has been moved distally along body 310, the needle hub 362, and consequently, needle 360, are not moved when the sliding finger ring 330 is moved distally along body member 310. However, since snare 350 is rigidly and directly attached to sliding finger ring assembly 330, the movement of finger ring assembly 330 in a distal direction along body 310 will also move snare 350 in a distal direction and will thus expose distal end 350A of the snare 350, which is the working end of the snare, from the distal end 328A of sheath 328. Thus, through movement of finger ring assembly 330 distally along body 310, snare 350 is exposed from sheath 328 of surgical instrument 300.

To retract snare 350 back into sheath 328, the operator slides finger ring assembly 330 proximally along body 310 to the position illustrated in FIGS. 9 and 10.

FIGS. 13–16 illustrate a fourth embodiment for the tool actuator assembly of the present invention. As will be seen, the actuating assembly of FIGS. 13–16 operates in a similar fashion to the actuating assembly that was disclosed in FIGS. 9–12, however, the configuration of the pulley cable and the engagement gear are modified in the embodiment of FIGS. 13–16. The configuration of the surgical instrument 400 with respect to the attachment of the snare and the needle assembly within the surgical tool are similar for the fourth embodiment of FIGS. 13–16.

Figure 13:
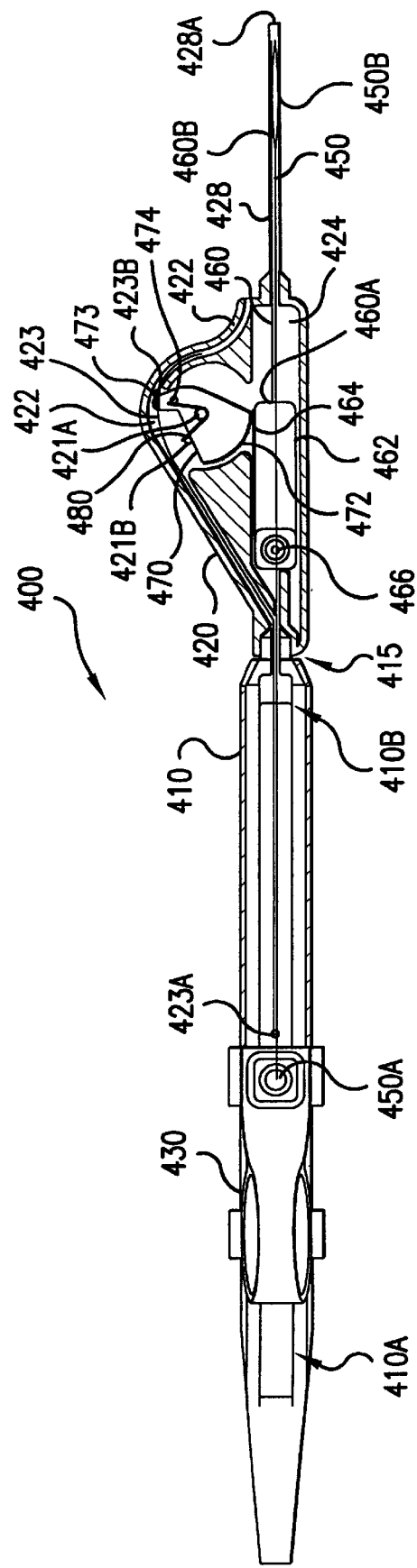
FIG. 13 is a top view of a multi-function surgical instrument that incorporates a fourth embodiment for the tool actuator assembly of the present invention.

As can be seen in FIG. 13, surgical instrument 400 again comprises a body portion 410 and a housing 420. Housing 420 is attached to body portion 410 through connection joint 415, which is similar to that as was described in the embodiment of FIGS. 9–12. Slidably mounted on body portion 410 is finger ring assembly 430. Housing 420 includes a first channel 422 and a second channel 424. Disposed within first channel 422 is pulley cable 423. Pulley cable 423 is rigidly attached, either directly or indirectly, to finger ring assembly 430 such that it moves in conjunction with finger ring assembly 430. Pulley cable 423 also includes a stop member 423B which is disposed at a distal end of pulley cable 423.

Disposed within second channel 424 is needle hub 462. Needle hub 462 includes engagement teeth 464 and injection port 466. Rigidly attached to needle hub 462 is injection needle 460. Injection needle 460 is rigidly attached to needle hub 462 at its proximal end 460A and the distal end 460B of needle 460 is disposed within sheath 428, which is included at the distal end of housing 420 when it is in a non-operative position. Snare 450 extends proximally through housing 420 and is rigidly attached at its proximal end 450A to sliding finger ring assembly 430. Snare 450 passes through housing 420 in channel 424 and thus needle hub 462 includes a slot 462A to permit snare 450 to pass through channel 424 without interfering with the movement of needle hub 462. Distal end 450B of snare 450 extends from distal end 428A of sheath 428 when it is in an operative position.

Also included in housing 420 is gear 470. In the embodiment of FIGS. 13–16, gear 470 is not configured as a circular gear as was the gear in the embodiment of FIGS. 9–12. However, the function of gear 470 is similar to the function that was performed by the gear of FIGS. 9–12. Gear 470 is mounted on pin 421A that is disposed within housing 420. As such, gear 470 is able to rotate about pin 421A. Gear 470 includes engagement teeth 472 which cooperate with engagement teeth 464 that are included on needle hub 462. Gear 470 also includes a channel 473 through which passes pulley cable 423. Stop member 423B of pulley cable 423 is disposed on the distal side of the channel 473 that is within gear 470. As such, pulley cable 423 is not able to be retracted fully through channel 473. Pulley cable 423 will be prevented from being retracted completely through gear 470 by the interaction of stop member 423B with the structure of gear 470 that defines channel 473.

Also included on gear 470 is pin 474. As will be explained, pin 474 cooperates with biasing member 480. As will be further explained, biasing member 480 cooperates with pin 474 and pin 421B, which is disposed within housing 420, to bias gear 470 into a first position where needle 460 is retracted within sheath 428.

Figure 14:
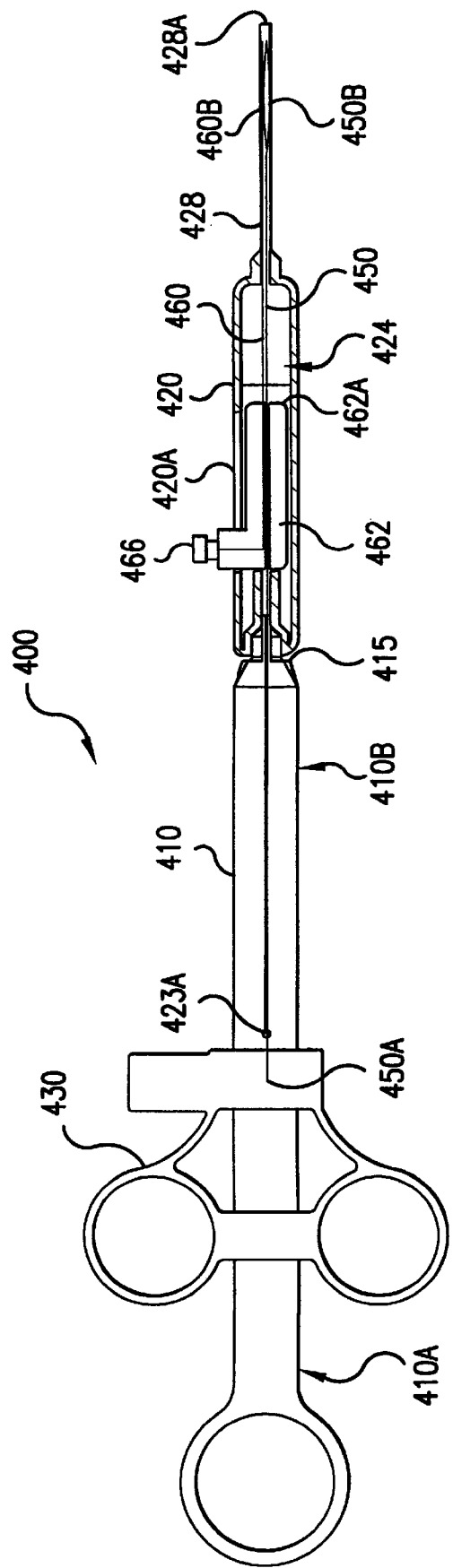
FIG. 14 is a side view of the multi-function surgical instrument of FIG. 13 with both the snare and the injection needle disposed within the sheath.
Figure 15:
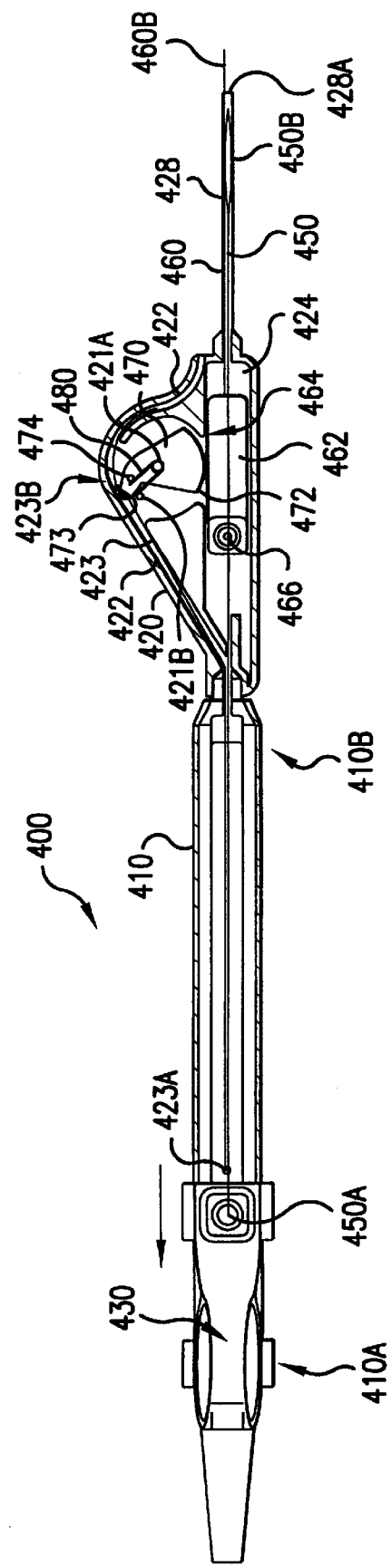
FIG. 15 is a top view of the multi-function surgical instrument of FIG. 13 with the injection needle exposed from the sheath.

The operation of the tool actuator assembly for the embodiment of FIGS. 13–16 will now be described. FIGS. 13 and 14 show a configuration for surgical instrument 400 where both the needle 460 and the snare 450 are fully retracted within sheath 428. FIG. 15 illustrates a configuration for the surgical tool 400 where injection needle 460 has been extended from sheath 428.

In order to extend needle 460 out through sheath 428, the operator slides finger ring assembly 430 proximally along body 410 to a position as shown in FIG. 15. Again, because pulley cable 423 is rigidly attached to finger ring assembly 430, either directly or indirectly, the proximal movement of finger ring assembly 430 along body 410 will also proximally move pulley cable 423. When pulley cable 423 is moved proximally, stop member 423B will engage with gear 470 and will pivot gear 470 in a counterclockwise direction about pivot pin 421A. Because stop member 423B is sized such that it can not pass completely through channel 473 that is formed within gear 470, the proximal motion of pulley cable 423 will rotate gear 470 counter-clockwise because of the interaction of stop member 423B and the structure defining the channel 473. The sliding finger ring assembly 430 must be moved proximally along body 410 with sufficient force such that gear 470 can be rotated counter-clockwise against the biasing force that is applied to gear 470 by biasing member 480. As gear 470 is rotated counter-clockwise about pivot pin 421A, engaging teeth 472 of gear 470 will engage with teeth 464 of needle hub 462. As gear 470 continues to rotate in a counterclockwise direction the interaction of gear teeth 472 with gear teeth 464 will move needle hub 462 in a distal direction within channel 424 of housing 420. Because needle 460 is rigidly attached to needle hub 462, the distal motion of needle hub 462 will also distally move the distal end 460B of needle 460 within sheath 428 and thus extend distal end 460B of needle 460 beyond distal end 428A of sheath 428.

When the operator discontinues applying force to finger ring assembly 430, the biasing member 480 will act to rotate gear 470 in a clockwise direction which in-turn will move hub 462 proximally within channel 424 in housing 420. Thus, when the operator releases the force on finger ring assembly 430, the injection needle is automatically retracted within sheath 428 due to the biasing member 480 acting upon gear 470 to rotate the gear back in a clockwise direction. The clockwise rotation of gear 470 proximally moves needle hub 462 within channel 424 thus retracting needle 460 within sheath 428.

Figure 16:
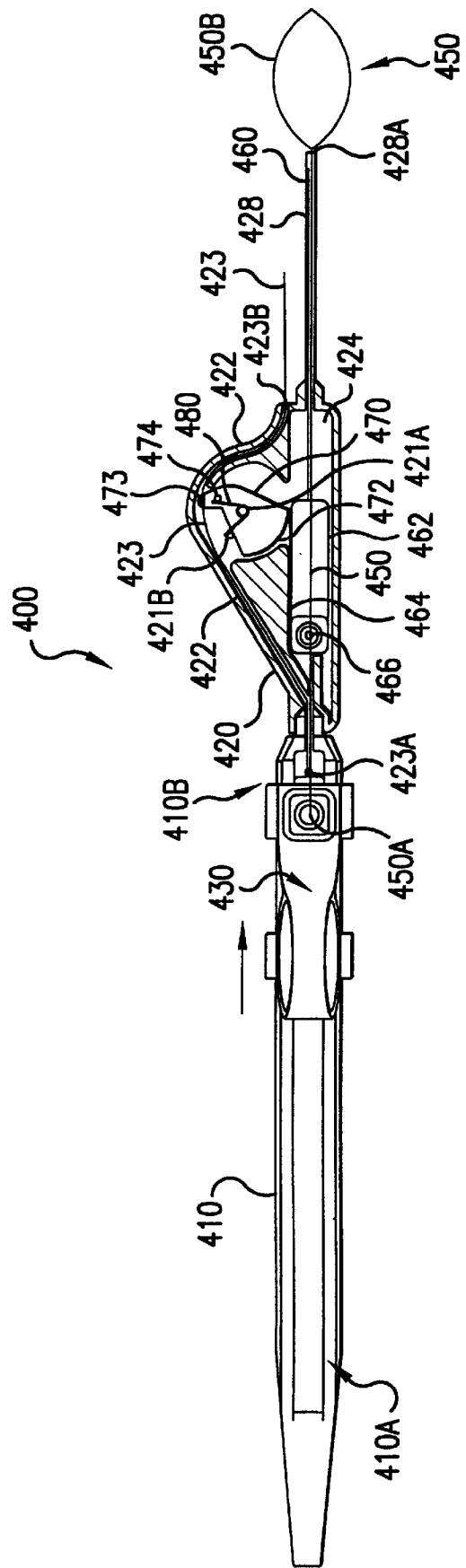
FIG. 16 is a top view of the multi-function surgical instrument of FIG. 13 with the snare exposed from the sheath.

FIG. 16 illustrates a configuration for surgical instrument 400 where snare 450 has been exposed from sheath 428. In order to extend snare 450 from sheath 428, the operator will slidably move finger ring assembly 430 along body 410 in a distal direction. FIG. 16 illustrates sliding finger ring assembly 430 after it has been moved to the distal end 410B of body 410. When finger ring assembly 430 is moved distally along body 410, pulley cable 423 passes through channel 473 that is provided in gear 470. Stop member 423B passes through a distal portion of channel 422 in housing 420 and the distal-most portion of pulley cable 423 extends out through an aperture in housing 420 that is located in the distal portion of housing 420. Thus, there is no interaction between pulley cable 423 and gear 470. Pulley cable 423 merely passes through gear 470. Therefore, distal motion of finger ring assembly 430 does not result in any rotation of gear 470. However, because snare 450 is rigidly attached to sliding finger ring assembly 430, as sliding finger ring assembly 430 is moved distally, the snare is also moved distally such that it is extended from the distal end 428A of sheath 428. Because slot 462A has been provided in needle hub 462, snare 450 is able to pass by and through needle hub 462 without causing any movement of needle hub 462 within channel 424. As such, FIG. 16 illustrates a configuration where a distal end 450B of snare 450, which is the working end of snare 450, has been extended from sheath 428.

To retract snare 450 back into sheath 428, the operator slides finger ring assembly 430 proximally along body 410 to the position illustrated in FIGS. 13 and 14.

Figure 17:
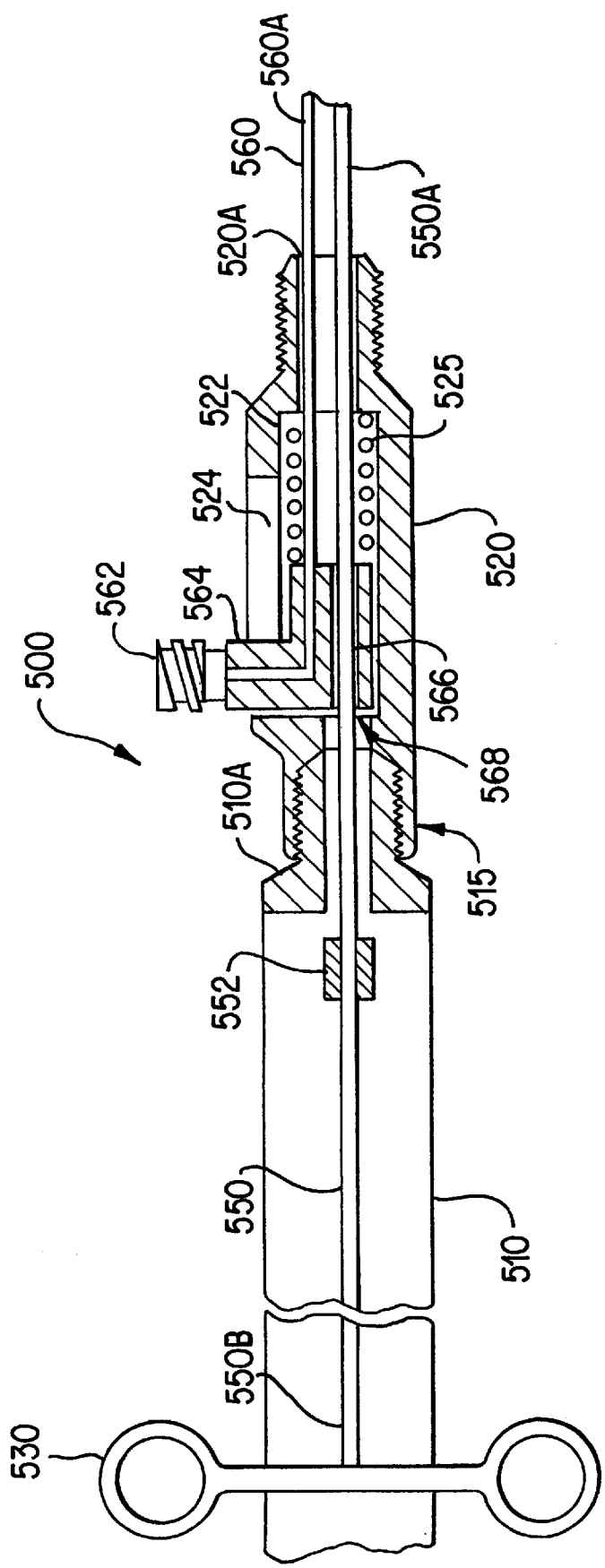
FIG. 17 is a side view of a multi-function surgical instrument that incorporates a fifth embodiment for the tool actuator assembly of the present invention.

FIG. 17 illustrates a fifth embodiment for a tool actuator assembly in accordance with the principles of the present invention. As can be seen, surgical instrument 500 includes a body portion 510 and a housing 520. Body portion 510 is a hollow cylindrical member that includes a first surgical tool 550 within it. For purposes of illustration, first surgical tool 550 will be discussed as a snare, however, first surgical tool 550 may be any of a variety of different surgical tools. Slidably disposed on body 510 is finger ring assembly 530. Finger ring assembly 530 is disposed on body 510 such that it is able to move proximally and distally along body 510. Snare 550 is rigidly attached to finger ring assembly 530 at a proximal end 550B of snare 550. Thus, as sliding finger ring assembly 530 is moved along body 510, snare 550 is also moved within body 510. Attached to snare 550 is coupler 552. Coupler 552 is rigidly attached to snare 550 and is disposed within body 510. A distal end 510A of body 510 includes a male threaded portion such that it is able to be joined to housing 520 which includes an internally threaded female portion. Body 510 is joined to housing 520 at connection joint 515.

Housing 520 includes a second surgical tool assembly, which for purposes of illustration will be discussed as injection needle 560. As can be seen in FIG. 17, housing 520 includes needle hub assembly 564 and needle 560, which is connected to needle hub assembly 564. Injection port 562 is provided on needle hub assembly 564 in order to provide a fluid to injection needle 560 for injection into the body of a patient, in accordance with well-known principles. Needle hub 564 is disposed within channel 522 which is formed within housing 520. Thus, needle hub 564 is able to move both distally and proximally within housing 520. Slot 524 is provided in housing 520 to permit injection port 562 to extend up through housing 520 and permit injection port 562 to be able to be moved along with needle hub 564 within housing 520.

Also provided within housing 520 is biasing member 525. Biasing member 525 is disposed in a distal end of channel 522 and biases needle hub 564 in a proximal direction within housing 520. With needle hub 564 biased proximally within housing 520, distal end 560A of needle 560 does not extend beyond a distal portion of a sheath (not shown in FIG. 17) which is attached to the distal-most end 520A of housing 520 and which contains the distal portions of both needle 560 and snare 550 within it when both tools are in a retracted position.

Thus, as can be seen in FIG. 17, housing 520, which includes a needle assembly, provides the capability to reconfigure a known snare tool assembly such that it is able to have the additional functionality of an injection capability without requiring modification of the snare assembly itself. Housing 520 is merely attached to the snare instrument without requiring modification of the snare instrument. The operation of the multi-function surgical instrument 500 will be explained below.

In order to extend snare 550 from a sheath that is attached to housing 520 and which encloses snare 550, the operator would slide finger ring assembly 530 in a distal direction along body 510. Distal movement of finger ring assembly 530 will move distal end 550A distally within the sheath such that the distal end 550A of snare 550 will extend from the distal end of the sheath. Thus, distal motion of finger ring assembly 530 extends snare 550 from the sheath of the surgical instrument 500. A slot 566 is provided in needle hub 564 in order to permit snare 550 to move within housing 520 without being impeded by needle hub 564. As will be explained, the distal movement of snare 550 will also extend needle 560 from the sheath. Thus, both snare 550 and needle 560 are extended from the sheath of surgical instrument 500 by the movement of finger ring assembly 530 distally along body 510.

As snare 550 is moved distally within body 510, coupler 552, which is rigidly attached to snare 550 within body 510, also is moved distally within body 510. As snare 550 continues to move distally within body 510, coupler 552 will exit through an aperture included in the distal end 510A of body 510. As coupler 552 exits the distal end 510A of body 510, it will enter the proximal end of housing 520. As coupler 552 enters the proximal end of housing 520, it will engage with the proximal structure 568 of needle hub 564. Because coupler 552 is formed such that it is larger in size than channel 566 that has been formed in needle hub 564, it will not merely pass by hub 564 through channel 566, but rather will than engage the structure 568 at the proximal end of needle hub 564. The engagement between coupler 552 and needle hub 564 will move needle hub 564 distally within housing 520 as coupler 552 continues its distal movement along with snare 550. Sufficient force must be applied to snare 550, and thus coupler 552, such that it can move needle hub 564 distally within housing 520 against the biasing force that is applied by biasing member 525. As needle hub 564 moves distally within housing 520, needle 560, which is attached to needle hub 564, also moves distally with respect to housing 520. This distal movement of needle 560 will cause the distal end 560A of needle 560 to extend from a distal end of the sheath that encloses the needle. Thus, in this manner, the distal motion of snare 550 also causes distal motion of needle 560, resulting in extension of both snare 550 and needle 560 from surgical instrument 500.

In order to retract snare 550 and needle 560 back into the sheath of the surgical instrument 500, a user would move finger ring assembly 530 in a proximal direction along body 510. Proximal motion of finger ring assembly 530 along body 510 will also move snare 550 in a proximal direction with respect to body 510. Continued proximal motion of snare 550 will result in distal end 550A of snare 550 being retracted within the sheath of the surgical instrument 500. As snare 550 is moved proximally within surgical instrument 500, forward pressure will no longer be applied to needle hub 564 by coupler 552. As the forward pressure is removed from needle hub 564, biasing member 525 will force needle hub 564 to move proximally within channel 522 in housing 520. The proximal movement of needle hub 564 within channel 522 under the biasing force of biasing member 525 will retract the distal end 560A of needle 560 within the sheath of the surgical instrument 500.

Figure 18:
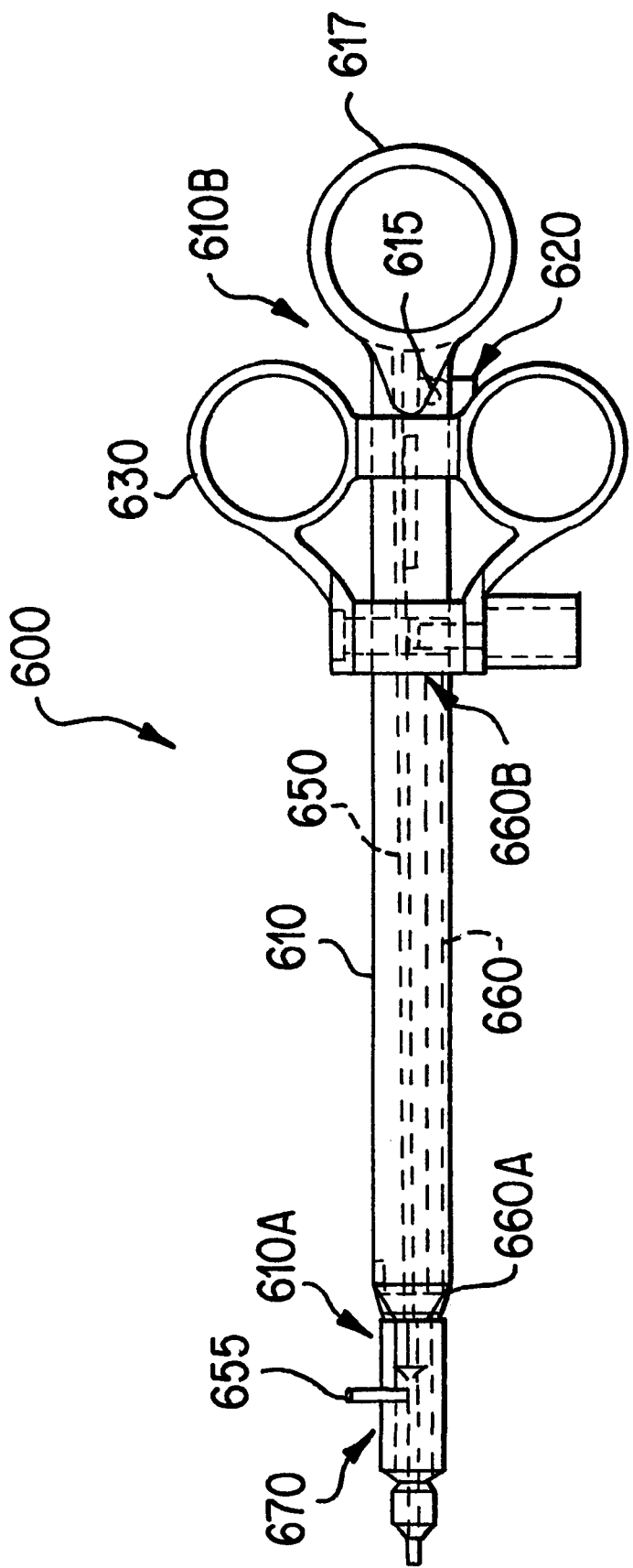
FIG. 18 is a side view of a multi-function surgical instrument that incorporates a sixth embodiment for the tool actuator assembly of the present invention.

FIGS. 18–24 illustrate a sixth embodiment for a tool actuator assembly in accordance with the present invention. As can be seen in FIG. 18, surgical instrument 600 includes a first tool 650 (shown in phantom), which is disclosed as an injection needle, and a second tool 660 (also shown in phantom), which is disclosed as a snare. Again, as with the other embodiments that have been previously discussed, the first and second tools can be any of a variety of tools and the present invention as embodied in FIGS. 18–24 is not limited to an embodiment where the surgical tools are a needle and a snare. As can be seen in FIG. 18, surgical instrument 600 includes a body portion 610, a finger ring assembly 630 slidably mounted on body 610 for movement in both a proximal and distal direction on body 610, a tool actuating member 620, and an injection adaptor port 670. Second tool 660 is attached to finger ring assembly 630 and thus its movement is controlled by finger ring assembly 630. Distal movement of finger ring assembly 630 toward distal end 610A of body 610 will result in the distal end 660A, which would include a snare loop (not shown), of second tool 660 being extended from distal end 610A of body 610. Likewise, proximal motion of finger ring assembly 630 toward proximal end 610B of body 610 will retract distal end 660A of second tool 660 within distal end 610A of body 610.

The actuation of needle 650 is controlled by interaction of finger ring assembly 630 and tool actuating member 620, as will be explained further. Tool actuating member 620 is pivotally attached to body 610 at the proximal end 610B of body 610. Proximal end 610B of body 610 includes a pivot pin 615 that is rigidly attached to body 610. Tool actuating member 620 is pivotally mounted on pivot pin 615. Needle 650 is disposed within body 610 of surgical instrument 600 and a proximal portion 650B of needle 650 is rigidly attached to tool actuating member 620. Tool actuating member 620 includes a needle attachment portion 622. Needle proximal portion 650B is attached to needle attachment portion 622 of tool actuating member 620.

Figure 19:
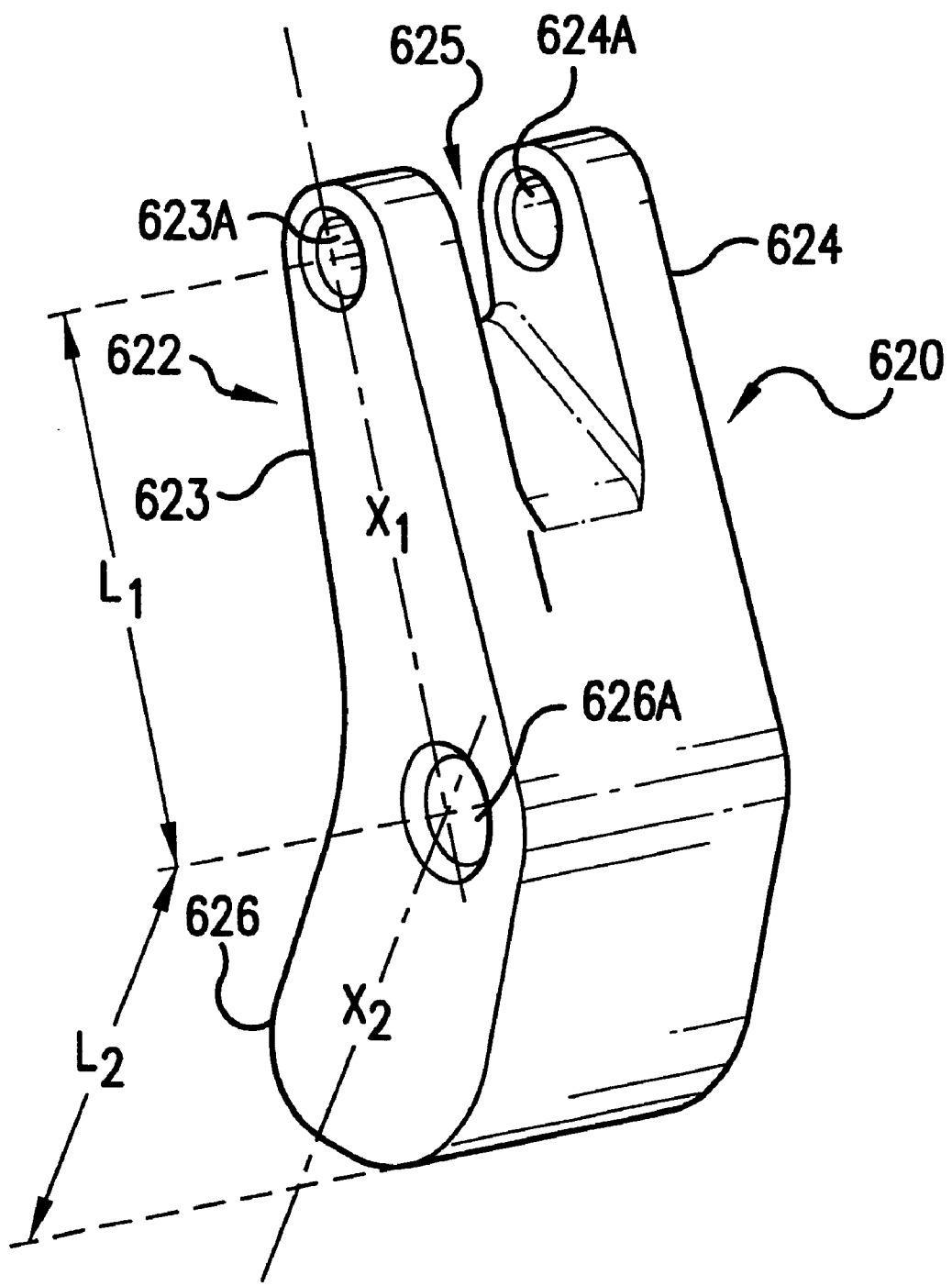
FIG. 19 illustrates the tool actuating member of the embodiment of FIG. 18.

In further describing tool actuating member 620, FIG. 19 illustrates the tool actuating member. As can be seen, tool actuating member 620 includes a needle attachment portion 622 and an engagement portion 626. Needle attachment portion 622 is comprised of a first arm member 623 and a second arm member 624. A slot 625 is defined by first arm 623 and second arm 624. Included in arm 623 is aperture 623A and included in arm 624 is aperture 624A. An attachment pin 629 (visible in FIG. 21 but not shown in FIG. 19) is utilized to attach needle 650 to actuating member 620. Needle proximal portion 650B is received within slot 625. Needle proximal portion 650B includes an aperture that also receives attachment pin 629 within it. The aperture that is defined by needle proximal portion 650B is aligned with aperture 623A and 624A in needle attachment portion 622. Attachment pin 629 is positioned through aperture 623A, the aperture defined by needle proximal end 650B, and aperture 624A. Thus, needle 650 is attached to needle attachment portion 622.

Engagement portion 626 of tool actuating member 620 defines aperture 626A. Aperture 626A receives pivot pin 615, which is attached to body 610, within it. Thus, tool actuating member 620 is able to be pivotally mounted to body 610 through pivot pin 615 being received within aperture 626A. As can be seen in FIG. 19, the longitudinal axis $X_1$ of needle attachment portion 622 is off-set from the longitudinal axis $X_2$ of engagement portion 626. Additionally, the length $L_1$ of needle attachment portion 622 is greater than the length $L_2$ of engagement portion 626. The purposes of the axis off-set and the length difference between needle attachment portion 622 and engagement portion 626 will become clear upon describing the operation of tool actuating member 620.

Figure 20:
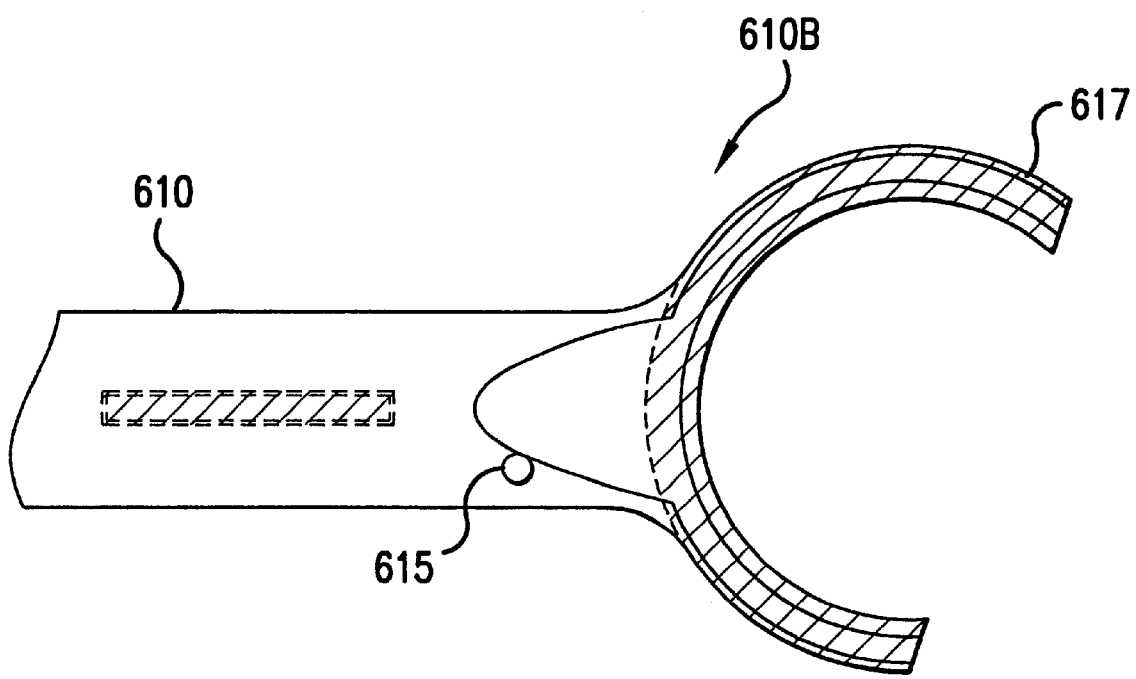
FIG. 20 illustrates the proximal end of the surgical instrument of FIG. 18.

The proximal end 610B of body 610 of surgical instrument 600 is illustrated in FIG. 20. As can be seen, the proximal end 610B of body 610 includes pivot pin 615. As was mentioned previously, pivot pin 615 is received within aperture 626A of tool actuating member 620 to pivotally mount actuating member 620 onto body 610. Proximal end 610B of body 610 also includes thumb ring 617.

Figure 21:
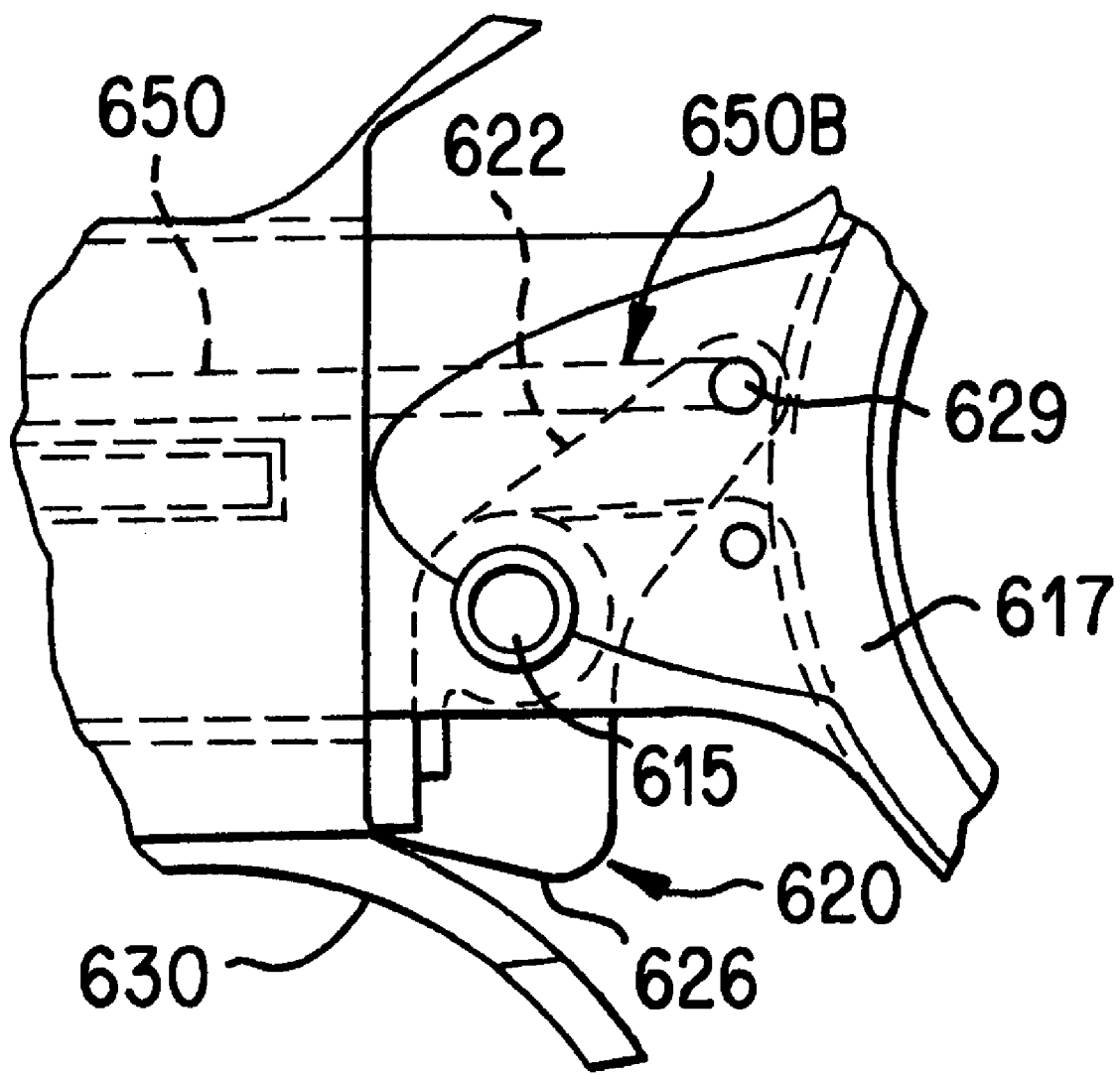
FIG. 21 illustrates the tool actuator member of the embodiment of FIG. 18 in a first position where a distal end of an injection needle is not in an operative position.

In describing the operation of tool actuating member 620, FIG. 18 illustrates tool actuating member 620 in a first position where distal end 650A of needle 650 is retracted within surgical instrument 600. A more detailed view of the tool actuating member 620 in this first position can be seen in FIG. 21. As can be seen in FIG. 21, needle attachment portion 622 is located proximally with respect to body 610. Thus, because needle 650 is attached to actuating member 620 on needle attachment portion 622, needle 650 has been moved proximally with respect to body 610 of surgical instrument 600. As can be further seen in FIG. 21, finger ring assembly 630 is positioned adjacent to engagement portion 626 of tool actuating member 620, but has not as of yet exerted any force upon engagement portion 626.

Figure 22:
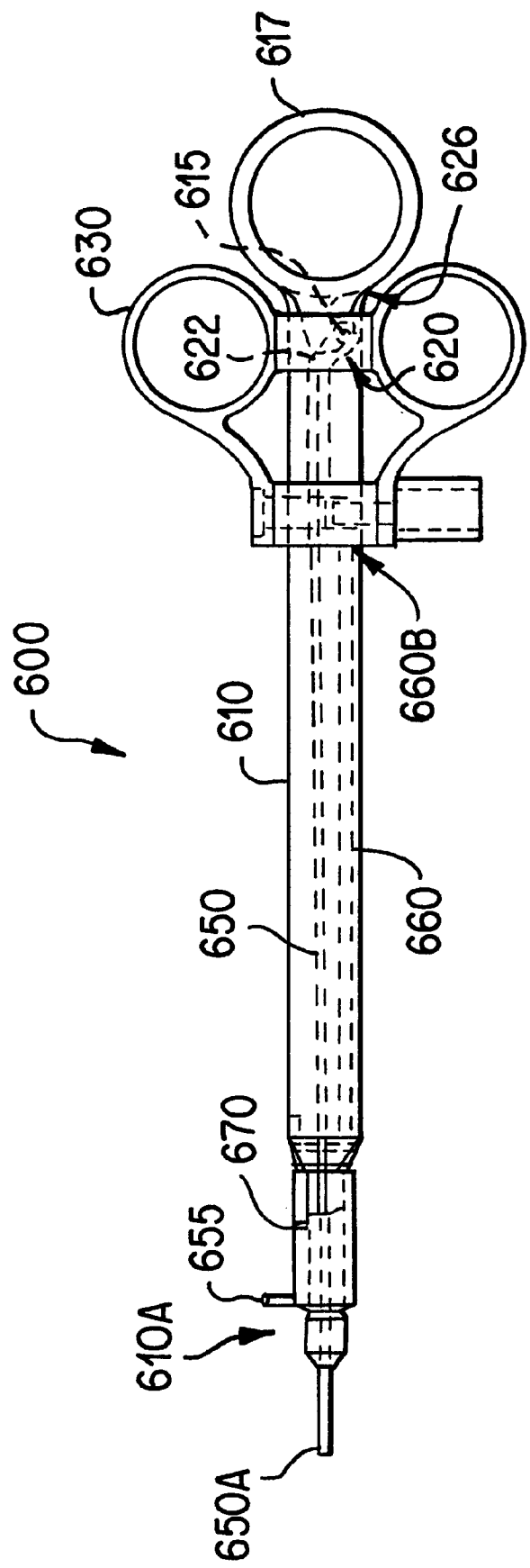
FIG. 22 illustrates the tool actuator member of the embodiment of FIG. 18 in a second position where the distal end of the injection needle has been extended from the surgical instrument.
Figure 23:
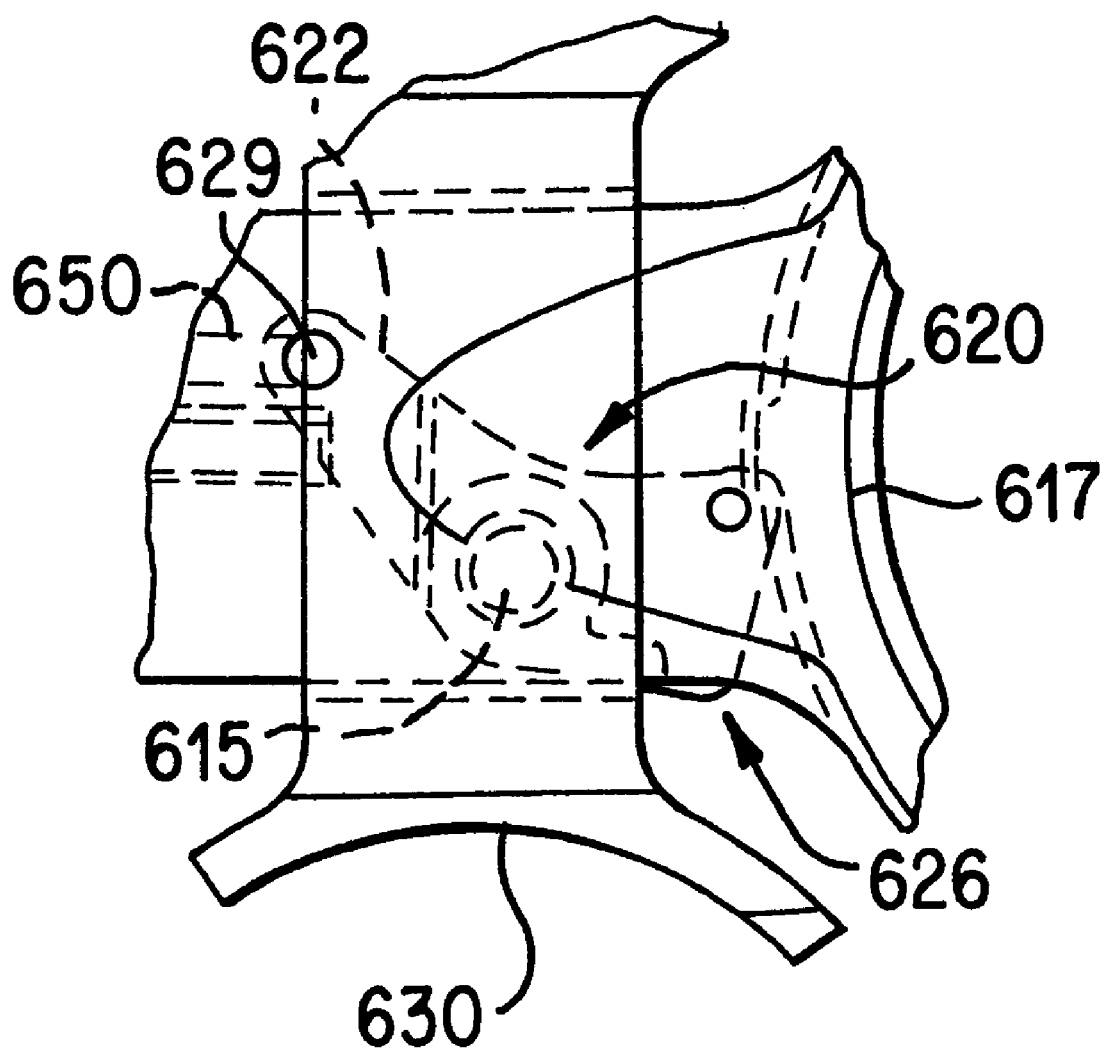
FIG. 23 illustrates the tool actuator member of the embodiment of FIG. 18 in its second position.

FIG. 22 illustrates actuating member 620 after it has been pivoted to its second position, which in-turn has extended distal end 650A of needle 650 from distal end 610A of body 610. A more detailed view for the positioning of actuating member 620 in its second position where needle 650 has been extended from surgical instrument 600 can be seen in FIG. 23. As seen in FIG. 23, finger ring assembly 630 has been moved proximally along body 610 such that the structure of finger ring assembly 630 has engaged with engagement portion 626 of actuating member 620. As finger ring assembly 630 continues its movement proximally along body 610, the force that is applied to engagement portion 626 of actuating member 620 causes actuating member 620 to pivot counter-clockwise about pivot pin 615. This pivotal motion of actuating member 620 on pivot pin 615 causes needle attachment portion 622 to move distally with respect to body 610. Distal motion of needle attachment portion 622 results in distal motion of needle 650 within body 610. The rotation of actuating member 620 about pivot pin 615 is sufficient to distally move attachment portion 622 such that distal end 650A of needle 650 is extended beyond distal portion 610A of body 610. Thus, the distal end 650A of needle 650 is exposed from surgical instrument 600 such that it may inject fluid into the body of a patient.

As was explained earlier, the longitudinal axis of attachment portion 622 is off-set from the longitudinal axis of engagement portion 626. Additionally, the length of needle attachment portion 622 is greater than the length of engagement portion 626. These differences between the two portions of actuating member 620 results in a mechanical advantage for moving needle 650 distally within body 610 by pivoting actuating member 620. In other words, proximal movement of engagement portion 626 of actuating member 620, caused by counter-clockwise rotation of the actuating member 620 through interaction with a proximally moving sliding finger ring assembly 630, will result in a greater length of distal movement of needle attachment portion 622 of tool actuating member 620. Thus, a relatively small movement of finger ring assembly 630 in a proximal direction will result in a significantly greater movement of needle 650 in a distal direction.

Once the needle has been utilized to injection fluid into a patient, surgical instrument 600 can be removed from the patient and needle 650 can be retracted within surgical instrument 600 through manual rotation of actuating member 620 by the user of the instrument. Retraction of the needle 650 within surgical instrument 600 is not as critical an operation as extension of the needle because the process of extending the needle occurs while the instrument is within a patient and thus efficient movement of the needle while the instrument is in the patient is important. Conversely, after the needle has been utilized to inject fluid into the patient, the surgical instrument can be removed from the patient and the needle can be manually retracted into the instrument by the surgeon after the procedure has been performed.

Figure 24:
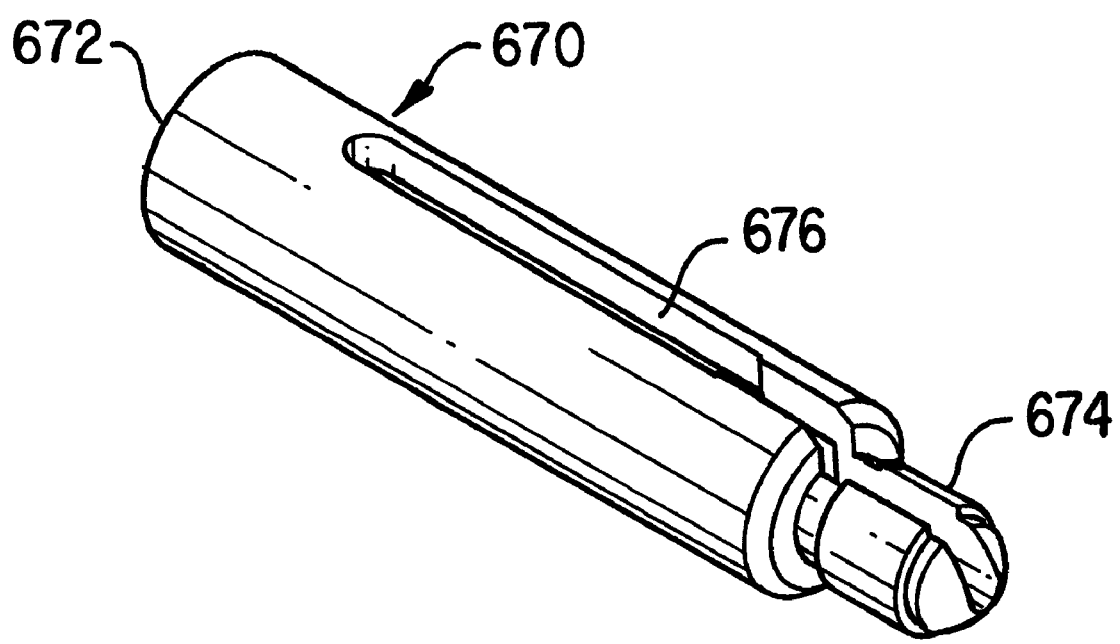
FIG. 24 illustrates an injector adaptor port that can be utilized with the multifunction surgical instrument of FIG. 18.

FIG. 24 illustrates an injection adaptor port 670 that can be utilized with the embodiment for the surgical instrument as disclosed in FIGS. 18–24. Injection adaptor port 670 includes an attachment portion 672 that is utilized to attach the injection adaptor port 670 to body 610 of surgical instrument 600. Injection adaptor port 670 may include internal threading at attachment portion 672 that can cooperate with an externally threaded male portion included at the distal end of body 610 in order to attach injection adaptor port 670 to body 610. Distal end 674 of injection adaptor port 670 includes an aperture such that distal end 650A of injection needle 650 is able to extend out through the injector adaptor port 670. Injector adaptor port 670 defines a slot 676 that extends from attachment portion 672 to distal end 674. Received within slot 676 is injection port 655 that is included at the distal end 650A of injection needle 650.

Figure 25:
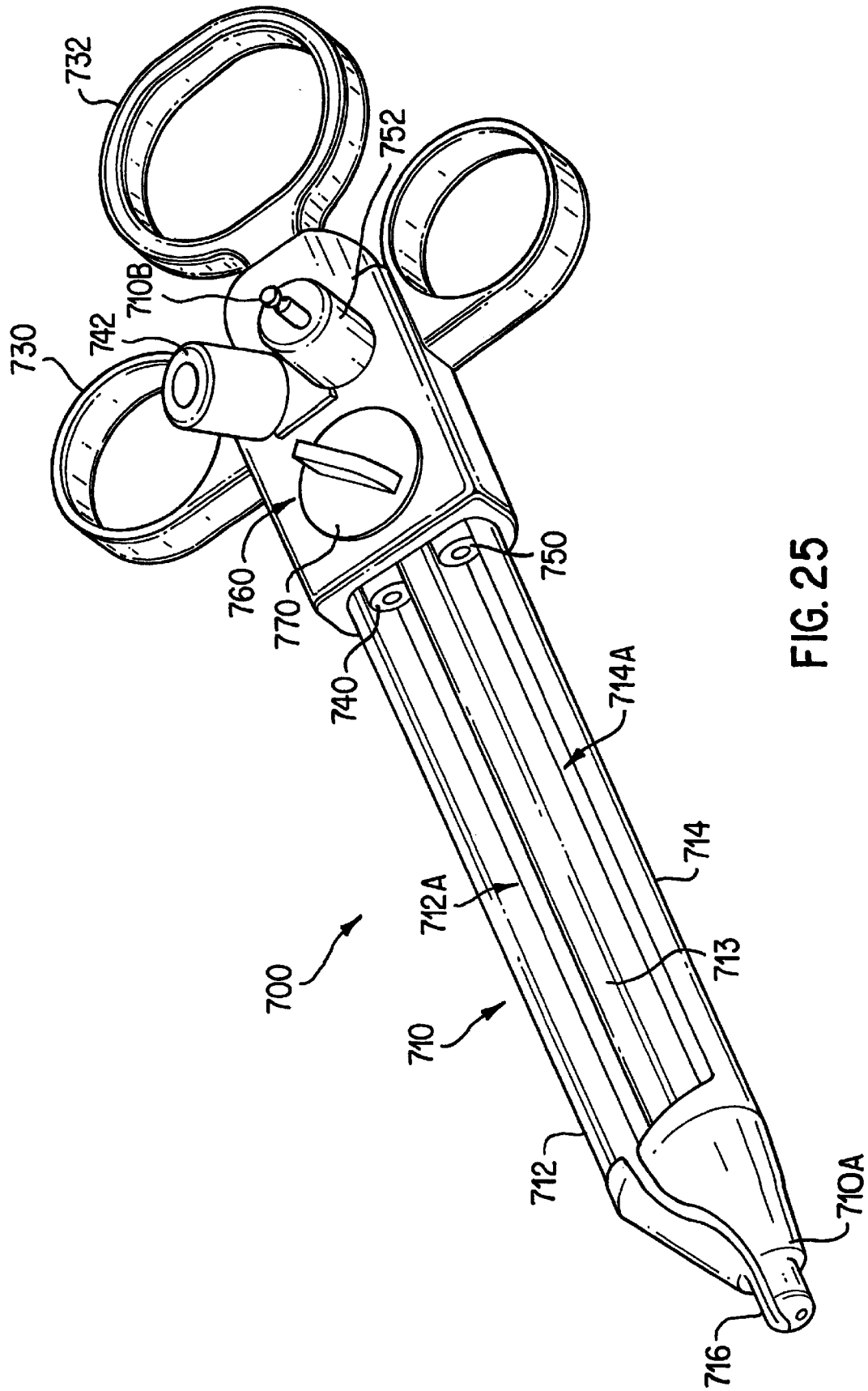
FIG. 25 is a perspective view of a multi-function surgical instrument that incorporates a seventh embodiment for the tool actuator assembly of the present invention.
Figure 26:
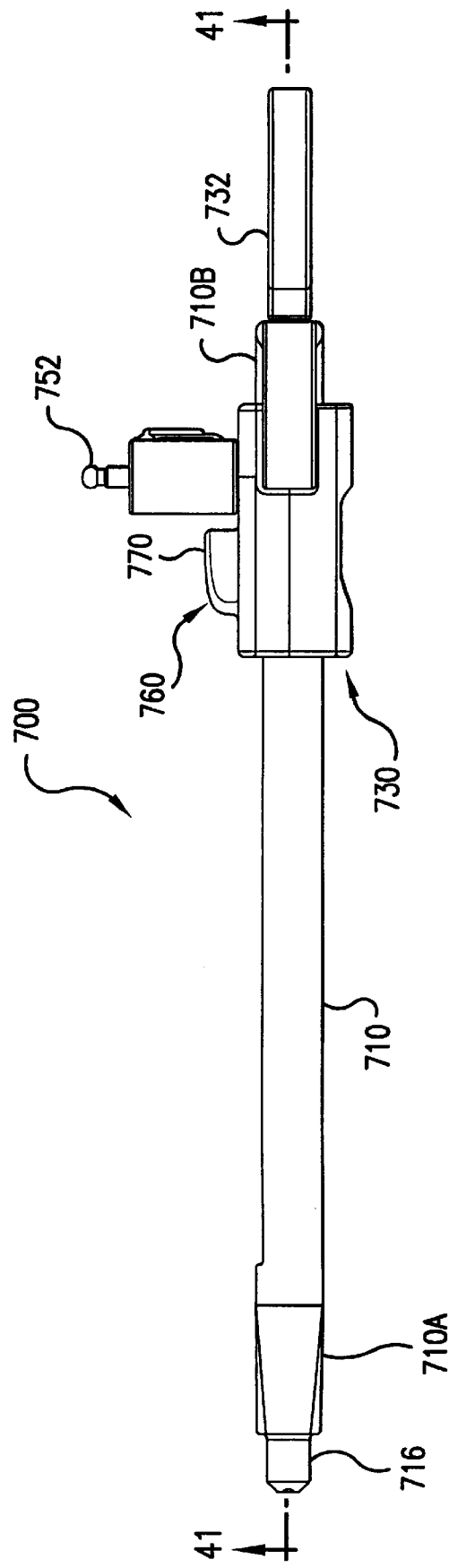
FIG. 26 is a side view of the multi-function surgical instrument of FIG. 25.

FIGS. 25–41 illustrate a seventh embodiment for a tool actuator assembly in accordance with the present invention. As can be seen in FIGS. 25 and 26, surgical instrument 700 is comprised of a body portion 710, a sliding finger ring assembly 730, a tool selection and locking switch 760, and first and second instrument hubs 740 and 750, respectively. A first surgical tool (not shown in FIGS. 25 and 26) would be associated with first instrument hub 740 and a second surgical tool (also not shown in FIGS. 25 and 26) would be associated with second instrument hub 750. As will be explained, a surgeon utilizing surgical instrument 700 would select between using the first surgical tool and the second surgical tool by selectively engaging either the first instrument hub 740 or the second instrument hub 750 with tool selection and locking switch 760. The embodiment of FIGS. 25–41 for the surgical instrument 700 is not limited to any particular tools that may be incorporated into the instrument. However, for purposes of illustration, it will be described that first instrument hub 740 is associated with an injection needle and second instrument 750 is associated with a snare device.

In further describing surgical instrument 700, as can be seen in FIGS. 25 and 26, surgical instrument 700 is comprised of a body portion 710. Body portion 710 is comprised of a central hub 713, an outer frame member 712, and an outer frame member 714. Central hub 713 and outer frame member 712 define a first channel 712A and central hub 713 and outer frame member 714 define a second channel 714A. Located at a distal end 710A of body portion 710 is sheath attachment portion 716. Sheath attachment portion 716 provides for attachment of a catheter or similar structure to body portion 710 through which the surgical tools that are associated with the surgical instrument 700 would extend from body portion 710.

Sliding finger ring assembly 730 is slidably mounted onto body portion 710. Sliding finger ring assembly 730 is operably associated with tool selection and locking switch 760 and the first and second instrument hubs 740, 750, respectively, as will be explained later in this specification. First instrument hub 740 is mounted for slidable motion with respect to body portion 710 within first channel 712A and second instrument hub 750 is likewise mounted for slidable motion with respect to body portion 710 within second channel 714A. Tool selection and locking switch 760 is comprised of a top switching member 770 and a bottom switching member 780 (not visible in FIGS. 25 and 26) and operably interacts with first instrument hub 740 and second instrument 750 to engage one of the instrument hubs with top switching member 770 for use of the hub, and consequently the surgical tool associated with that hub, and lock-out from use the other of the instrument hubs with bottom switching member 780 and the tool associated with that instrument hub. The operation of tool selection and locking switch 760 and its interaction with the first and second instrument hubs 740, 750 will be further explained later in this specification. FIGS. 25 and 26 illustrate tool selection and locking switch 760 in a first position where first instrument hub 740 has been engaged by top switching member 770 for use of the surgical tool that is associated with the first instrument hub 740 and wherein second instrument hub 750 has been engaged by bottom switching member 780 in order to lock-out the second instrument hub 750 from use by the user of the surgical instrument 700.

Figure 27:
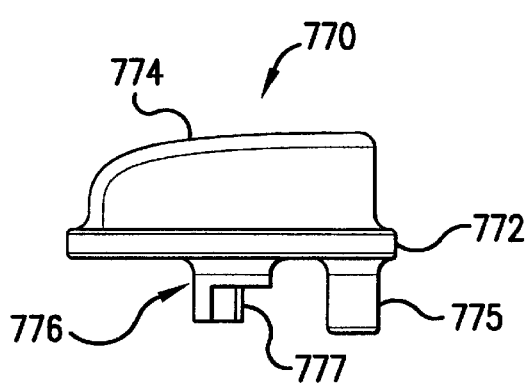
FIG. 27 is a side view of the top switching member of the embodiment of FIG. 25.
Figure 28:
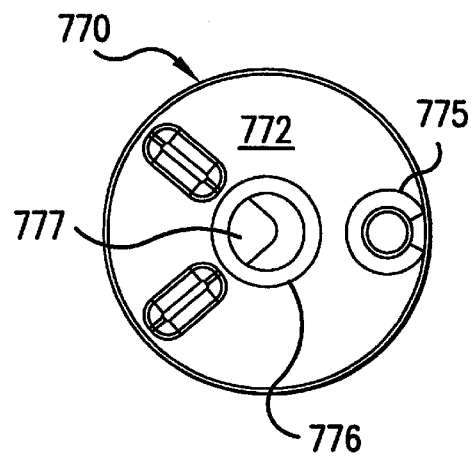
FIG. 28 is a bottom view of the top switching member of FIG. 27.
Figure 29:
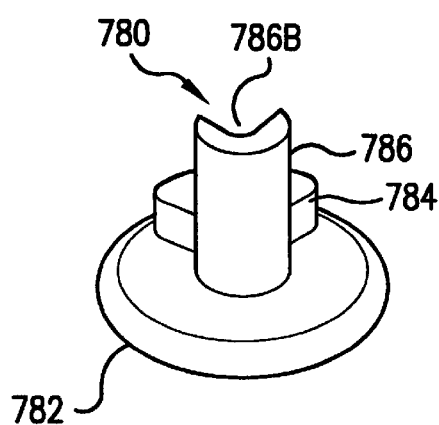
FIG. 29 is a perspective view of the bottom switching member of the embodiment of FIG. 25.
Figure 30:
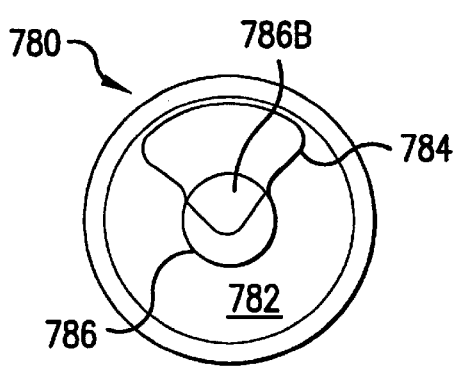
FIG. 30 is a top view of the bottom switching member of FIG. 29.

FIGS. 27 and 28 illustrate the top switching member 770 of tool selection and locking switch 760 and FIGS. 29 and 30 illustrate the bottom switching member 780 of the tool selection and locking switch 760. In first describing top switching member 770, FIG. 27 is a side view of top switching member 770 and FIG. 28 is a bottom view of the top switching member 770. As can be seen, top switching member 770 is comprised of a flat circular planar member 772. Attached to the top of circular planar member 772, such that it extends above sliding finger ring assembly 730 when top switching member 770 is mounted within sliding finger ring assembly 730, is finger grip 774. Attached to a bottom portion of planar member 772 are instrument hub actuating member 775 and bottom switch member engagement tab 776. Instrument hub actuating member 775 and bottom switch member engagement tab 776 are disposed on the bottom side of planar member 772 such that they extend within sliding finger ring assembly 730 and within body portion 710 to engage with the first and second instrument hubs 740, 750 and bottom switching member 780, respectively. Instrument hub actuating member 775 is an elongated cylindrical member and extends from planar member 772.

Bottom switch member engagement tab 776 is also a cylindrical member that extends down from planar member 772, however, bottom switch member engagement tab 776 also includes a v-shaped engagement portion 777, which can be seen in FIG. 28, the purpose of which is to engage with bottom switching member 780. As will be further explained, instrument hub actuating member 775 engages with instrument hubs 740 and 750 and bottom switch member engagement tab 776 engages with bottom switching member 780.

FIGS. 29 and 30 illustrate bottom switching member 780. FIG. 29 is a perspective view of bottom switching member 780 and FIG. 30 is a top view of bottom switching member 780. As can be seen, bottom switching member 780 is comprised of a circular base 782, an instrument hub locking member 784, and a top switch member engagement tab 786. Top switch member engagement tab 786 defines a v-shaped grove 786B which is formed to receive the v-shape engagement portion 777 of top switching member 770 within it. Bottom switching member 780 is disposed within body portion 710 for rotational motion within body portion 710. As will be further explained, the purpose of instrument hub locking member 784 is to engage with instrument hubs 740 and 750 to lock-out from operation the engaged instrument hub. The top switch member engagement tab 786 is designed to engage with top switching member 770 such that as top switching member 770 is rotated in order to engage one of the first or second instrument hubs 740, 750 with instrument hub actuating member 775 to select for use the engaged instrument hub, this rotational movement of top switching member 770 to engage an instrument hub for use also rotates bottom switching member 780 so that instrument hub locking member 784 of bottom switching member 780 engages the other of the instrument hubs that is not selected for use to lock-out from operation that instrument hub.

Figure 31:
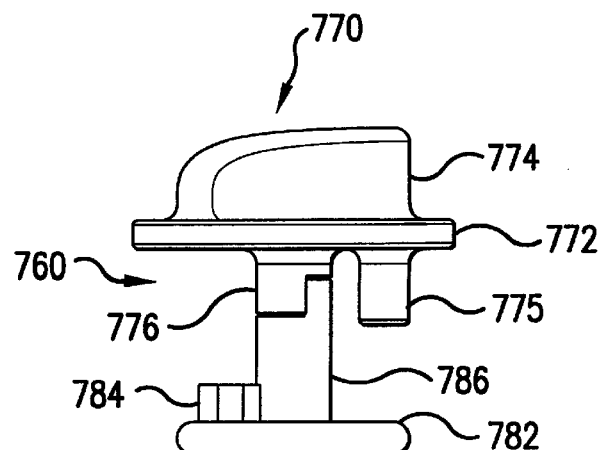
FIG. 31 is a side view of the top switching member and bottom switching member of FIGS. 27–30 in an operable configuration.
Figure 35:
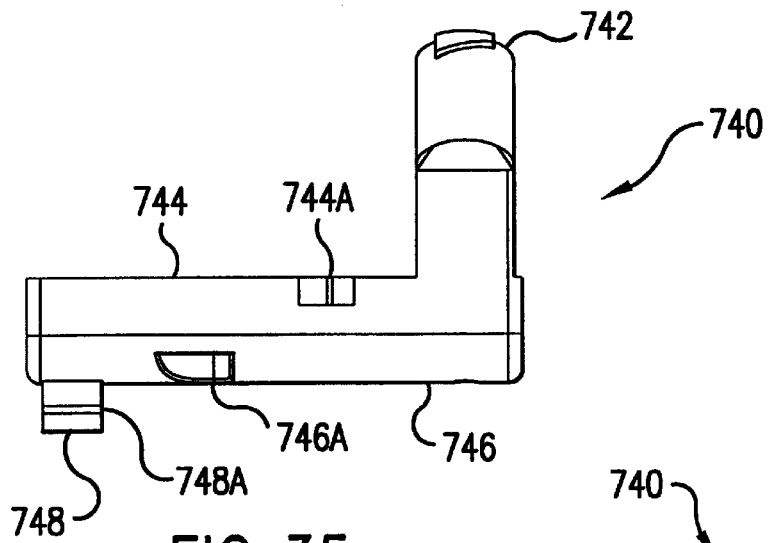
FIG. 35 is a side view of the first instrument hub of the embodiment of FIG. 25.
Figure 36:
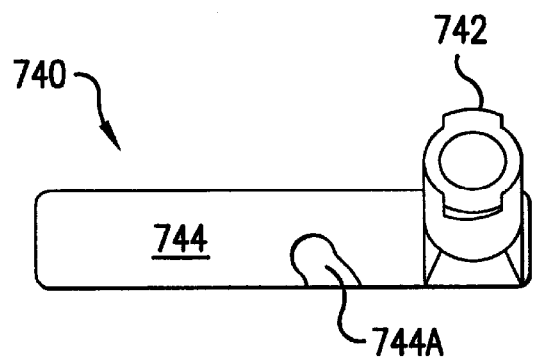
FIG. 36 is a top view of the first instrument hub of FIG. 35.
Figure 37:
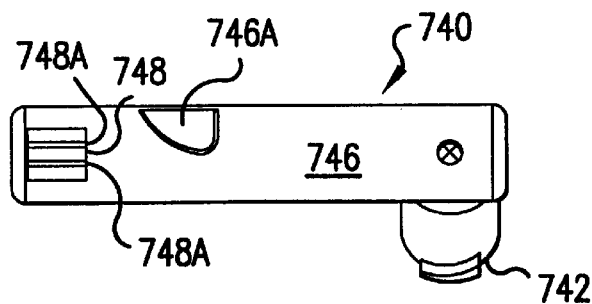
FIG. 37 is a bottom view of the first instrument hub of FIG. 35.
Figure 38:
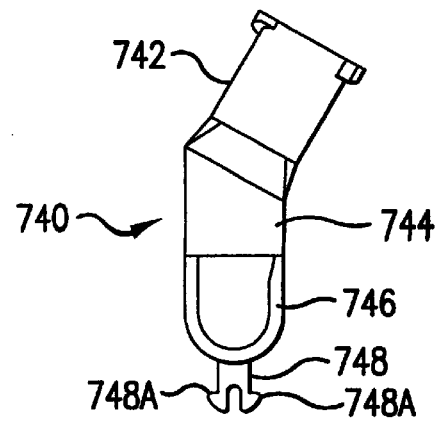
FIG. 38 is a rear view of the first instrument hub of FIG. 35.

FIG. 31 illustrates the top switching member 770 and bottom switching member 780 of the tool selection and locking switch 760 as they would be positioned with respect to each other within body portion 710 and sliding finger ring assembly 730 (both not shown) within surgical instrument 700. As can be seen, bottom switch member engagement tab 776 of top switching member 770 has engaged top switch member engagement tab 786 of bottom switching member 780 by utilizing the complementary v-shaped engagement portions of the top switching member 770 and the bottom switching member 780, as described previously. Thus, as can be understood, rotational movement of top switching member 770 will also cause rotational movement of bottom switching member 780 due to the interaction of the bottom switch member engagement tab 776 and the top switch member engagement tab 786.

FIGS. 32–34 illustrate the sliding finger ring assembly 730. FIG. 32 is a top view of the sliding finger ring assembly 730, FIG. 33 is a rear view of the finger ring assembly 730, and FIG. 34 is a bottom view of the sliding finger ring assembly 730. As can be seen, sliding finger ring assembly 730 is comprised of finger rings 731A and 731B and body portion 732. Body portion 732 is a hollow structure that is defined by top body portion 732A and bottom body portion 732B. As such, body portion 710 of surgical instrument 700 is received within surgical instrument body aperture 737, which is defined by top body portion 732A and bottom body portion 732B of finger ring assembly 730, as seen in FIG. 33. Thus, finger ring assembly 730 can be slidably moved along body portion 710 of surgical instrument 700.

Top body portion 732A of finger ring assembly 730 defines top switch member receiving aperture 733, instrument hub actuating member aperture 734, instrument hub locking member aperture 735, and instrument hub extension aperture 736. Planar member 772 of top switching member 770 is received within top switch member receiving aperture 733 in finger ring assembly 730. As such, top switching member 770 is mounted for rotational motion within sliding finger ring assembly 730. When top switching member 770 is positioned within sliding finger ring assembly 730 for rotational motion within the sliding finger ring assembly, the bottom switch member engagement tab 776 of top switching member 770 extends through instrument hub locking member aperture 735 defined by sliding finger ring assembly 730 and instrument hub actuating member 775 of top switching member 770 extends through instrument hub actuating member aperture 734 which is also defined by sliding finger ring assembly 730. Thus, as mentioned previously, top switching member 770 is mounted for rotational motion within sliding finger ring assembly 730 and the rotational movement of top switching member 770 within sliding finger ring assembly 730 is limited by the motion of instrument hub actuating member 775 within instrument hub actuating member aperture 734.

Thus, in referring back to FIG. 31, it can be seen that the union between bottom switch member engagement tab 776 of top switching member 770 and top switch member engagement tab 786 of bottom switching member 780 extends through the instrument hub locking member aperture 735 within sliding finger ring assembly 730. Also, it can be seen that instrument hub actuating member 775 of top switching member 770 would be received within instrument hub actuating member aperture 734 in sliding finger ring assembly 730.

Instrument hub extension aperture 736 in sliding finger ring assembly 730 extends completely through the top body portion 732A in sliding finger ring assembly 730 and is provided to accommodate any extensions from instrument hub 740 and instrument hub 750 that may be associated with the surgical tools that are carried by the instrument hubs. For example, as can be seen in FIGS. 25 and 26, first instrument hub 740 includes a fluid port 742 that would be utilized to provide fluid through the instrument hub to an injection needle that would be associated with the instrument hub. Similarly, second instrument hub 750 includes an electrocautery insert 752 that would be associated with a snare tool that is carried by the second instrument hub 750. Thus, sliding finger ring assembly 730 is provided with instrument hub extension aperture 736 so that any extensions from the instrument hubs may be received within the sliding finger ring assembly 730.

FIGS. 35 to 38 illustrate first instrument hub 740. Since second instrument hub 750 is formed similar to first instrument hub 740, with the exception that any extensions from the hubs may be differently formed to accommodate the particular surgical tool that is associated with the instrument hub, a detailed description will only be provided of first instrument hub 740. First instrument hub 740 is comprised of a top portion 744 and a bottom portion 746. Attached to top portion 744 is fluid port 742 that would be utilized if first instrument hub 740 was utilized in combination with an injection needle, as described previously. Top portion 744 defines an instrument hub actuating slot 744A. Instrument hub actuating slot 744A is designed to receive in it the instrument hub actuating member 775 of top switching member 770. When instrument hub actuating member 775 is rotated to be received within instrument hub actuating slot 774A of first instrument hub 740, first instrument hub 740 is mated with top switching member 770 and thus, movement of sliding finger ring assembly 730 in a distal direction along body portion 710 of surgical instrument 700 will also move first instrument hub 740 distally along body portion 710. Thus, the surgical tool that is associated with the first instrument hub 740 will also be moved distally along body portion 710 of surgical instrument 700 such that a distal end of the surgical tool would extend from a sheath that is attached to sheath attachment portion 716 of surgical instrument 700 so that the surgical tool could be utilized by the surgeon that is utilizing the instrument 700.

In further describing instrument hub 740, instrument hub 740 includes bottom portion 746. Bottom portion 746 defines an instrument hub locking slot 746A. Instrument hub locking member 784 of bottom switching member 780 is received within instrument hub locking slot 746A of instrument hub 740. Thus, when instrument hub actuating member 775 of tool switching member 770 engages with instrument hub actuating slot 744A of first instrument hub 740, the instrument hub locking member 784 engages with the instrument hub locking slot of the other instrument hub of the surgical instrument 700. Thus, through rotation of top switching member 770, one of the instrument hubs is engaged by top switching member 770 for use and the other of the instrument hubs is locked out from operation by bottom switching member 780. The v-grove arrangement between top switching member 770 and bottom switching member 780, as described previously, allows for rotation of bottom switching member 780 when top switching member 770 is rotated by a user of the surgical instrument.

Also associated with first instrument hub 740 is body engagement portion 748. Body engagement portion 748 includes retention rails 748A which extend outwardly from body engagement portion 748 and serve to guide and retain first instrument hub 740 within first channel 712A that is defined within body portion 710 of surgical instrument 700.

Figure 39:
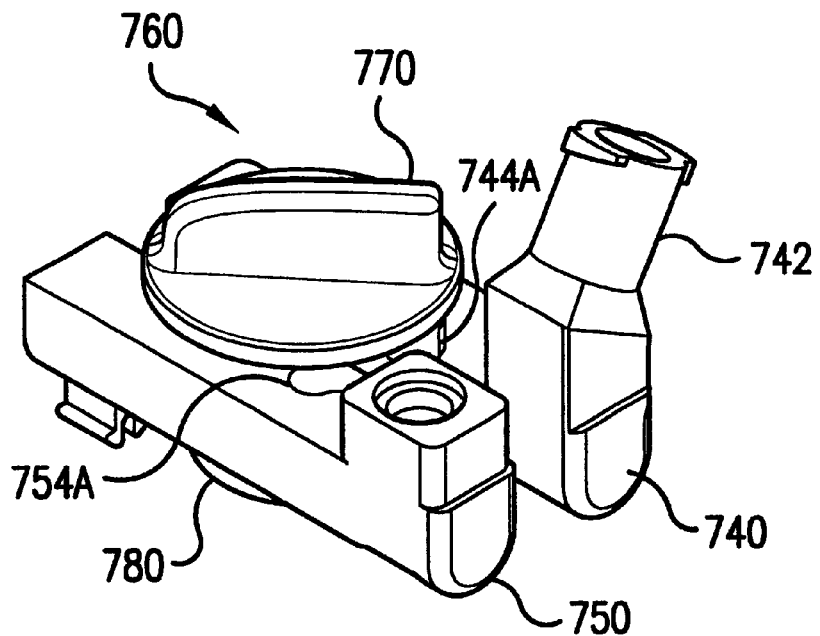
FIG. 39 is a perspective view of the tool selection and locking switch in an operable configuration with the first and second instrument hubs of the embodiment of FIG. 25.
Figure 40:
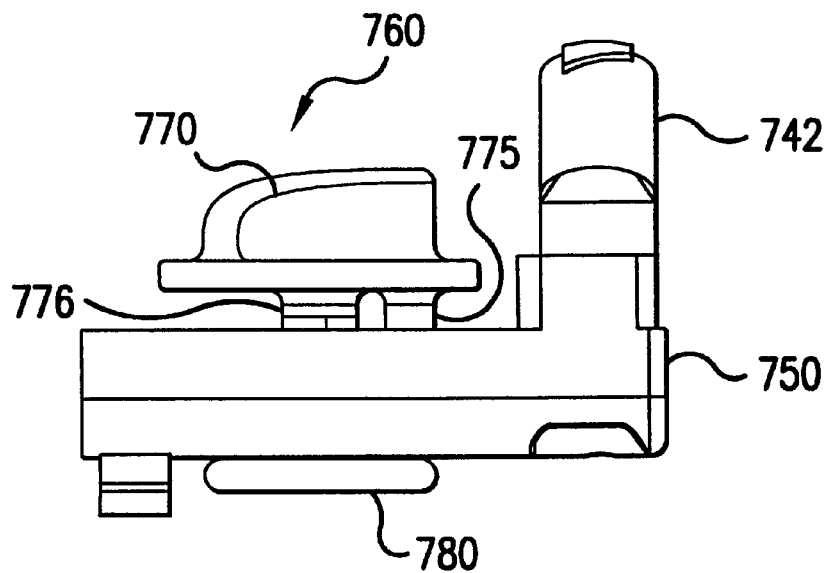
FIG. 40 is a side view of the tool selection and locking switch of FIG. 39.

FIGS. 39 and 40 illustrate the tool selection and locking switch 760 as it is used in combination with first instrument hub 740 and second instrument hub 750. For purposes of illustration, the tool selection and locking switch 760 and the first instrument hub 740 and second instrument hub 750 are shown without the sliding finger ring assembly 730. Top switching member 770 has been rotated so that instrument hub actuating member 775 (not visible in FIG. 39) is received within the instrument hub actuating slot 744A of first instrument hub 740. Whereas it can not be seen in FIGS. 39 and 40, it can be understood from the previous discussion that as top switching member 770 is rotated to engage with first instrument hub 740, bottom switching member 780 has also been rotated such that it has now engaged with the locking slot of second instrument hub 750 in order to lock-out from operation second instrument hub 750.

Figure 41:
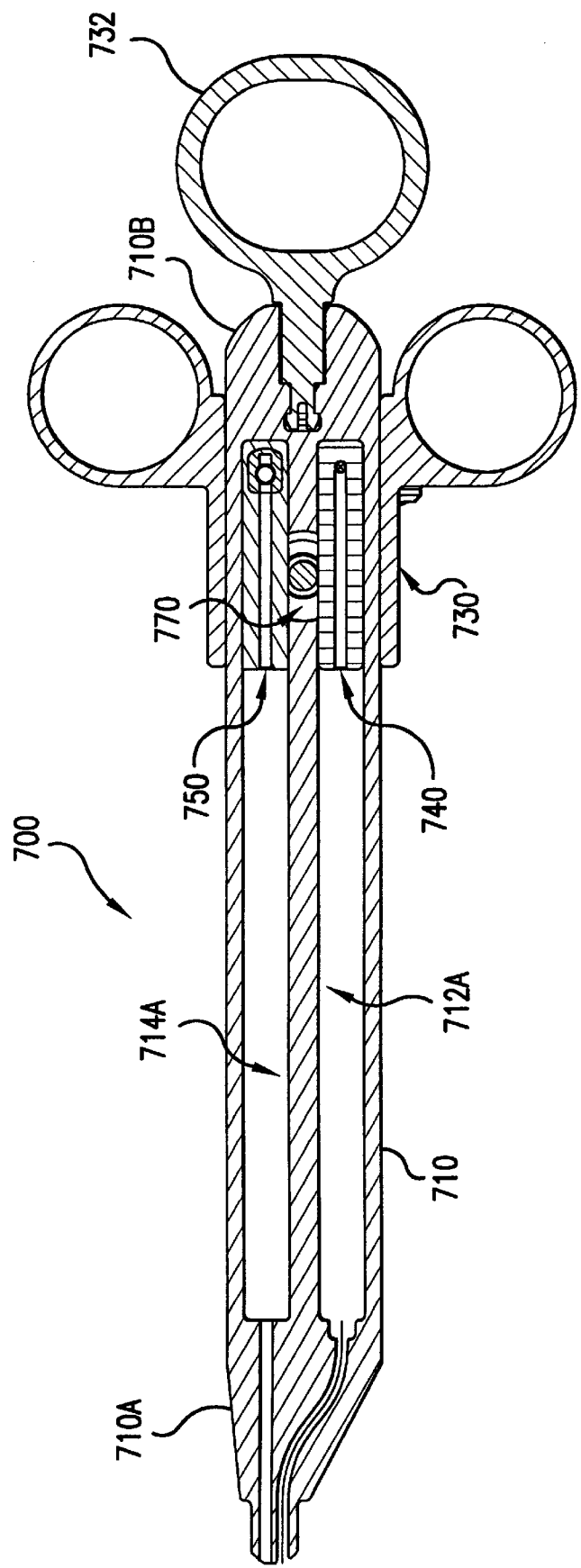
FIG. 41 is a cross-sectional view of the surgical instrument of FIG. 25 taken along line 41—41 of FIG. 26.

FIG. 41 is a cross sectional view of surgical instrument 700 taken along lines 41—41 of FIG. 26. As can be seen, first instrument hub 740 is disposed within first channel 712A and second instrument hub 750 is disposed within second channel 714A and top switching member 770 is disposed within sliding finger ring assembly 730.

In operation, a surgeon that desires to utilize a first surgical tool that is associated with first instrument hub 740 would rotate top switching member 770 such that top switching member 770 engages with first instrument hub 740. The rotation of top switching member 770 will also rotate bottom switching member 780 such that it engages with second instrument hub 750 in order to lock-out from operation the second surgical tool that is associated with second instrument hub 750. When top switching member 770 has been rotated to a first position as illustrated in FIG. 25 where the top switching member 770 has engaged with first instrument hub 740, movement of sliding finger ring assembly 730 in a distal direction along body portion 710 of surgical instrument 700 will also slide first instrument hub 740 distally along body portion 710. Thus, the surgical tool that is associated with first instrument hub 740 can be extended from surgical instrument 700. Because the sliding finger ring assembly 730, the top switching member 770, and first instrument hub 740 are all structurally mated, movement of sliding finger ring assembly 730 will cause first instrument hub 740 to move along with sliding finger ring assembly 730. Since bottom switching member 780 is rotatably mounted to body portion 710 of surgical instrument 700, its engagement with second instrument hub 750 will prevent movement of second instrument hub 750 and thus, lock-out from operation the surgical tool that is associated with second instrument hub 750.

If a surgeon desires to utilize the second surgical tool that is associated with the second instrument hub 750, the surgeon would rotate top switching member 770 such that it would engage with second instrument hub 750. The rotation of top switching member 770 to engage with second instrument hub 750 would also rotate bottom switching member 780 such that it would now engage with first instrument hub 740. Thus, movement of sliding finger ring assembly 730 would now cause movement of second instrument hub 750 along with the sliding finger ring assembly 730. Additionally, bottom switching member 780, which is now engaged with first instrument hub 740, would cause first instrument hub 740 to be locked out from operation.

Thus, as described, tool selection and locking switch 760 provides for engaging a particular instrument hub for operation of the tool associated with the instrument hub and locking out a second surgical tool from operation that is associated with a second instrument hub. In this manner, a user of the surgical instrument 700 can select a particular tool for use and prevent a second tool contained within the instrument from deployment from the tool.

Figure 42:
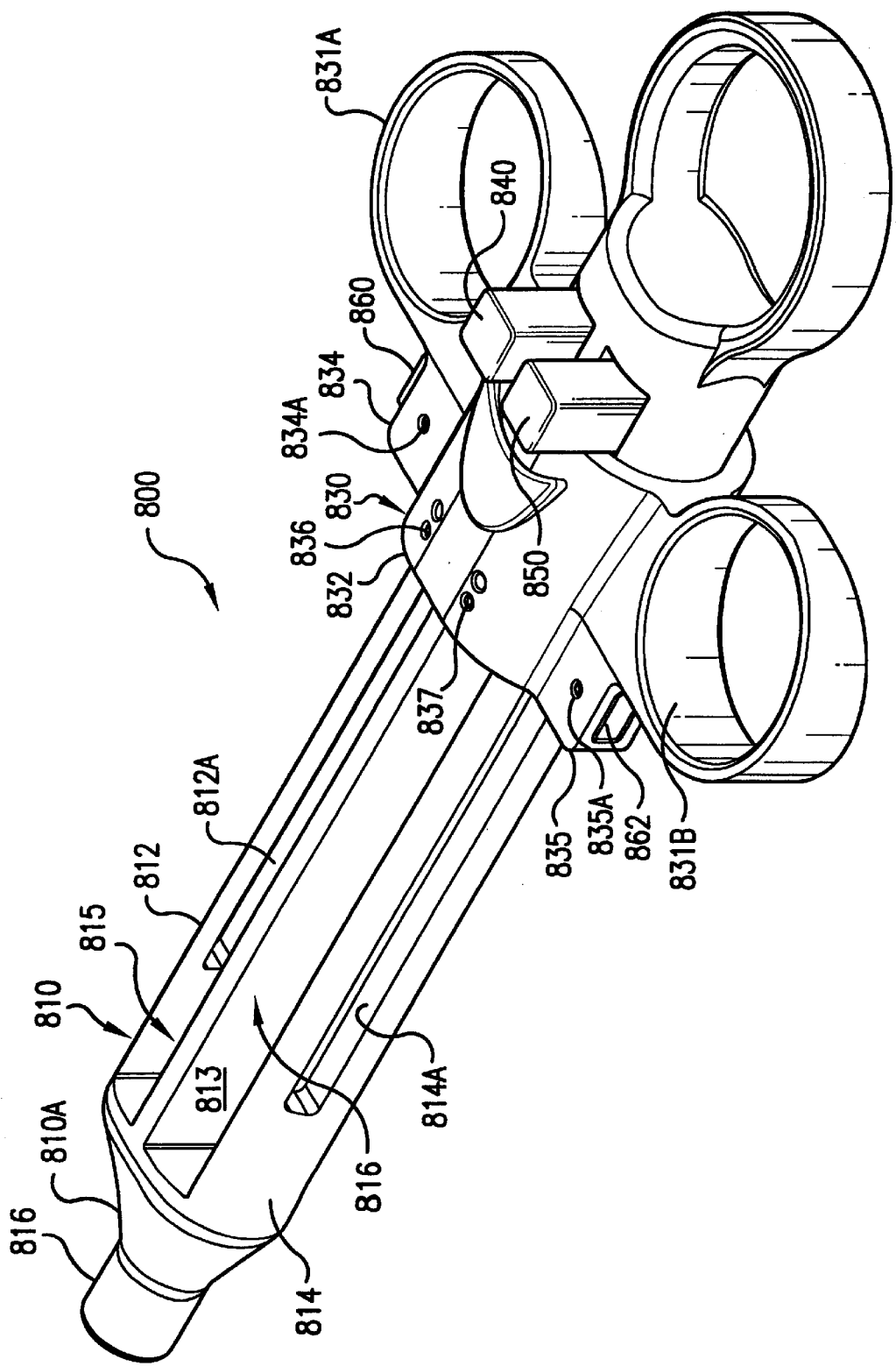
FIG. 42 is a perspective view of a multi-function surgical instrument that incorporates an eighth embodiment for the tool actuator assembly of the present invention.
Figure 43:
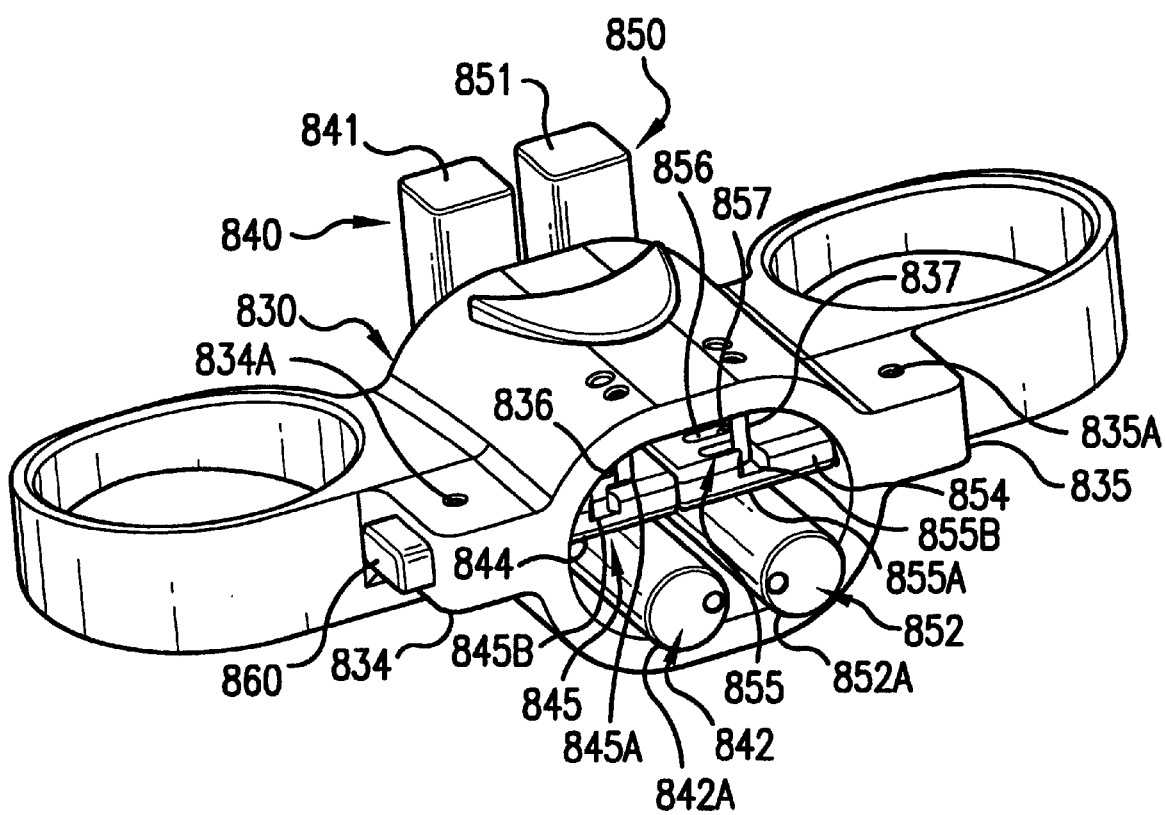
FIG. 43 is a perspective view of an operable configuration of the first and second actuator buttons, the sliding finger ring assembly, and the first and second instrument hubs of the embodiment of FIG. 42.
Figure 44:
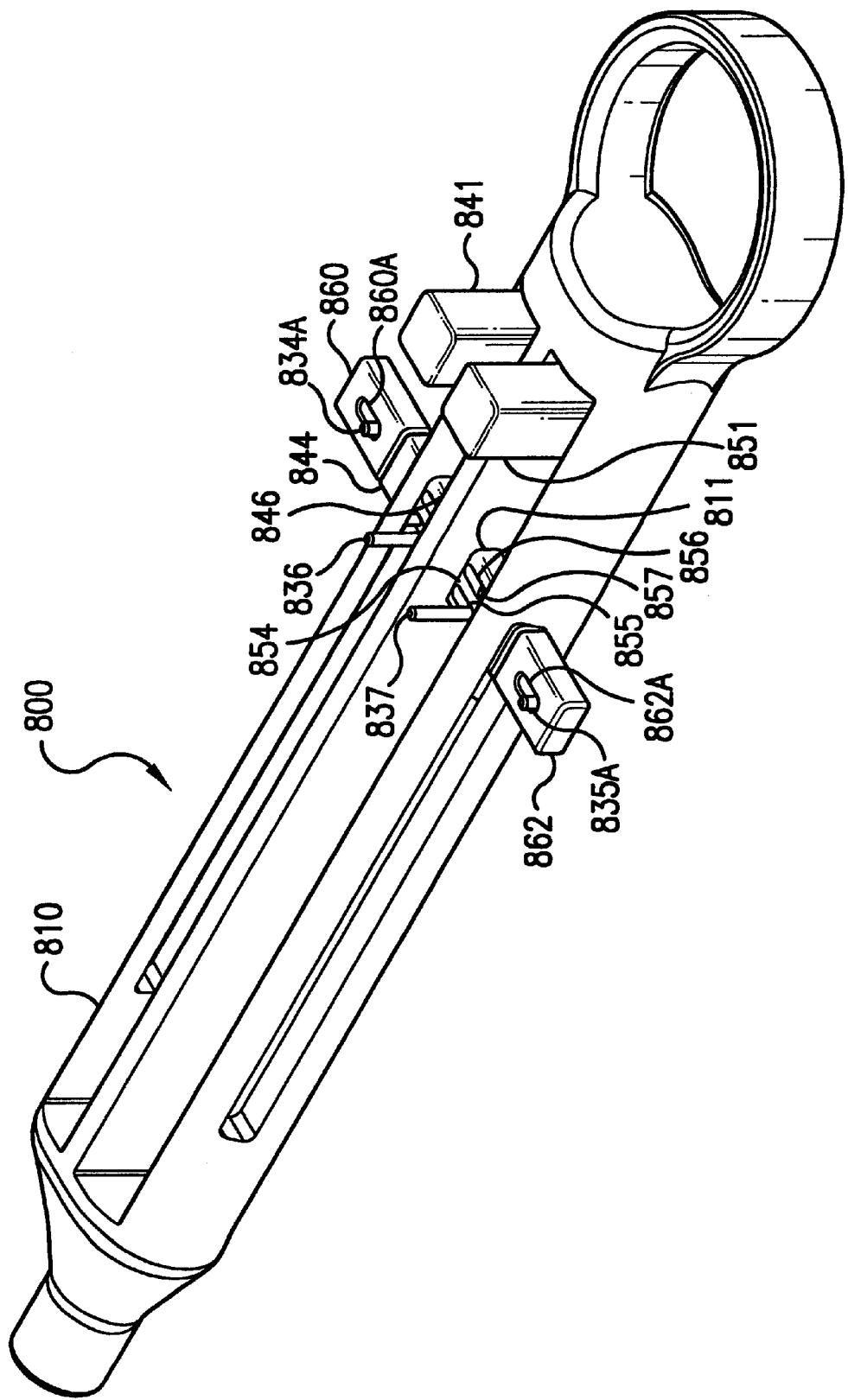
FIG. 44 is a perspective view of an operable configuration of the first and second actuator buttons and the first and second hub engagement members of the embodiment of FIG. 42.
Figure 45:
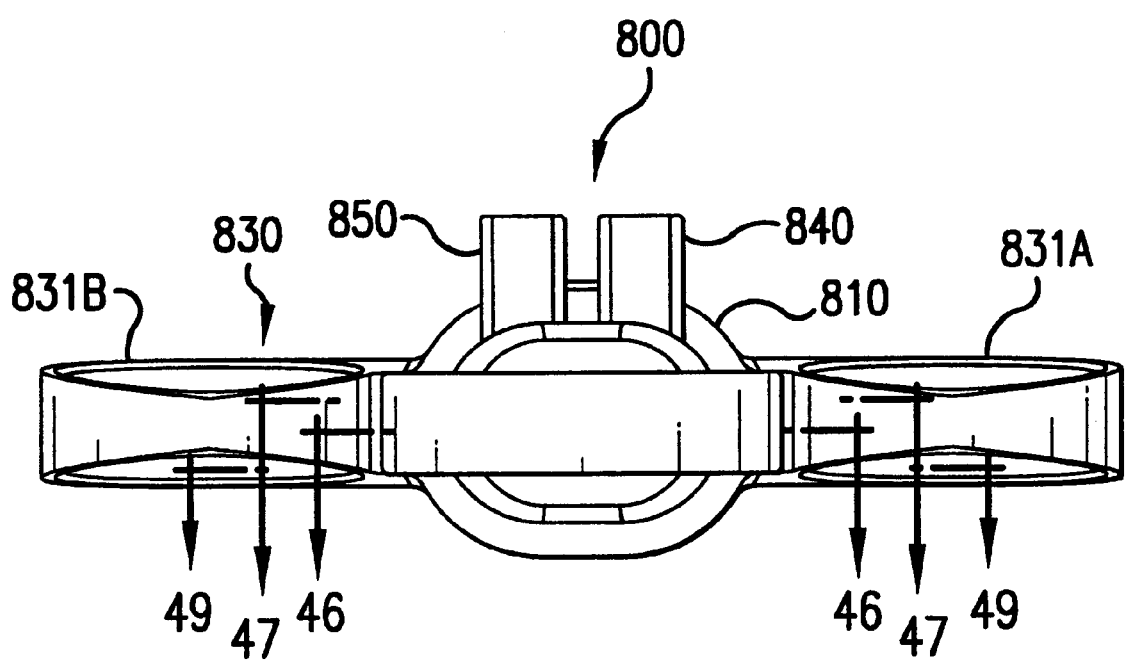
FIG. 45 is a rear view of the multi-function surgical instrument of FIG. 42.
Figure 46:
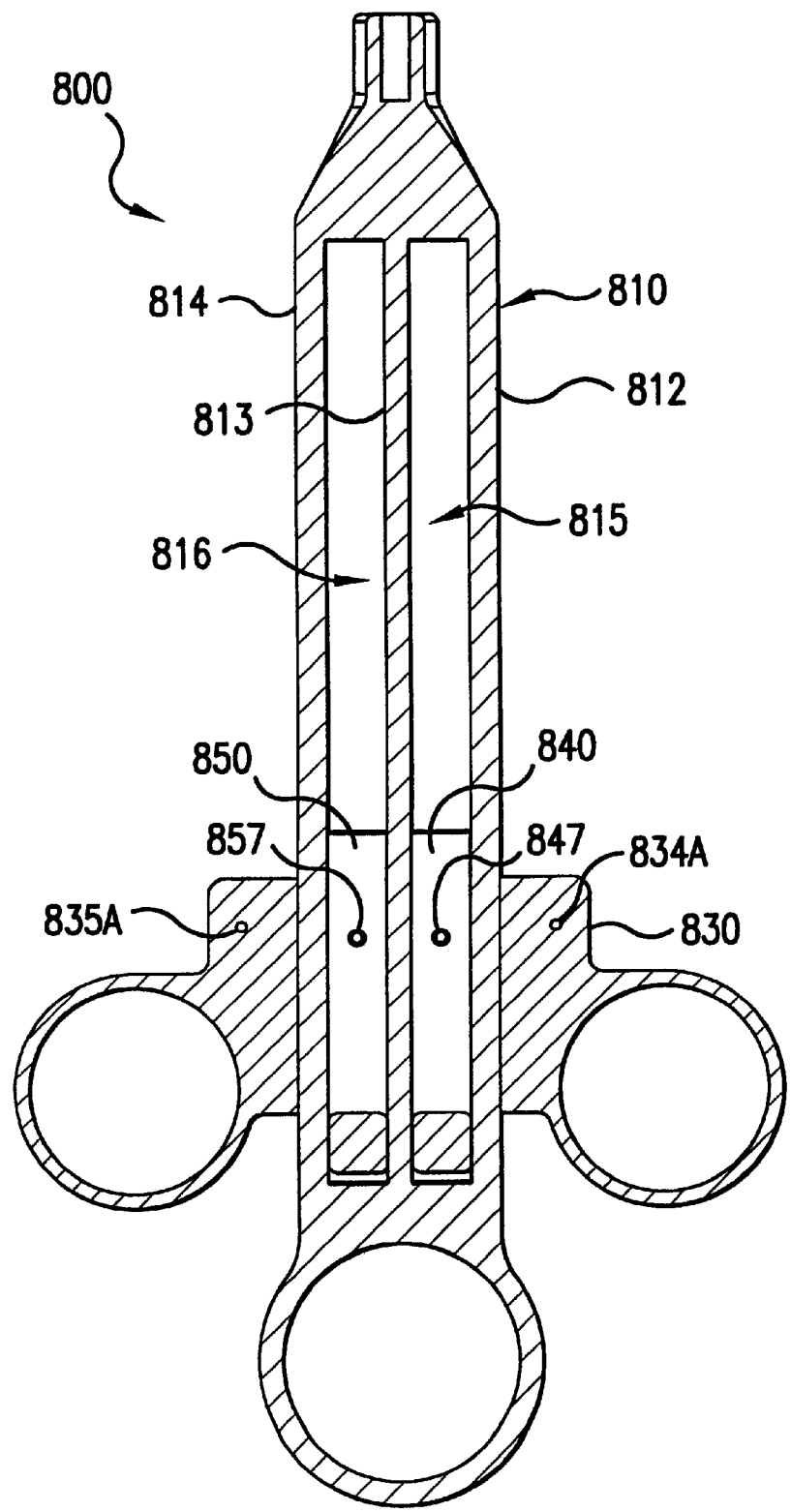
FIG. 46 is a cross-sectional view of the multi-function surgical instrument of FIG. 42 taken along line 46—46 of FIG. 45.

FIGS. 42–50 illustrate an eighth embodiment for a tool actuator assembly in accordance with the present invention. As can be seen in FIGS. 42 and 45, surgical instrument 800 is comprised of a body portion 810, a slidable finger ring assembly 830, a first instrument hub 840, a second instrument hub 850, and first and second actuator buttons 860, 862, respectively. First instrument hub 840 is associated with a first surgical tool (not shown) and second instrument hub 850 is associated with a second surgical tool (also not shown). The first and second tools could be any of a variety of tools and the present invention is not limited to any particular embodiment for the surgical tools that may be utilized in surgical instrument 800. As will be further explained later in this specification, the first surgical tool would be extended from, and retracted into, surgical instrument 800 by sliding instrument hub 840 along surgical instrument 800 and the second surgical tool would also be extended from, and retracted into, surgical instrument 800 by sliding second instrument hub 850 within surgical instrument 800. As will also be further explained, first actuator button 860 and second actuator button 862 are utilized to select which instrument hub is engaged by sliding finger ring assembly 830 so that the surgical tool associated with the selected instrument hub is able to be extended from, and retracted into, the surgical instrument 800.

In further describing surgical instrument 800, body portion 810 is comprised of outer frame member 812 and outer frame member 814. Central hub 813 is disposed between outer from member 812 and outer frame member 814. As such, central hub 813 and outer frame member 812 define a first channel 815 and central hub 813 and outer frame member 814 define a second channel 816. Located within outer frame member 812 is a slot 812A that extends generally along the entire length of body portion 810. Similarly, outer frame member 814 also includes slot 814A. As will be further explained later in this specification, first actuator button 860 extends through slot 812A and second actuator button 862 extends through 814A.

Distal end 810A of body portion 810 includes sheath attachment portion 816. Sheath attachment portion 816 is provided so that a sheath can be connected to surgical instrument 800 for insertion into the body of a patient. An aperture (not shown in FIG. 42) extends through distal end 810A of body 810 such that the first surgical tool and the second surgical tool may extend from surgical instrument 800.

Figure 47:
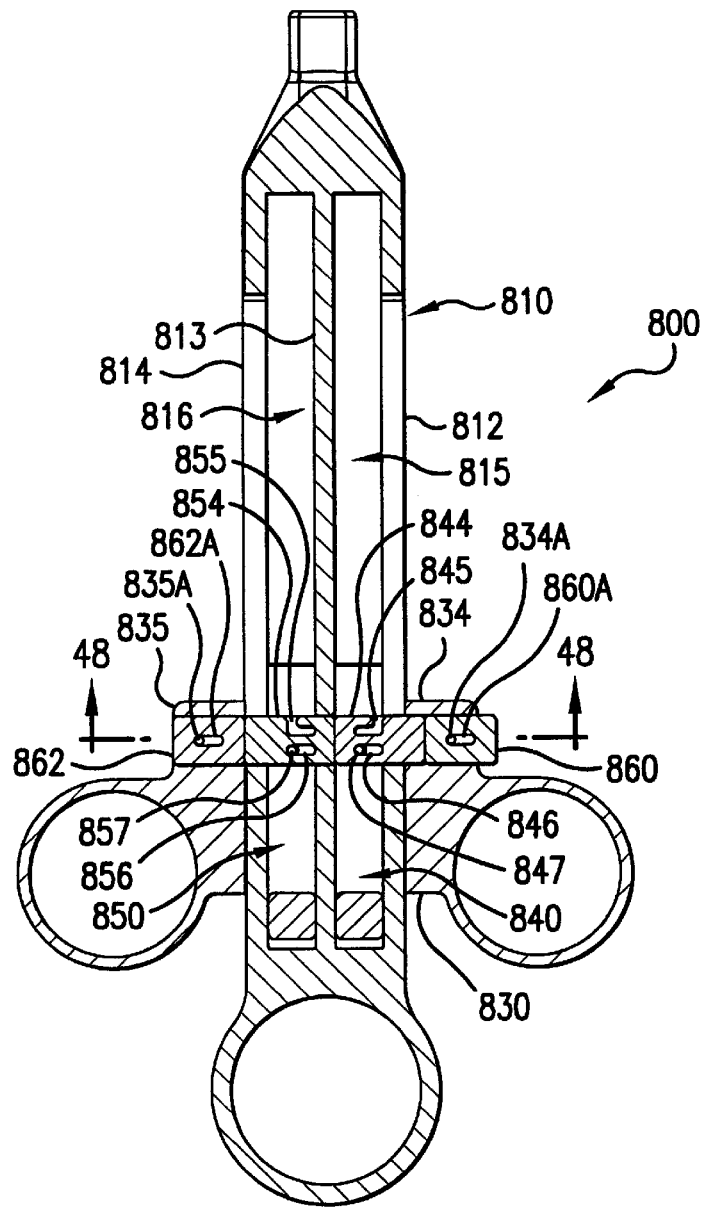
FIG. 47 is a cross-sectional view of the multi-function surgical instrument of FIG. 42 taken along line 47—47 of FIG. 45.
Figure 48:
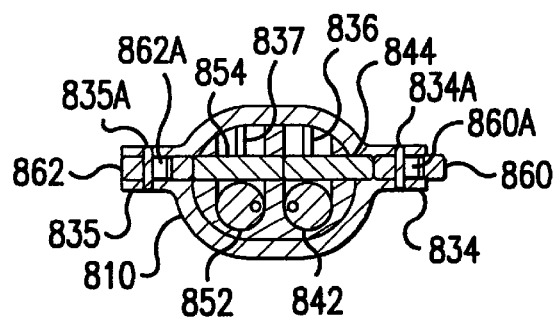
FIG. 48 is a cross-sectional view of the multi-function surgical instrument of FIG. 42 taken along line 48—48 of FIG. 47.
Figure 49:
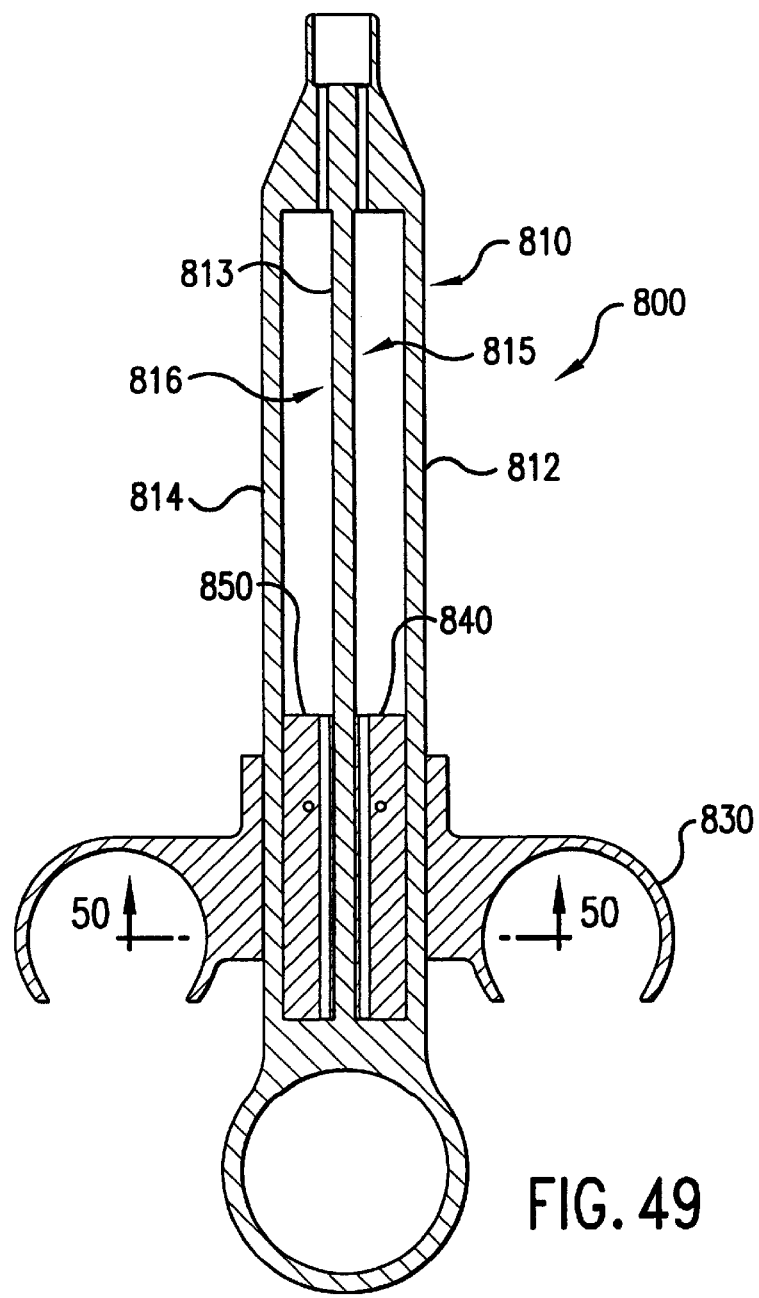
FIG. 49 is a cross-sectional view of the multi-function surgical instrument of FIG. 42 taken along line 49—49 of FIG. 45.
Figure 50:
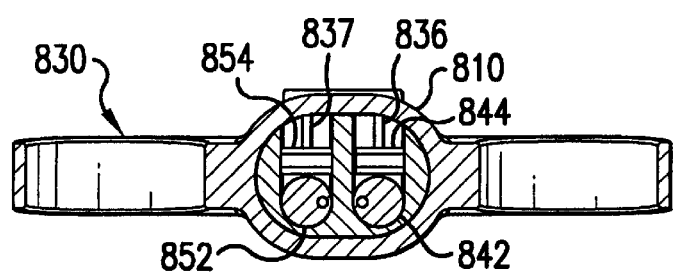
FIG. 50 is a cross-sectional view of the multi-function surgical instrument of FIG. 42 taken along line 50—50 of FIG. 49.

Sliding finger ring assembly 830 is disposed on body portion 810 for slidable motion with respect to body portion 810. Sliding finger ring assembly 830 includes a first finger ring 831A and a second finger ring 831B. Body portion 832 of finger ring assembly 830 is a hollow, cylindrical member that receives body portion 810 of surgical instrument 800 within it. Disposed on either side of body portion 832 of sliding finger ring assembly 830 are actuator button housings 834, 835. As can be seen, first actuator button housing 834 houses first actuator button 860 within it and second actuator button housing 835 houses second actuator button 862 within it. As can be seen in FIGS. 42 and 47, first actuator button housing 834 includes first actuator button guide pin 834A within it and second actuator button housing 835 contains second actuator button guide pin 835A within it. First actuator button guide pin 834A is disposed within guide slot 860A of first actuator button 860 and second actuator button guide pin 835A is disposed within guide slot 862A of second actuator button 862. The actuator button guide pins in each actuator button housing are rigidly attached to the housing. As such, the actuator button guide pins, in conjunction with the guide slots in each actuator button, serve to guide and limit the motion of the actuator buttons 860 and 862 within actuator button housings 834 and 835, respectively.

FIG. 43 illustrates the assembled configuration of first and second actuator buttons 860, 862 (not shown), respectively, sliding finger ring assembly 830, and first and second instrument hubs 840, 850, respectively. For purposes of illustration, FIG. 43 illustrates the interaction of the components previously mentioned without illustrating body portion 810 of surgical instrument 800. In further describing the interaction of first instrument hub 840, second instrument hub 850, finger ring assembly 830, and first actuator button 860 and second actuator button 862, first instrument hub 840 and second instrument hub 850 will be more fully described.

As can be seen in FIG. 43, first instrument hub 840 is comprised of first instrument hub extension member 841, first tool attachment member 842, and first hub engagement member 844. First tool attachment member 842 is a cylindrical body and serves as the attachment mechanism for a first surgical tool that would be incorporated into surgical instrument 800. The surgical tool would attach to the distal end 842A of the first tool attachment member 842. First instrument hub extension member 841 can be integrally formed with first tool attachment member 842. First instrument hub 840 also includes first hub engagement member 844. First hub engagement member 844 defines an engagement slot 845 which includes an engagement portion 845A and a open portion 845B. First hub engagement member 844 also includes attachment slot 846 (visible in FIGS. 44 and 47) within it. Attachment slot 846 receives hub attachment pin 847 (also visible in FIG. 47) within it. Hub attachment pin 847 extends up from first tool attachment member 842 and through attachment slot 846. As such, first hub engagement member 844 is slidably mounted onto first tool attachment member 842 and is movable with respect to first tool attachment member 842 in a direction perpendicular to the longitudinal axis of the first tool attachment member 842, i.e., in a direction transverse to the direction of movement of first instrument hub 840 within body 810. Extending downward from body portion 832 of sliding finger ring assembly 830 is first finger ring engagement pin 836. First finger ring engagement pin 836 is rigidly attached to sliding finger ring assembly 830 and is received within engagement slot 845 of the first hub engagement member 844.

Similarly, second instrument hub 850 also includes a second tool attachment member 852 which would have attached to its distal end 852A a second surgical tool. Formed with second tool attachment member 852 is second instrument hub extension member 851. Also, second hub engagement member 854, which defines engagement slot 855 and attachment slot 856 is slidably mounted onto second tool attachment member 852. Engagement slot 855 also includes an engagement portion 855A and an open portion 855B. Additionally, a hub attachment pin 857 is disposed on second tool attachment member 852 and is received within attachment slot 856. A second finger ring engagement pin 837 is rigidly attached to body portion 832 of sliding finger ring assembly 830 and extends downward from body portion 832. Second finger ring engagement pin 837 is received within engagement slot 855 of second hub engagement member 854.

FIG. 44 illustrates the configuration of first and second actuator buttons 860, 862, respectively, and first hub engagement member 844 and second hub engagement member 854. For purposes of clarity, finger ring assembly 830 is not shown in FIG. 44, however, the first finger ring engagement pin 836 and second finger ring engagement pin 837 and the first actuator button guide pin 834A and second actuator button guide pin 835A, which are all rigidly attached to the sliding finger ring assembly 830, are shown so that the structural arrangement between the pins and the associated members can be clearly seen. As can be seen in FIG. 44, body portion 810 of surgical instrument 800 includes an aperture 811 through it so that the hub engagement members 844 and 854 may move transversely with respect to body portion 810 and through body portion 810, as will be described below.

FIGS. 46–50 illustrate various cross-sectional views of surgical instrument 800 as taken along FIG. 45.

In describing the operation of the tool actuator assembly in accordance with the embodiment of FIGS. 42–50, reference will be made particularly to FIG. 43. As can be understood in FIG. 43, second actuator button 862 (not visible) has been depressed so that it extends entirely within second actuator button housing 835. Motion of second actuator button 862 will be restrained against further motion within housing 835 due to engagement of second actuator button guide pin 835A within guide slot 862A of second actuator button 862. When second actuator 862 is depressed into second actuator button housing 835, second actuator button 862 in-turn moves second hub engagement member 854 in a direction towards the center of surgical instrument 800. As second hub engagement member 854 is moved in this direction, second finger ring engagement pin 837 will be positioned within engagement slot 855 such that second finger ring engagement pin 837 is disposed in the open portion 855B of engagement slot 855.

The movement of second actuator button 862 and second hub engagement member 854 also forces first hub engagement member 844 and first actuator button 860 in the same direction. This movement of first hub engagement member 844 causes first finger ring engagement pin 836 to be positioned within engagement portion 845A of engagement slot 845. Further, in this position, first hub engagement member 844 extends completely out of aperture 811 that is included in body portion 810. Thus, first hub engagement member 844 is not constrained against distal movement along body portion 810 by body portion 810. The movement of first hub engagement member 844 forces first actuator button 860 to extend out from first actuator button housing 834.

Thus, with second actuator button 862 in this position where it is fully inserted within second actuator button housing 835, finger ring assembly 830, through first finger ring engagement ring pin 836, which is now engaged with first hub engagement member 844, will allow first instrument hub 840 to be moved distally along body portion 810 of surgical instrument 800 when sliding finger ring assembly 830 is moved distally along body portion 810. Because second finger ring engagement pin 837 is now received within open portion 855B of engagement slot 855 of second hub engagement member 854, as the finger ring assembly 830 is moved distally along body portion 810, the second finger ring engagement pin 837 will be moved out of second hub engagement member 854, thus not engaging second hub engagement member 854. The second instrument hub will then not be selected for movement along with sliding finger ring assembly 830. Because second hub engagement member 854 will be received within aperture 811 in body portion 810, the second instrument hub 850 will, in effect, be locked from distal movement along surgical instrument 800.

In order to select the second instrument hub 850 for movement along with sliding finger ring assembly 830, the same procedure as outlined above is utilized. As such, to select second instrument hub 850, and thus, a second surgical tool that is associated with the second instrument hub 850, for activation with the sliding finger ring assembly 830, the operator would depress first actuator button 860 so that it is fully received within first actuator button housing 834. The movement of first actuator button 860 in this direction would result in the first finger ring engagement pin 836 being received within the open portion 845B of engagement slot 845 in first hub engagement member 844. Additionally, this movement of first actuator button 860 would force second finger ring engagement pin 837 to be received within the engagement portion 855A of engagement slot 855 and second hub engagement member 854. Thus, as sliding finger ring assembly 830 is moved distally along body portion 810 of surgical instrument 800, second instrument hub 850 would also be moved distally along body portion 810 due to the interaction between second finger ring engagement pin 837 and second hub engagement member 854.

Thus, the actuator assembly as described in FIGS. 42–50 provide for selectively engaging a surgical tool for use within surgical instrument 800. The surgical tool that is not selected for use is, in effect, locked into position within the body 810 of the surgical instrument 800 so that it may not be deployed from the instrument 800.

FIGS. 51–75 illustrate a ninth embodiment for the tool actuator assembly of the present invention. As will be further described, and as will become clear, the surgical instrument 900 of FIGS. 51–75 is similar to the surgical instruments disclosed in the previous two embodiments in that it contains two instrument hubs that are engageable by an actuator. However, the configuration of the actuator assembly and hub assemblies are different in the present embodiment from the previous embodiments discussed.

Figure 51:
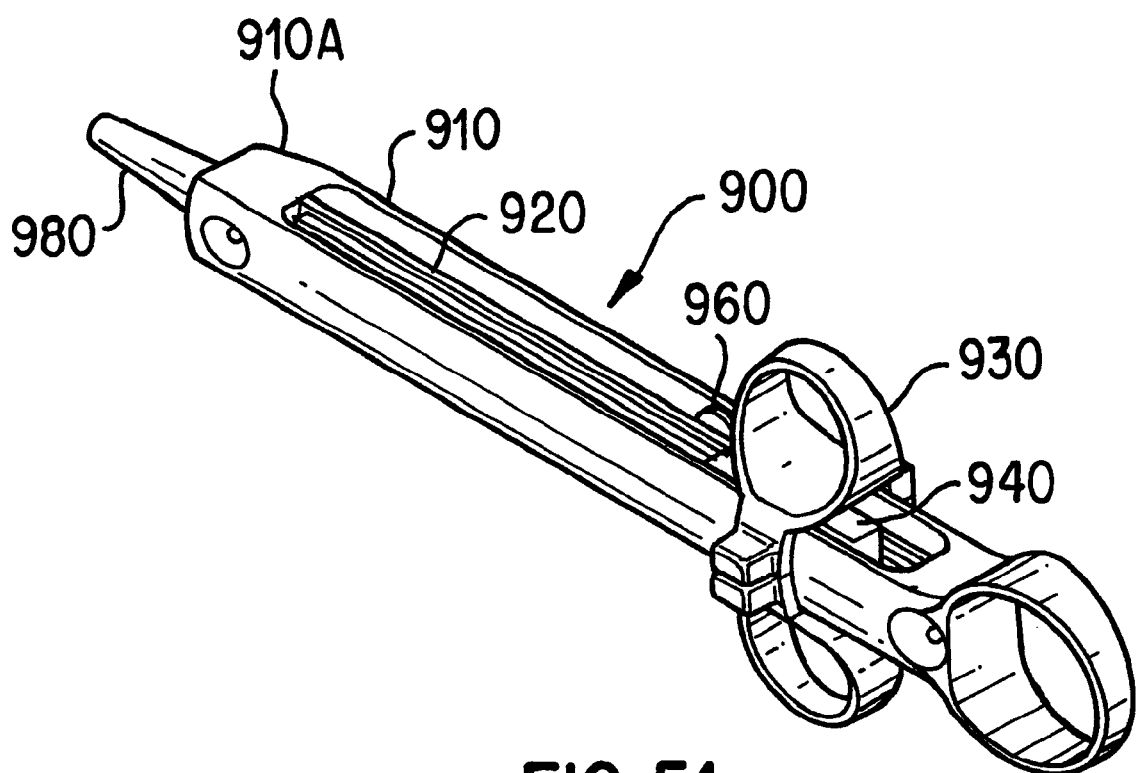
FIG. 51 is a perspective view of a multi-function surgical instrument that incorporates a ninth embodiment for the tool actuator assembly of the present invention.
Figure 52:
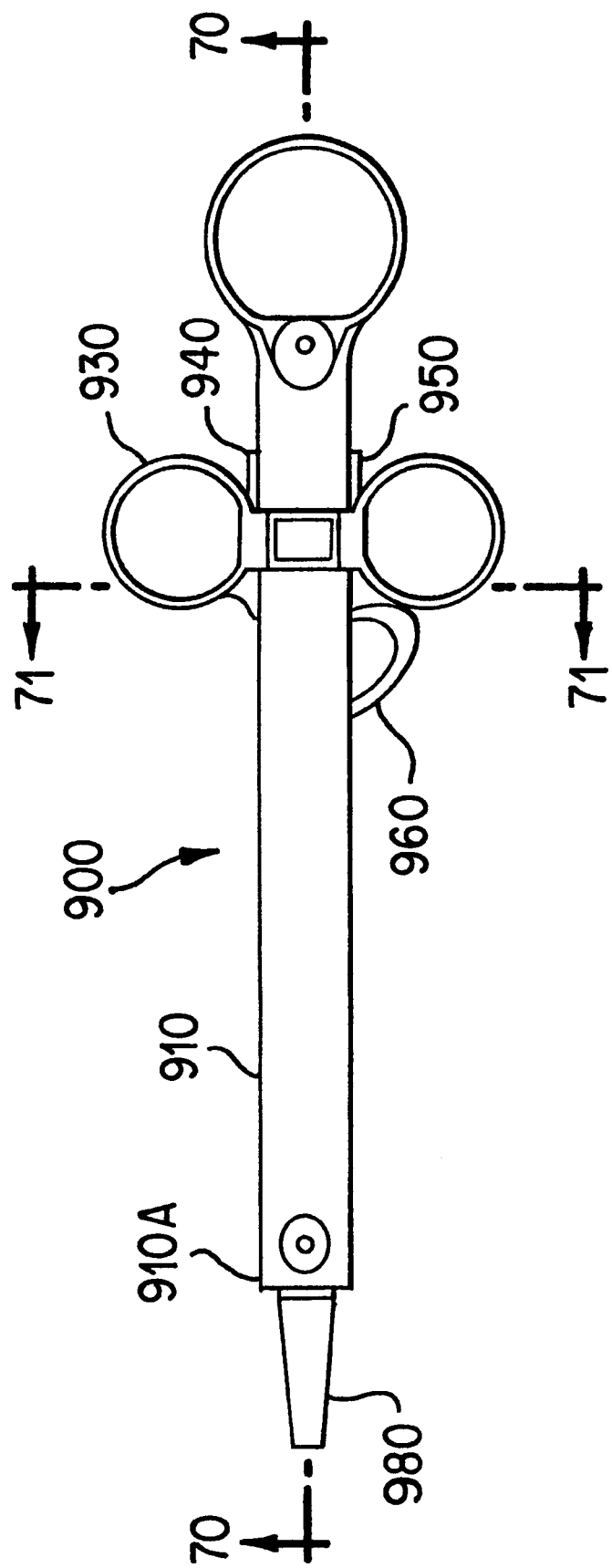
FIG. 52 is a top view of the multi-function surgical instrument of FIG. 51.
Figure 53:
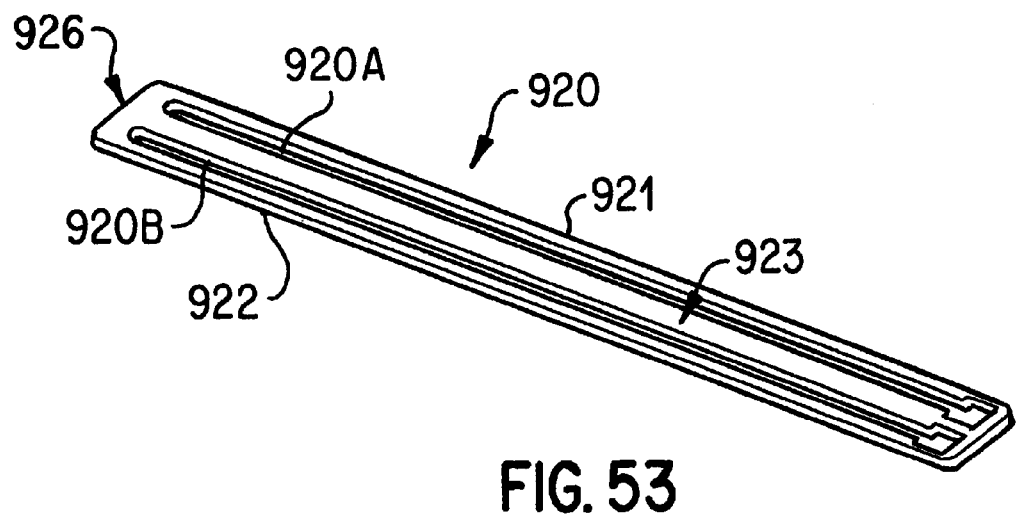
FIG. 53 is a perspective view of the guide bar of the embodiment of FIG. 51.
Figure 54:
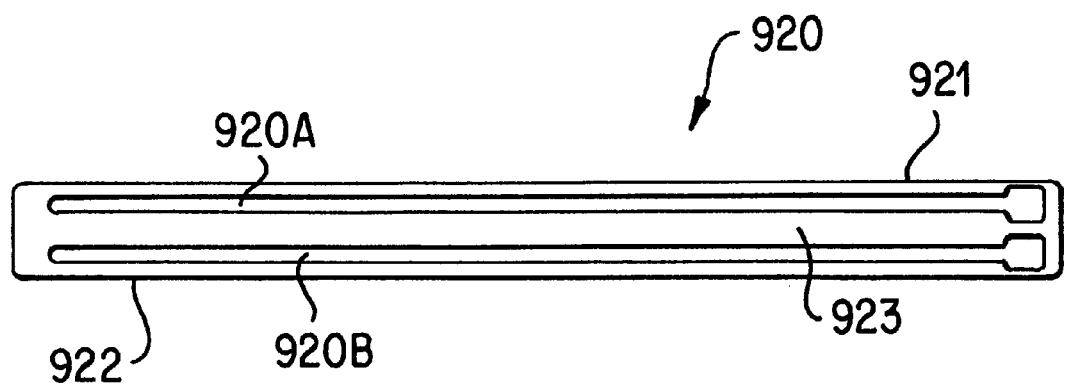
FIG. 54 is a top view of the guide bar of FIG. 53.
Figure 59:
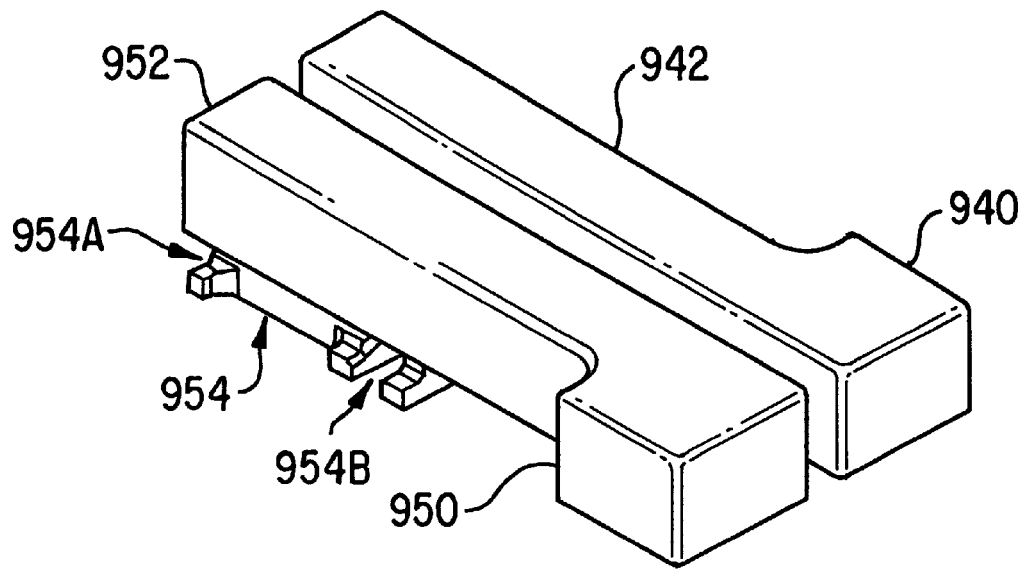
FIG. 59 is a perspective view of the first and second instrument hubs of the embodiment of FIG. 51.
Figure 60:
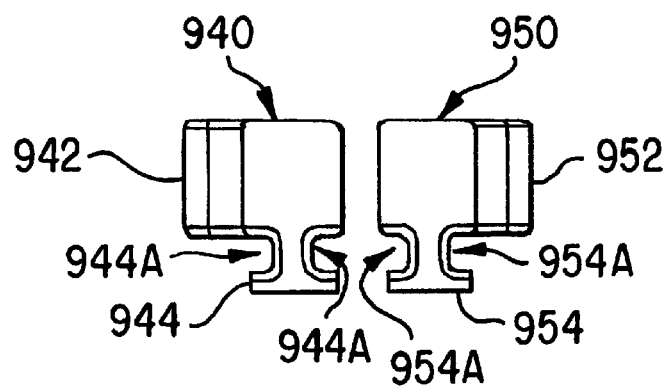
FIG. 60 is a front view of the first and second instrument hubs of FIG. 59.
Figure 61:
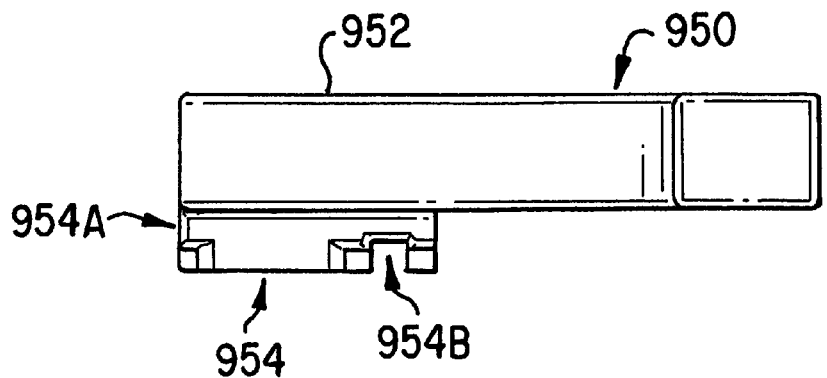
FIG. 61 is a side view of the second instrument hub of FIG. 59.
Figure 62:
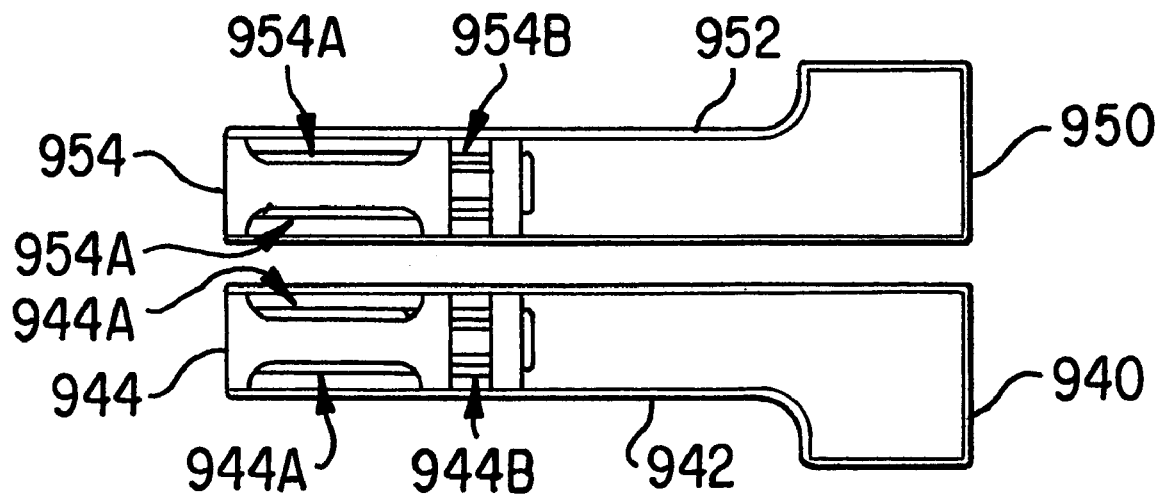
FIG. 62 is a bottom view of the first and second instrument hubs of FIG. 59.
Figure 63:
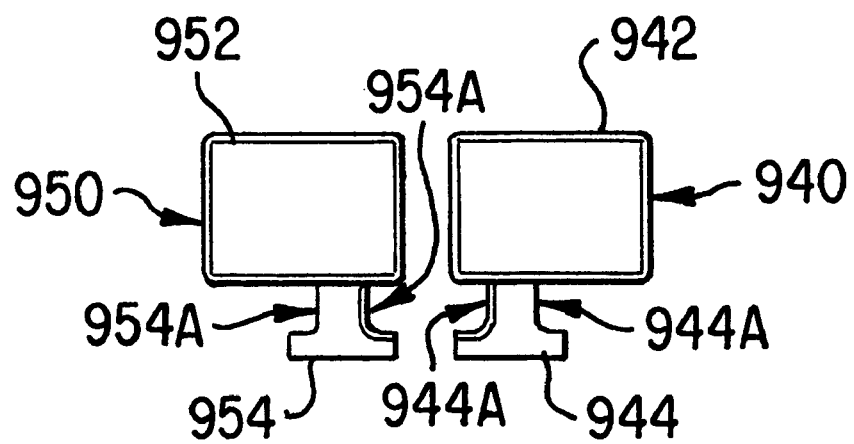
FIG. 63 is a rear view of the first and second instrument hubs of FIG. 59.

FIGS. 51 and 52 illustrate surgical instrument 900. As can be seen, surgical instrument 900 is comprised of a body portion 910, a guide bar 920, a sliding finger ring assembly 930, a first instrument hub 940, a second instrument hub 950 (not visible in FIG. 51), and a hub actuator 960. Each of these components that are associated with surgical instrument 900 will be discussed in further detail below. As described previously for embodiments 7 and 8, surgical instrument 900 also includes a first surgical tool and a second surgical tool (not shown in FIGS. 51–75). As such, the first surgical tool would be associated with first instrument hub 940 and the second surgical tool would be associated with second instrument hub 950. The present invention is capable of being utilized with any of a variety of devices for the first surgical tool and the second surgical tool and the present invention is not limited to any particular embodiments for the surgical tools. As will be further explained, the first and second surgical tools are capable of being extended from, and retracted into, surgical instrument 900 by movement of first instrument hub 940 and second instrument 950, respectively, along body portion 910 of surgical instrument 900.

Attached at distal end 910A of body portion 910 is sheath stress relief member 980. A sheath can be attached to sheath stress relief member 980 for insertion into the body of a patient and the first and second surgical tools included in surgical instrument 900 would extend through the sheath for insertion into the body of the patient.

FIGS. 53–58 illustrate the guide bar 920 of surgical instrument 900. As can be seen, guide bar 920 is comprised of an outer frame member 921, an outer frame member 922, and a central hub 923. Outer frame member 921 and central hub 923 define a first channel 920A and outer frame member 922 and central hub member 923 define a second channel 920B. As will be explained further later in this specification, first instrument hub 940 is slidably disposed within first channel 920A and second instrument hub 950 is slidably disposed within second channel 920B.

Central hub 923 is comprised of a hub guide member 926, which is a flat planar member. Disposed on the underside and extending perpendicular from hub guide member 926 is actuator guide member 924. Actuator guide member 924 defines an aperture 925 which includes an actuator tab slot 925A and an actuator guide structure slot 925B. As will be further explained, actuator tab slot 925A provides an opening within actuator guide member 924 such that the actuator tab that is associated with hub actuator 960 is able to be rotated through actuator guide member 924 from engagement with one instrument hub to engagement with the other instrument hub. Actuator guide structure slot 925B provides clearance through actuator guide member 924 for the guide structure that is associated with hub actuator 960. As will also be explained, actuator guide member 924 guides the movement of hub actuator 960 and the sliding finger ring assembly 930 along surgical instrument 900.

FIGS. 59–63 illustrate first instrument hub 940 and second instrument hub 950. Since first instrument hub 940 is formed similar to second instrument hub 950, a detailed discussion will only be provided for second instrument hub 950, which can be clearly seen in FIGS. 59–63. Second instrument hub 950 is comprised of a body portion 952 and a guide portion 954. Body portion 952 is formed in an elongated rectangular shape. Guide portion 954 extends from the bottom of body portion 952 and defines a guide slot 954A and an actuator tab engagement slot 954B. Guide slot 954A is formed on both sides of guide portion 954, as can be clearly seen in FIG. 60, and actuator tab engagement slot 954B extends transversely completely through guide portion 954. Guide slot 954A receives within it outer frame member 922 of guide bar 920 on one side of guide portion 954 and receives within it on the other side of guide portion 954 hub guide planar member 926 of central hub 923. Thus, second instrument hub 950 is slidably disposed on guide bar 920 within surgical instrument 900. Actuator tab engagement slot 954B receives within it hub actuator 960 when the user of surgical instrument 900 desires to select the tool associated with second instrument hub 950 for use.

As mentioned above, first instrument hub 940 is formed similar to second instrument hub 950 and thus, only a brief description of first instrument hub 940 will be provided. First instrument hub 940 is also comprised of body portion 942 and guide portion 944. Guide portion 944 defines guide slot 944A and actuator tab engagement slot 944B. Guide slot 944A is also formed on both sides of guide portion 944 and thus, guide portion 944 of first instrument hub 940 is received within first channel 920A of guide bar 920 such that first instrument hub 940 is slidably disposed on guide bar 920. Actuator tab engagement slot 944B also receives within it hub actuator 960 when a user of surgical instrument 900 desires to select the tool associated with first instrument hub 940 for use.

Figure 64:
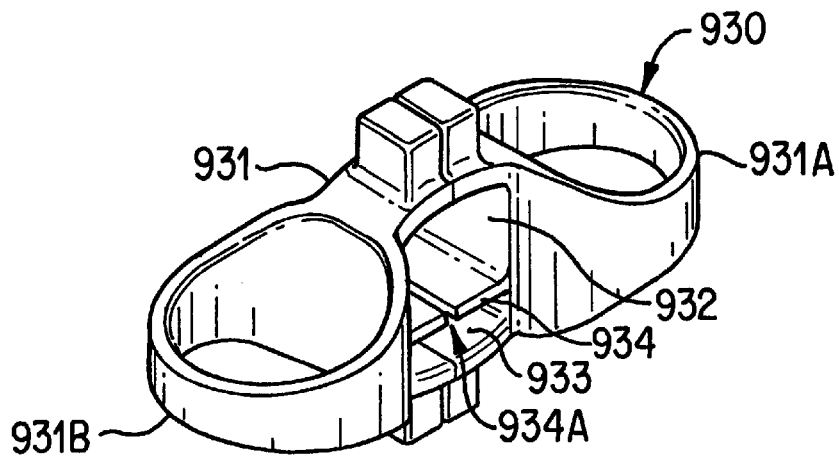
FIG. 64 is a perspective view of the sliding finger ring assembly of the embodiment of FIG. 51.
Figure 65:
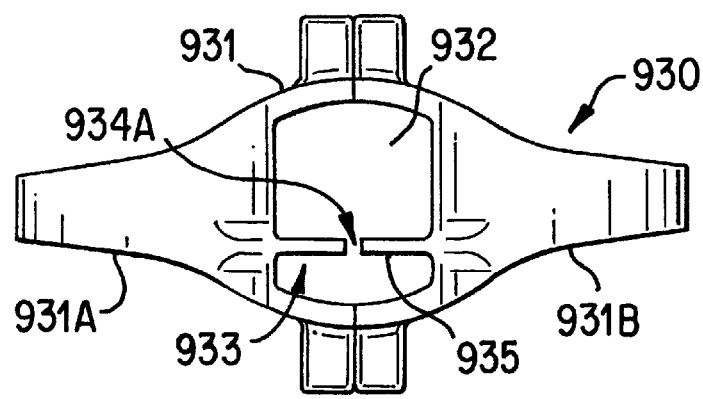
FIG. 65 is a front view of the sliding finger ring assembly of FIG. 59.
Figure 66:
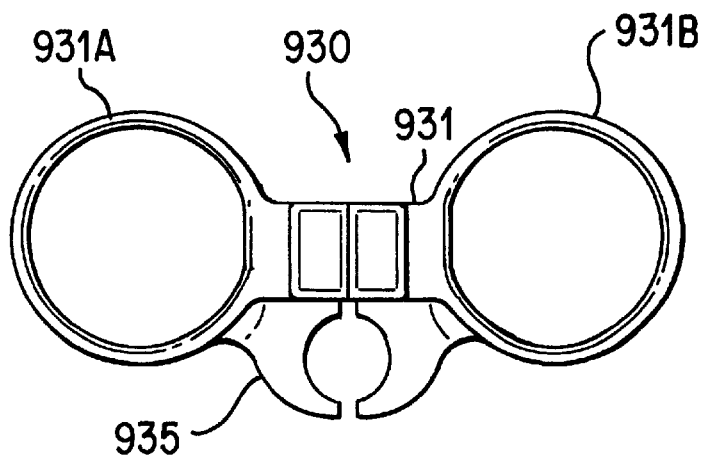
FIG. 66 is a top view of the sliding finger ring assembly of FIG. 59.

FIGS. 64–66 illustrate the sliding finger ring assembly 930. As can be seen, sliding finger ring assembly 930 is comprised of a body portion 931 and first and second finger rings 931A, 931B, respectively, which are attached at either side of body portion 931. Disposed within body portion 931 is guide 934, which defines an aperture 934A within it. Attached to the distal end of guide 934 is actuator guide structure receiving ring 935. The upper portion of body portion 931 and guide 934 define instrument hub receiving aperture 932, the purpose of which is to allow instrument hubs 940 and 950 to be received within finger ring assembly 930, such that hub actuator 960 is able to engage one of the instrument hubs and thus, the instrument hub is able to be moved along body portion 910 along with movement of sliding finger ring assembly 930 along body portion 910. Guide 934 and the lower portion of body portion 931 define surgical instrument body portion receiving aperture 933 which receives the lower body portion of surgical instrument 900 within it. Thus, sliding finger ring assembly 930 is able to be moved along body portion 910 of surgical instrument 900. As will become clear later in this specification, actuator guide structure receiving ring 935 receives within it a portion of hub actuator 960. Thus, hub actuator 960 is structurally mated to finger ring assembly 930 and is able to rotate within the actuator guide structure receiving ring 935 of finger ring assembly 930.

Figure 67:
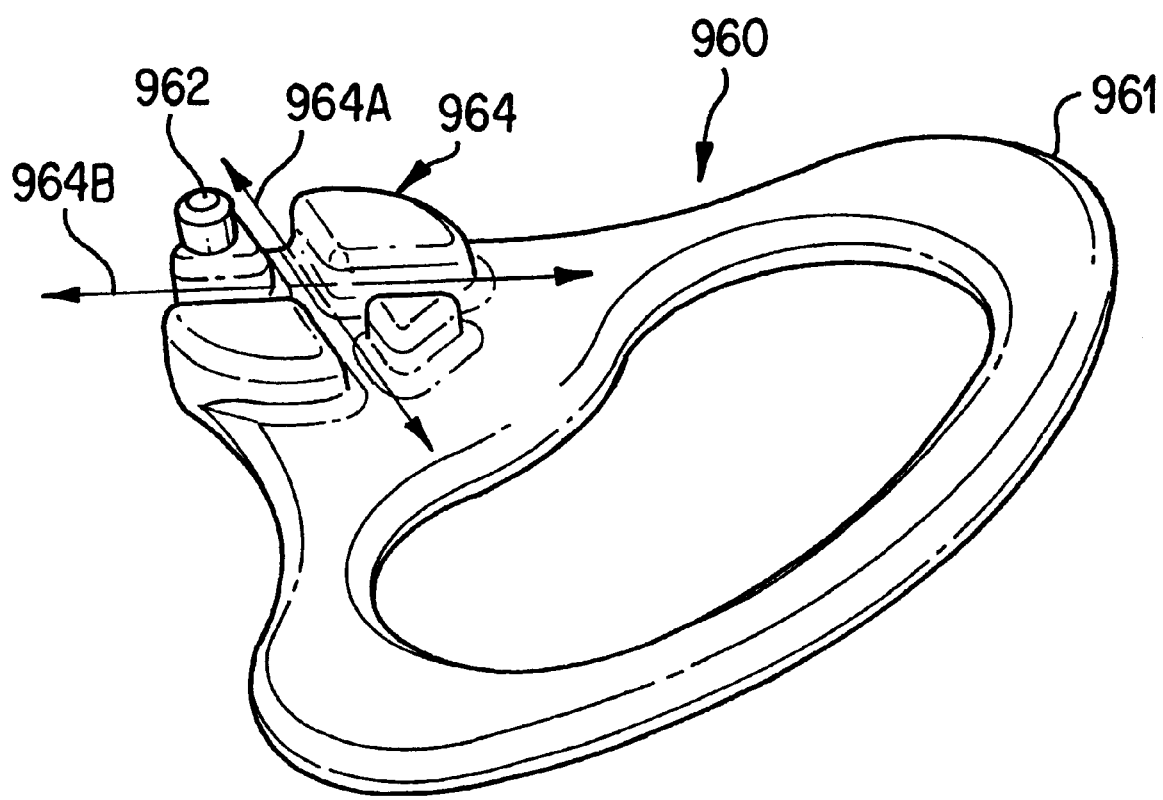
FIG. 67 is a perspective view of the hub actuator of FIG. 51.

FIG. 67 illustrates hub actuator 960. As can be seen, hub actuator 960 is comprised of a finger grip 961, an actuator tab 962, and guide structure 964. Guide structure 964 has an outer circular circumference and defines a first guide slot 964A and a second guide slot 964B. As will become clear, the first and second guide slots alternatively receive within them actuator guide member 924 of guide bar 920. As hub actuator 960 is rotated to engage one of the instrument hubs, the longitudinal axis of one of the guide slots will align with the longitudinal axis of the actuator guide member 924. Thus, hub actuator 960 is able to be moved along guide bar 920 by placing actuator guide member 924 within one of the guide slots defined by guide structure 964. As hub actuator 960 is rotated, such that the hub actuator engages the other of the instrument hubs, then the other of the guide slots will now align longitudinally with actuator guide member 924, such that hub actuator 960 is again able to be moved along guide member 924. Thus, the first and second guide slots are used to guide hub actuator 960 along guide bar 920 when hub actuator 960 engages one of the instrument hubs in surgical instrument 900.

Disposed on guide structure 964 is actuator tab 962. Actuator tab 962 extends from guide structure 964 and is located above the horizontal plane of the upper most portion of guide structure 964. Actuator tab 962 is received within one of instrument hubs 940, 950 to select a particular hub for use by the user of surgical instrument 900. Because hub actuator 960 is rotatably mounted within finger ring assembly 930, actuator tab 962 is able to rotate in order to engage one or the other of the instrument hubs. As was mentioned previously, actuator guide member 924 of guide bar 920 includes an actuator tab slot 925A within it. It is through actuator tab slot 925A that actuator tab 962 is able to pass through actuator guide member 924 to engage each of the instrument hubs 940, 950. As was also previously mentioned, actuator guide member 924 includes actuator guide structure slot 925B. Actuator guide structure slot 925B receives within it guide structure 964 of hub actuator 960. Thus, guide structure 964 of hub actuator 960 is able to rotate without being impeded by the actuator guide member 924.

Figure 68:
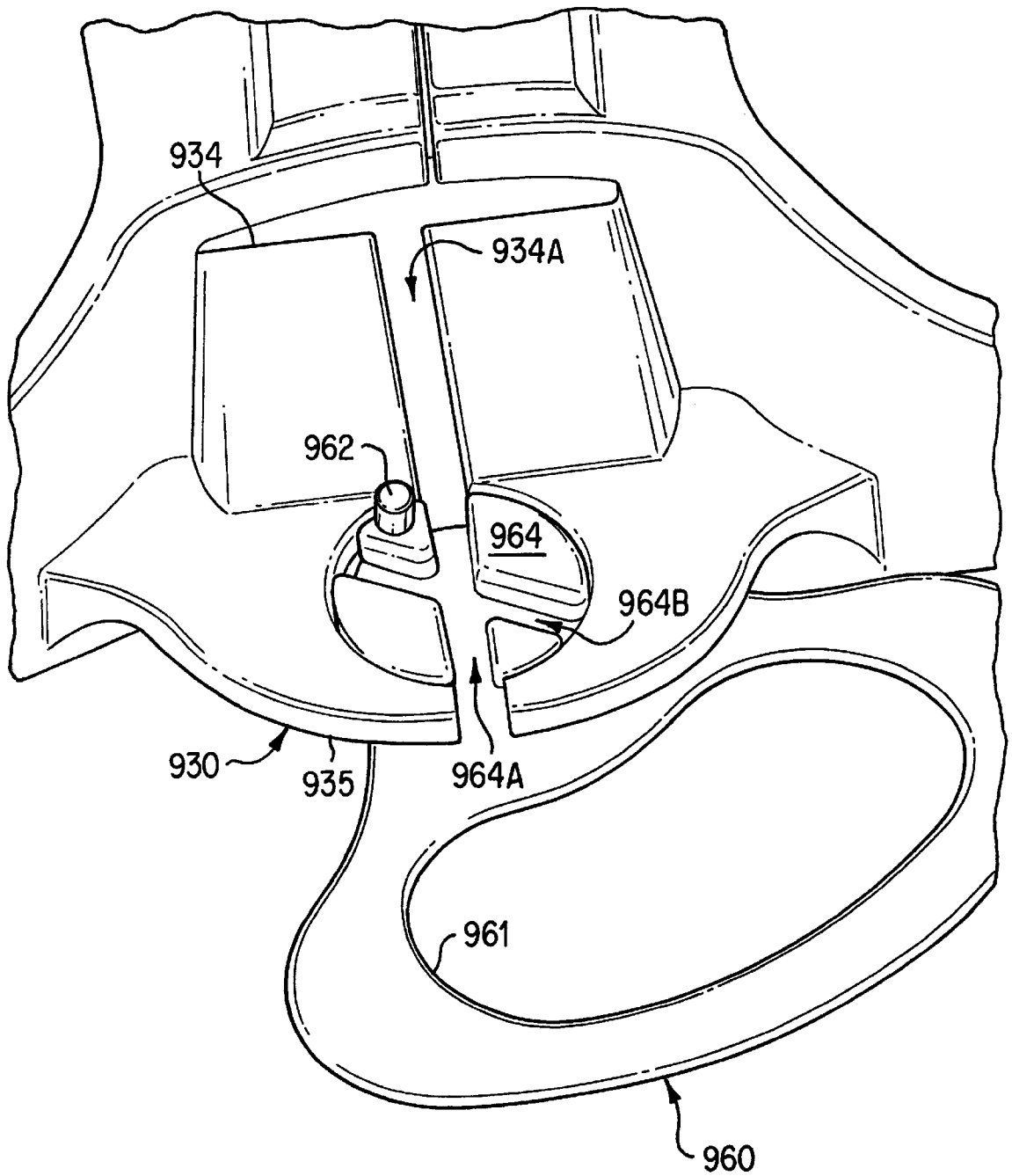
FIG. 68 is a perspective view of the finger ring assembly and hub actuator of the embodiment of FIG. 51.

FIG. 68 illustrates hub actuator 960 and finger ring assembly 930 in an assembled configuration. For purposes of clarity, the sliding instrument hubs and the guide bar 920 are not illustrated. As can be seen, the guide structure 964 of hub actuator 960 is received within the actuator guide structure receiving ring 935 of finger ring assembly 930. As such, hub actuator 960 is structurally mated with sliding finger ring assembly 930 and hub actuator 960 is able to rotate within the sliding finger ring assembly 930. FIG. 68 illustrates hub actuator 960 where it has been rotated such that it would engage first actuator hub 940 if first actuator hub 940 was present in this illustration. It can be seen that in this position for hub actuator 960, the first guide slot 964A of hub actuator 960 aligns with aperture 934A that is formed within guide 934 of sliding finger ring assembly 930. Thus, actuator guide member 924 of guide bar 920 would be received within aligned aperture 934A and slot 964A such that the sliding finger ring assembly 930 and hub actuator 960 would be able to be moved along actuator guide member 924 of guide bar 920 of surgical instrument 900. As can be understood, if hub actuator 960 was rotated such that actuator tab 962 would now engage with second instrument hub 950, second guide slot 964B would align with aperture 934A in sliding finger ring assembly 930 such that both the hub actuator 960 and the sliding finger ring assembly 930 would be able to be moved along actuator guide member 924 of guide bar 920.

Figure 69:
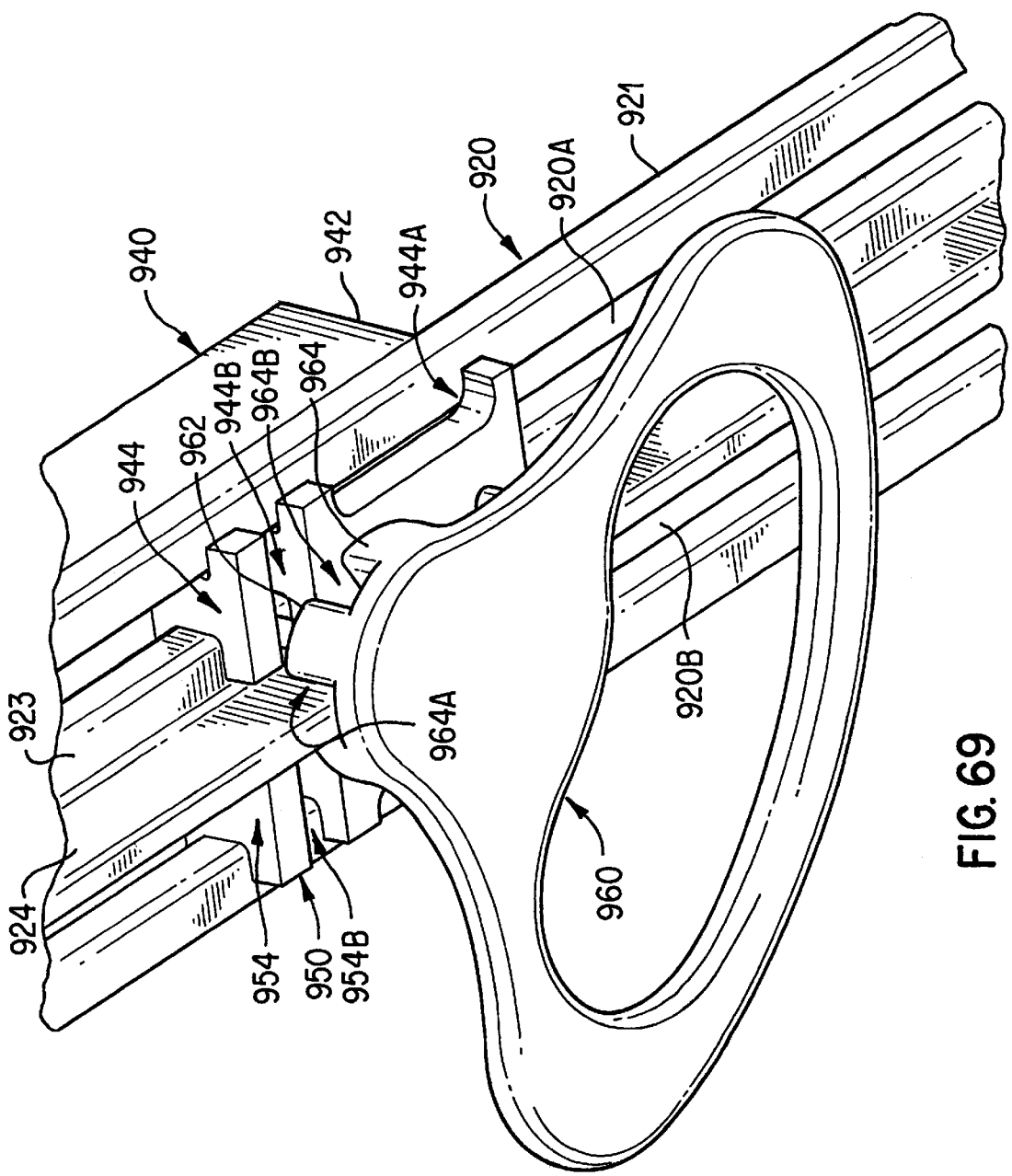
FIG. 69 is a perspective view of the hub actuator, guide bar, and first and second instrument hubs of the embodiment of FIG. 51

FIG. 69 illustrates the hub actuator 960, the guide bar 920, first instrument hub 940 and second instrument hub 950 in an assembled configuration to illustrate the interaction between the instrument hubs, the guide bar, and the hub actuator. For purposes of clarity, the sliding finger ring assembly 930 and body 910 are not illustrated in FIG. 69. As can be seen, hub actuator 960 has been rotated such that actuator tab 962 engages with first instrument hub 940 through interaction with actuator tab engagement slot 944B that is formed within guide portion 944 of first instrument hub 940. As can be further seen in FIG. 69, first instrument hub 940 is slidably mounted on guide bar 920 by placing guide bar 920 within guide slot 944A defined by guide portion 944 of first instrument hub 940. With hub actuator 960 in this position, it can be seen that first guide slot 964A that is formed within guide structure 964 of hub actuator 960 is in axial alignment with actuator guide member 924 of guide bar 920 such that hub actuator 960 is able to be moved along guide bar 920. Thus, it can be understood that because there is a structural connection between hub actuator 960, sliding finger ring assembly 930 (as illustrated in FIG. 68 and as discussed previously), and first instrument hub 940, as sliding finger ring assembly 930 is moved distally along body portion 910 of surgical instrument 900, instrument hub 940 will also be moved along with sliding finger ring assembly 930. Second instrument hub 950 will not move along body portion 910 with sliding finger ring assembly 930 because, in this position for hub actuator 960, there is no structural connection between second instrument hub 950 and sliding finger ring assembly 930 through hub actuator 960.

Figure 70:
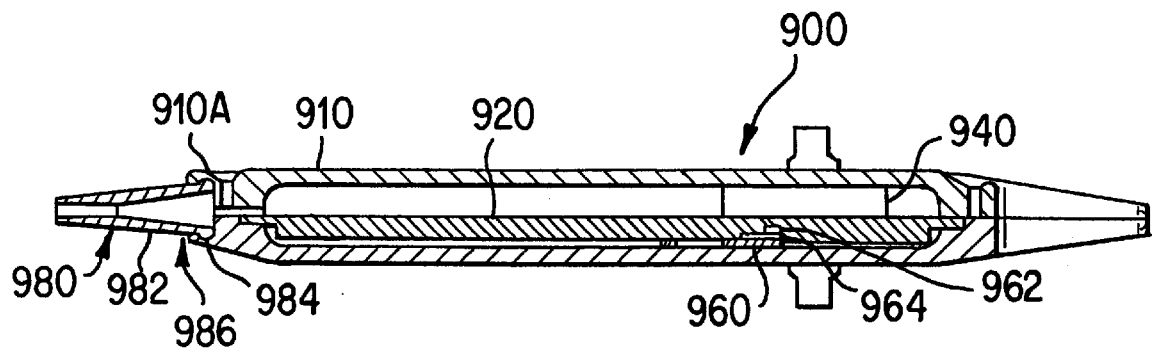
FIG. 70 is a cross-sectional view of the surgical instrument of FIG. 51 taken along line 70—70 of FIG. 52.
Figure 71:
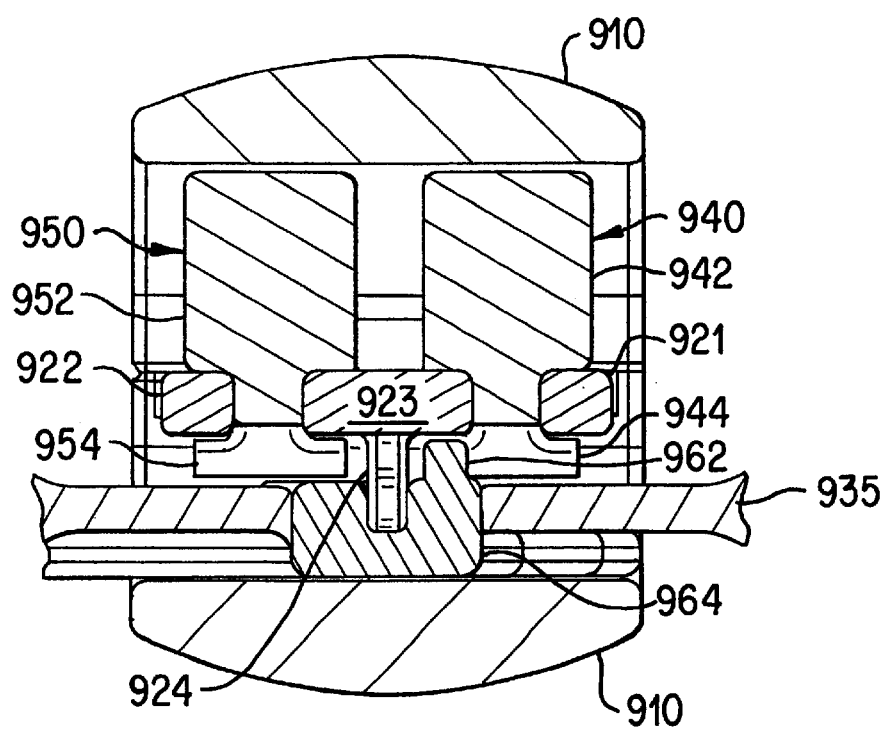
FIG. 71 is a cross-sectional view of the surgical instrument of FIG. 51 taken along line 71—71 of FIG. 52.

FIGS. 70 and 71 provide cross-sectional views of surgical instrument 900 in an assembled configuration. FIG. 70 is a cross-section of surgical instrument 900 taken along line 70—70 of FIG. 52 and FIG. 71 is a cross-section of surgical instrument 900 taken along ling 71—71 of FIG. 52. Both FIGS. 70 and 71 illustrate hub actuator 960 in a position where it has engaged first instrument hub 940.

FIGS. 72–75 illustrate the sheath stress relief member 980 of the present embodiment. As can be seen, sheath stress relief member 980 is comprised of a conical portion 982 and a circular portion 984. Circular portion 984 and a portion of conical portion 982 are mounted within distal end 910A of body portion 910 as can be clearly seen in FIG. 70. A notch 986 is provided in conical portion 982 that cooperates with structure on distal end 910A of body 910 to provide stress relief for the structural connection between stress relief member 980 (and thus a sheath (not shown) that is attached to conical portion 982 of stress relief member 980) and body 910. As can be seen, an aperture extends through sheath stress relief member 980 and is aligned with an aperture that is included in distal end 910A of body 910 such that the surgical tools that are associated with surgical instrument 900 may extend through body portion 910 and sheath stress relief member 980 and into the sheath that would be attached to the distal end of the surgical instrument.

In operation, a user of surgical instrument 900 would rotate actuator tab 960 to engage one of the instrument hubs 940, 950 to select a tool for use that is associated with the instrument hubs. By engaging an instrument hub with hub actuator 960, the selected instrument hub can be moved along body portion 910 of surgical instrument 900 when the sliding finger ring assembly 930 is moved along body portion 910. To select the other instrument hub for use, the user of surgical instrument 900 rotates hub actuator 960 such that it engages with that instrument hub. Thus, a user of surgical instrument 900 is able to selectively engage a surgical tool for use within surgical instrument 900. Whereas the non-engaged instrument hub is not locked-out from use, it can not be moved along body portion 910 of surgical instrument 900 through movement of sliding finger ring assembly 930.

Figure 76:
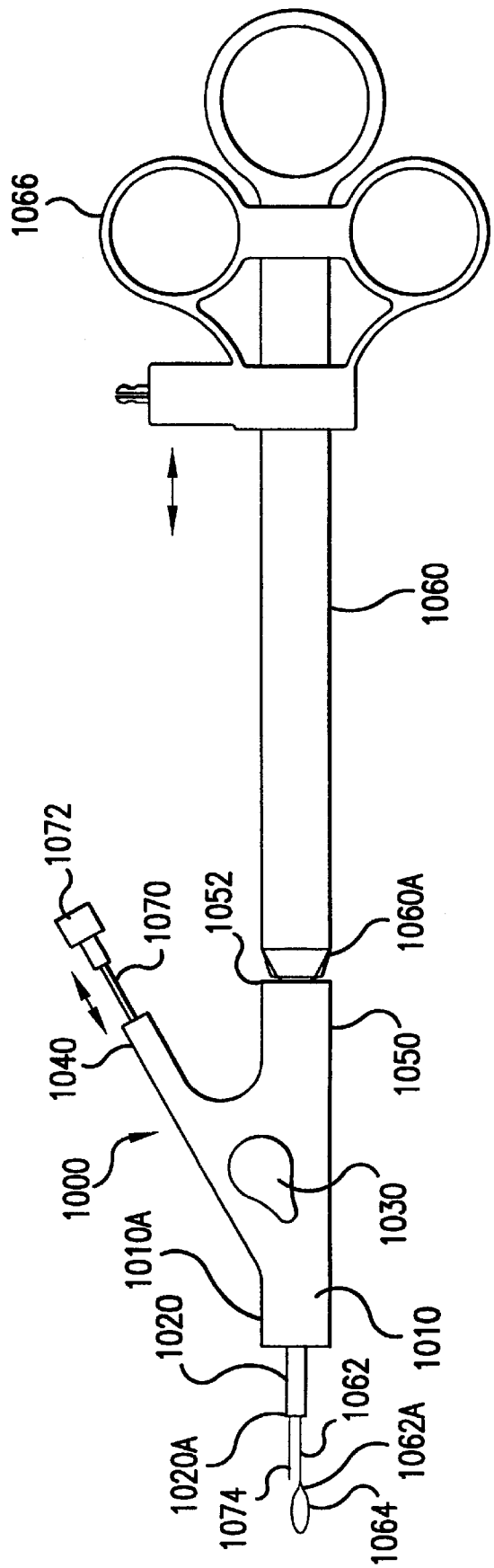
FIG. 76 is a side view of a tenth embodiment for the tool actuator assembly of the present invention.
Figure 77:
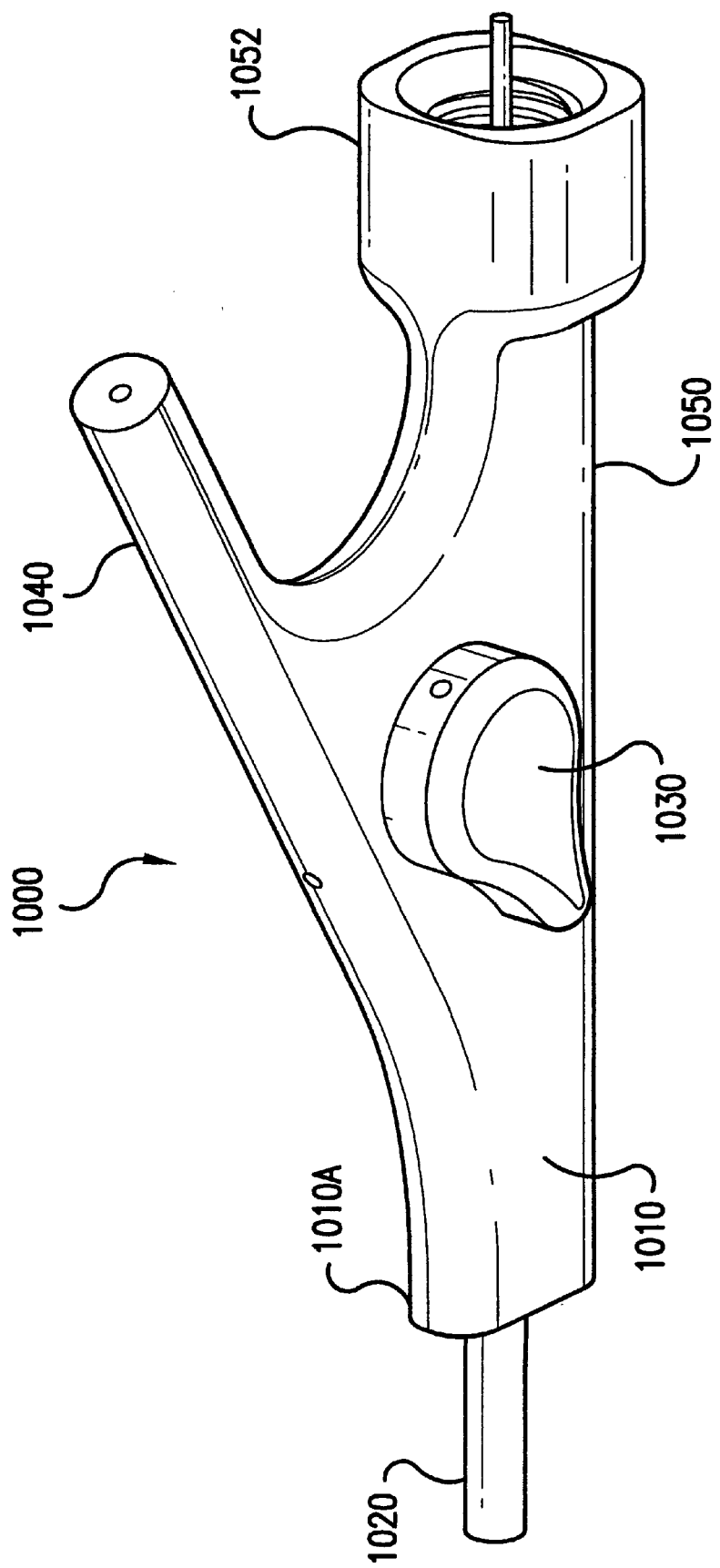
FIG. 77 is a perspective view of the tool actuator assembly of FIG. 76.

FIGS. 76–79 illustrate a tenth embodiment for a tool actuator assembly in accordance with the present invention. FIGS. 76 and 77 illustrate the tool actuator assembly 1000. As can be seen in FIG. 76, tool actuator assembly 1000 is comprised of a body 1010, a first tool receiving member 1040, a second tool receiving member 1050, and a tool lock-out switch 1030. Tool actuator assembly 1000 also includes catheter 1020, which is attached to distal end 1010A of tool actuator assembly 1000.

Body 1010 is a hollow structure that receives through it a first surgical tool, which is illustrated as injection needle 1070 in FIG. 76, and a second surgical tool, which is illustrated as snare instrument 1060 in FIG. 76. Injection needle 1070 is received within first tool receiving member 1040 and extends through body 1010 and catheter 1020 where, in an operative position, needle tip 1074 of injection needle 1070 extends beyond the distal end 1020A of catheter 1020. Injection needle 1070 includes injection port 1072 which is utilized in well-known methods. Injection needle 1070 is able to be moved manually in the directions as illustrated in FIG. 76, such that needle tip 1074 may be extended from catheter 1020 and retracted into catheter 1020.

Second tool receiving member 1050 is internally threaded at its proximal end 1052. As such, snare instrument 1060, which can be a well-known snare instrument, can be threaded into second tool receiving member 1050. As such, distal end 1060A of snare instrument 1060 is externally threaded so that it may be received within second tool receiving member 1050. Snare rod 1062 of snare instrument 1060 extends from snare instrument 1060 through second tool receiving member 1050 and body 1010 of tool actuator assembly 1000. As such, snare loop 1064, which is located at distal end 1062A of snare rod 1062, is able to be extended from, and retracted into, catheter 1020.

Snare rod 1062 is attached to sliding finger ring assembly 1066 of snare instrument 1060 and thus is able to be extended from, and retracted into, catheter 1020 by moving sliding finger ring assembly 1066 along the body of snare instrument 1060 in the directions as illustrated in FIG. 76. As will be explained further below, tool lock-out switch 1030, which is rotatably mounted on body 1010 and which extends into body 1010, is utilized to lock-out from operation one of the surgical tools from operation while the other of the surgical tools is being utilized by the physician.

FIG. 76 illustrates tool actuator assembly 1000 being utilized with an injection needle 1070 and a snare instrument 1060, however, the present invention is not limited to only being utilized with these two particular tools. Tool actuator assembly 1000 can be utilized with any known surgical tool and can be utilized to lock-out from operation one surgical tool while the other surgical tool is being utilized by the physician.

Figure 78:
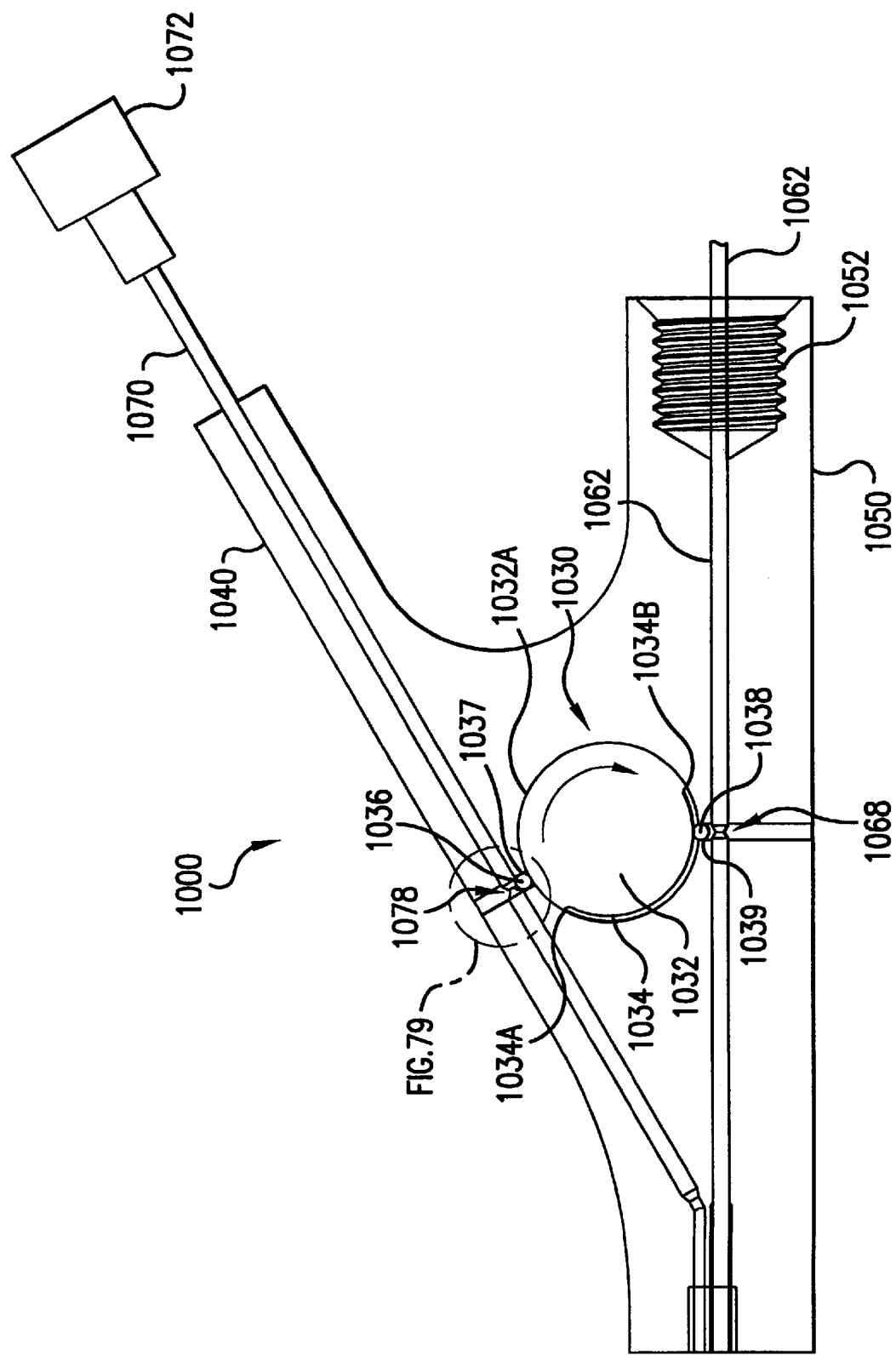
FIG. 78 illustrates the internal working components of the tool actuator assembly of FIG. 76.

FIG. 78 illustrates the internal working components of tool actuator assembly 1000. As can be seen, within body 1010 tool lock-out switch 1030 is comprised of a hub 1032 which includes a trough 1034 that extends around a portion of the outer circumference of hub 1032. Trough 1034 provides for a reduced diameter for hub 1032 along the portion of hub 1032 where trough 1034 is located. The purpose of trough 1034 will be explained below. Also associated with tool lock-out switch 1030 are first locking member 1036 and second locking member 1038. Each of the first and second locking members 1036, 1038 are illustrated as ball structures. These locking members are positioned within body 1010 within channels that are formed within body 1010. As such, first locking member 1036 is contained within first body channel 1037 and second locking member 1038 is contained within second body channel 1039. First locking member 1036 is disposed between injection needle 1070 and hub 1032 and second locking member 1038 is disposed between snare rod 1062 and hub 1032. Thus, first locking member 1036 is operably associated with injection needle 1070 and hub 1032 and second locking member 1038 is operably associated with snare rod 1062 and hub 1032.

Figure 79:
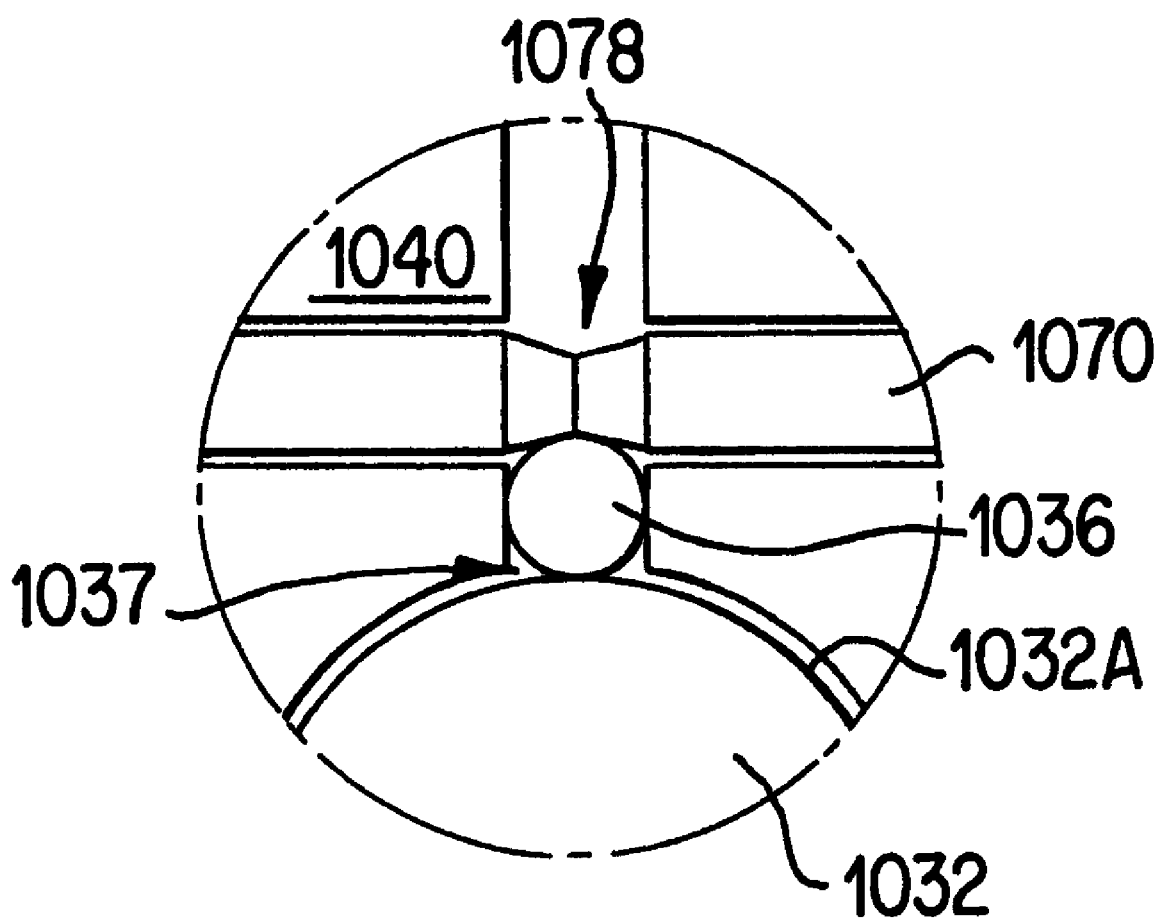
FIG. 79 illustrates the needle, first locking member, and hub of the tool actuator assembly of FIG. 78.

FIG. 79 provides greater detail for the assembled configuration between needle 1070, first locking member 1036, and hub 1032. As can be seen in FIG. 79, needle 1070 is provided with a joint 1078 within it. Needle joint 1078 provides for a decreased diameter at the center of the joint than that for the needle along the needle's shaft. Snare rod 1062 is also provided with a similar joint that may be seen in FIG. 78 as snare joint 1068.

In operation, tool lock-out switch 1030 locks-out from operation one of the surgical tools extending through tool actuator assembly 1000 by engaging a locking member with its associated tool shaft at the joint of the tool shaft. The reduced diameter of the joint of the tool shaft allows for the locking member to be positioned within this area of reduced diameter in the shaft in order to prevent the tool shaft from being extended further through tool actuator assembly 1000 and thus extended from the distal end 1020A of catheter 1020. Due to the providing of trough 1034 within hub 1032, as one of the locking members is engaged with its associated tool to lock-out the operation of the tool, the other of the locking members will be positioned within the trough 1034 of hub 1032 and thus will not be forced by hub 1032 into contact with the shaft of its associated tool. Thus, the second surgical tool can be easily moved distally and proximally through body portion 1010 of tool actuator assembly 1000 such that the tool can be utilized by the surgeon in performed a procedure.

FIG. 78 illustrates a position for lock-out switch 1030 where injection needle 1070 has been locked-out from operation by first locking member 1036. As can be seen, first locking member 1036 has been forced into engagement with needle joint 1078 through contact between first locking member 1036 and the outer circumference 1032A of hub 1032. As can also be seen when lock-out switch 1030 is in this position, second locking member 1038 is received within trough 1034 of hub 1032. Thus, second locking member 1038 is not rigidly engaged with snare rod 1062 and thus, snare rod 1062 is able to be freely moved within body 1010.

As can be understood, in FIG. 78, if hub 1032 was rotated in a clockwise direction, this clockwise rotation of 1032 would then position first locking member 1036 within trough 1034 and second locking member 1038 would be caused to be forced out of trough 1034 and would be positioned against outer circumference 1032A of hub 1032. After this clockwise rotation of hub 1032, first locking member 1036 would no longer be in rigid contact with injection needle 1070 and thus injection needle 1070 would now be able to be freely moved within body 1010 such that it may be extended from, and retracted into, catheter 1020. It can also be understood that now second locking member 1038 will be forced into rigid contact with snare rod 1062 at its connection joint 1068 and thus this rigid connection between second locking member 1038 and snare joint 1062 will prevent snare rod 1062 from being moved freely within body 1010. Thus, after hub 1032 has been rotated in this clockwise direction, now injection needle 1070 may be freely used by the surgeon to perform a procedure and snare 1060 has now been locked-out from use by the surgeon. The end regions 1034A and 1034B of trough 1034 can be formed with camming surfaces such the locking members may easily ride up and out of the trough 1034 as the hub 1032 is rotated from one lock-out position to another lock-out position.

The disclosed embodiments are illustrative of the various ways in which the present invention may be practiced. Other embodiments can be implemented by those skilled in the art without departing from the spirit and scope of the present invention.

What is claimed is:

1. A multi-function surgical instrument comprising:
    a tubular body;
    a finger ring assembly slidably mounted on said body;
    a shaft slidably mounted within a distal end of said body;
    a first surgical tool disposed within said shaft and said body and connected to said finger ring assembly;
    a second surgical tool disposed within said shaft and said body and connected to a proximal end of said body; and
    an actuator member slidably mounted on said body and attached to said shaft.

2. The multi-function surgical instrument of claim 1 wherein:
    said body defines a guiding slot at a distal end of said body; and
    said actuator member includes:
        a head portion, said head portion disposed outside of said body;
        an elongated stem portion, said stem portion extending from said head portion and partially disposed within said body; and
        a slot guide, said slot guide disposed on said elongated stem portion and received within said guiding slot.

3. The multi-function surgical instrument of claim 2 wherein said slot guide includes a first guide tab and a second guide tab and wherein said first and second guide tabs are disposed on opposing sides of said elongated stem portion.

4. The multi-function surgical instrument of claim 1 wherein said actuator member includes:
    an engagement head portion disposed proximal to said finger ring assembly;
    a shaft attachment portion disposed at said distal end of said body; and
    a connection member, said connection member attached to said engagement head portion and said shaft attachment portion and disposed within said body.

5. The multi-function surgical instrument of claim 4 further comprising a biasing member, said biasing member disposed within said body at said proximal end of said body and located proximal to said actuator member and said finger ring assembly.

6. The multi-function surgical instrument of claim 1 wherein said first surgical tool is a snare.

7. The multi-function surgical instrument of claim 1 wherein said second surgical tool is an injection needle.

8. The multi-function surgical instrument of claim 7 further comprising an injection port attached to said injection needle.

9. The multi-function surgical instrument of claim 1 wherein said first surgical tool is a snare and said second surgical tool is an injection needle.

10. The multi-function surgical instrument of claim 9 further comprising an injection port attached to said injection needle.

11. The multi-function surgical instrument of claim 1 wherein said shaft is rigid.

12. The multi-function surgical instrument of claim 1 wherein said shaft is flexible.

13. The multi-function surgical instrument of claim 1 wherein said finger ring assembly defines an aperture therethrough and wherein said second surgical tool extends through said aperture.

14. A multi-function surgical instrument comprising:
- a tubular body, said tubular body defining a guiding slot at a distal end of said body;
- a finger ring assembly slidably mounted on said body;
- a shaft slidably mounted within said distal end of said body;
- a first surgical tool disposed within said shaft and said body and connected to said finger ring assembly;
- a second surgical tool disposed within said shaft and said body and connected to a proximal end of said body; and
- an actuator member slidably mounted on said body and attached to said shaft, said actuator member including:
  - a head portion, said head portion disposed outside of said body;
  - an elongated stem portion, said stem portion extending from said head portion and partially disposed within said body; and
  - a slot guide, said slot guide disposed on said elongated stem portion and received within said guiding slot.

15. The multi-function surgical instrument of claim 14 wherein said slot guide includes a first guide tab and a second guide tab and wherein said first and second guide tabs are disposed on opposing sides of said elongated stem portion.

16. The multi-function surgical instrument of claim 14 wherein said first surgical tool is a snare.

17. The multi-function surgical instrument of claim 14 wherein said second surgical tool is an injection needle.

18. The multi-function surgical instrument of claim 17 further comprising an injection port attached to said injection needle.

19. The multi-function surgical instrument of claim 14 wherein said first surgical tool is a snare and said second surgical tool is an injection needle.

20. The multi-function surgical instrument of claim 19 further comprising an injection port attached to said injection needle.

21. The multi-function surgical instrument of claim 14 wherein said shaft is rigid.

22. The multi-function surgical instrument of claim 14 wherein said shaft is flexible.

23. The multi-function surgical instrument of claim 14 wherein said finger ring assembly defines an aperture therethrough and wherein said second surgical tool extends through said aperture.

* * * * *